(12) United States Patent
Urey

(10) Patent No.: US 10,444,507 B2
(45) Date of Patent: Oct. 15, 2019

(54) NEAR-TO-EYE DISPLAY DEVICE WITH SPATIAL LIGHT MODULATOR AND PUPIL TRACKER

(71) Applicant: CY Vision Inc., Mountain View, CA (US)

(72) Inventor: Hakan Urey, Istanbul (TR)

(73) Assignee: CY Vision Inc., San Jose, CA (US)

( * ) Notice: Subject to any disclaimer, the term of this patent is extended or adjusted under 35 U.S.C. 154(b) by 85 days.

(21) Appl. No.: 15/633,721

(22) Filed: Jun. 26, 2017

(65) Prior Publication Data

US 2018/0003981 A1  Jan. 4, 2018

Related U.S. Application Data

(60) Division of application No. 15/632,164, filed on Jun. 23, 2017, which is a continuation of application No. (Continued)

(51) Int. Cl.
*G02B 27/01* (2006.01)
*G02B 27/48* (2006.01)
(Continued)

(52) U.S. Cl.
CPC .......... *G02B 27/0172* (2013.01); *A61B 3/032* (2013.01); *G02B 5/0242* (2013.01); (Continued)

(58) Field of Classification Search
CPC .............. G02B 27/0172; G02B 27/017; G02B 2027/0178; G02B 27/0101; G02B 27/01; (Continued)

(56) References Cited

U.S. PATENT DOCUMENTS

| 4,311,999 A | 1/1982 | Upton et al. |
| 7,850,306 B2 | 12/2010 | Uusitalo et al. |

(Continued)

FOREIGN PATENT DOCUMENTS

| WO | WO_2007027019 A1 | 3/2007 |
| WO | WO_2008065569 | 6/2008 |
| WO | WO_2014063716 | 5/2014 |

OTHER PUBLICATIONS

Reichelt, Stephan, et al. "Holographic 3-D displays-electroholography within the grasp of commercialization." Advances in Lasers and Electro Optics. InTech, 2010. (Year: 2010).*

(Continued)

*Primary Examiner* — Xiao M Wu
*Assistant Examiner* — Scott E Sonners
(74) *Attorney, Agent, or Firm* — Charles A. Lemaire; Jonathan M. Rixen; Lemaire Patent Law Firm, P.L.L.C.

(57) ABSTRACT

A near-to-eye display device includes a spatial light modulator, a rotatable reflective optical element and a pupil-tracking device. The pupil-tracking device tracks the eye pupil position of the user. Based on the data provided by the pupil-tracking device, the reflective optical element is rotated such that the light modulated by the spatial light modulator is directed towards the user's eye pupil.

23 Claims, 66 Drawing Sheets

Related U.S. Application Data

PCT/TR2014/000513, filed on Dec. 26, 2014, and a continuation of application No. PCT/TR2014/000514, filed on Dec. 26, 2014, and a continuation of application No. PCT/TR2014/000515, filed on Dec. 26, 2014, and a continuation of application No. PCT/TR2014/000516, filed on Dec. 26, 2014, and a continuation of application No. PCT/TR2014/000512, filed on Dec. 26, 2014.

(51) Int. Cl.

| | |
|---|---|
| *G06T 15/00* | (2011.01) |
| *G09G 3/02* | (2006.01) |
| *G09G 3/34* | (2006.01) |
| *G06T 11/60* | (2006.01) |
| *A61B 3/032* | (2006.01) |
| *G02B 5/02* | (2006.01) |
| *G03H 1/22* | (2006.01) |
| *G06T 19/00* | (2011.01) |
| *G06T 11/00* | (2006.01) |
| *A61B 3/113* | (2006.01) |

(52) U.S. Cl.
CPC .......... *G02B 27/48* (2013.01); *G03H 1/2202* (2013.01); *G03H 1/2205* (2013.01); *G03H 1/2286* (2013.01); *G03H 1/2294* (2013.01); *G06T 11/60* (2013.01); *G06T 15/00* (2013.01); *G09G 3/02* (2013.01); *G09G 3/3466* (2013.01); *A61B 3/113* (2013.01); *G02B 2027/014* (2013.01); *G02B 2027/0112* (2013.01); *G02B 2027/0125* (2013.01); *G02B 2027/0138* (2013.01); *G02B 2027/0145* (2013.01); *G02B 2027/0174* (2013.01); *G02B 2027/0178* (2013.01); *G02B 2027/0187* (2013.01); *G03H 2001/2207* (2013.01); *G03H 2001/2231* (2013.01); *G03H 2001/2234* (2013.01); *G03H 2001/2242* (2013.01); *G03H 2210/30* (2013.01); *G03H 2222/34* (2013.01); *G03H 2225/60* (2013.01); *G03H 2227/02* (2013.01); *G03H 2240/61* (2013.01); *G06T 11/00* (2013.01); *G06T 19/006* (2013.01)

(58) Field of Classification Search
CPC .... G02B 2027/0174; G02B 2027/0187; G02B 27/0179; G02B 2027/0125; G02B 27/0093; G02B 27/0081; G02B 27/0176; G02B 26/0833; G02B 27/0103; G02B 27/0149; G02B 27/0944; G02B 27/0955; G02B 27/22; G02B 26/0858; G02B 27/1006; G02B 27/1026; G02B 27/1046; G02B 27/283; G06F 3/011; G06F 3/013; G06T 19/006; H04N 13/332; H04N 9/3102; H04N 9/3155; H04N 9/3164; H04N 2213/008; H04N 9/315; G06K 9/00671; G09G 3/346; G03B 21/005; G03H 1/08; G03H 1/2645; G03H 1/265; G03H 2001/266; G03H 1/005; G03H 1/26

See application file for complete search history.

(56) References Cited

U.S. PATENT DOCUMENTS

| | | | |
|---|---|---|---|
| 8,049,941 | B2 | 11/2011 | Haussler |
| 8,294,966 | B2 | 10/2012 | Kroll et al. |
| 8,400,696 | B2 | 3/2013 | Ikeda et al. |
| 9,291,828 | B2 | 3/2016 | Kroll et al. |
| 9,383,582 | B2 | 7/2016 | Tang et al. |
| 9,406,166 | B2 | 8/2016 | Futterer |
| 2005/0024754 | A1 | 2/2005 | Epstein et al. |
| 2005/0052376 | A1 | 3/2005 | Shivji |
| 2010/0149073 | A1* | 6/2010 | Chaum ............. G02B 27/0093 345/8 |
| 2010/0259804 | A1 | 10/2010 | Buschbeck et al. |
| 2011/0128471 | A1 | 6/2011 | Suckling et al. |
| 2013/0208003 | A1 | 8/2013 | Bohn et al. |
| 2013/0222384 | A1* | 8/2013 | Futterer ................. G02B 5/32 345/426 |
| 2014/0146394 | A1* | 5/2014 | Tout ...................... G09B 9/307 359/630 |
| 2015/0378162 | A1* | 12/2015 | Bailey .................... G02B 27/30 345/8 |

OTHER PUBLICATIONS

Koulieris, George Alex, et al. "Near-Eye Display and Tracking Technologies for Virtual and Augmented Reality." Computer Graphics Forum. Wiley-Blackwell, 2019. (Year: 2019).*

Reichelt, et al., "Holographic 3-D Displays—Electro-holography", "In: Advances in Lasers and Electro Optics (Chapter 29) Available on internet at: http://www.intechopen.com", Apr. 1, 2010, Publisher: Intech XP055149317.

"PCT International Preliminary Report on Patentability (Chapt. I) for related PCT/TR2014/000512 application, dated Jun. 27, 2017, 8 pages."

"PCT International Preliminary Report on Patentability (Chapt. I) for related PCT/TR2014/000513 application, dated Jun. 27, 2017, 7 pages."

"PCT International Preliminary Report on Patentability (Chapt. I) for related PCT/TR2014/000514 application, dated Jun. 27, 2017, 11 pages."

"PCT International Preliminary Report on Patentability (Chapt. I) for related PCT/TR2014/000515 application, dated Jun. 27, 2017, 9 pages."

"PCT International Preliminary Report on Patentability (Chapt. I) for related PCT/TR2014/000516 application, dated Jun. 27, 2017, 7 pages."

* cited by examiner

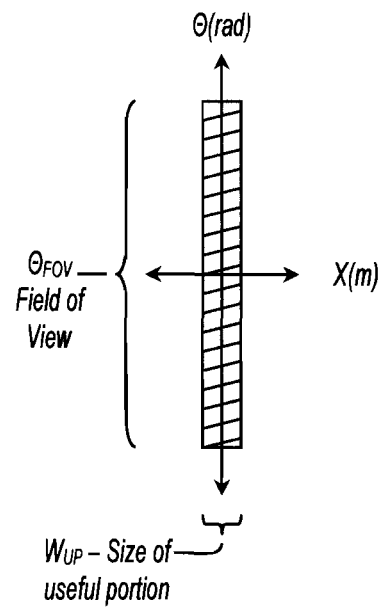
FIG. 57
FIG. 58
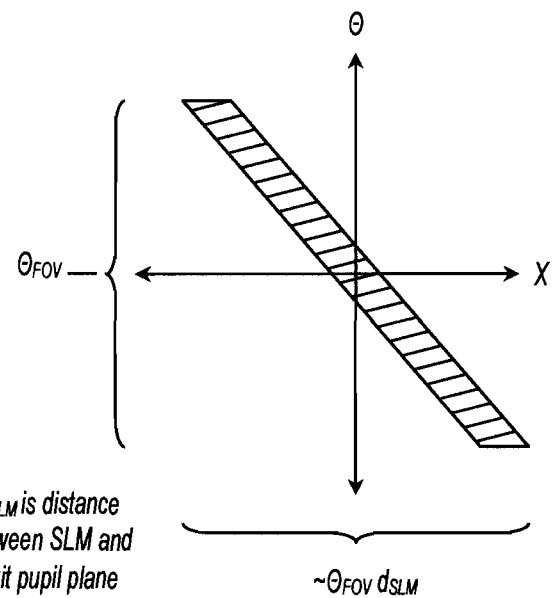

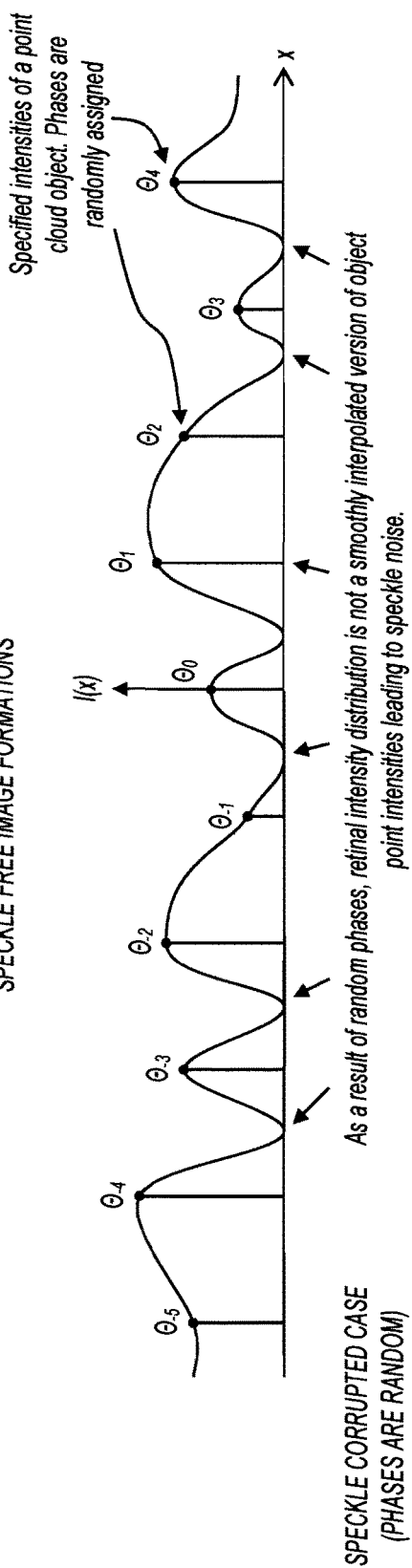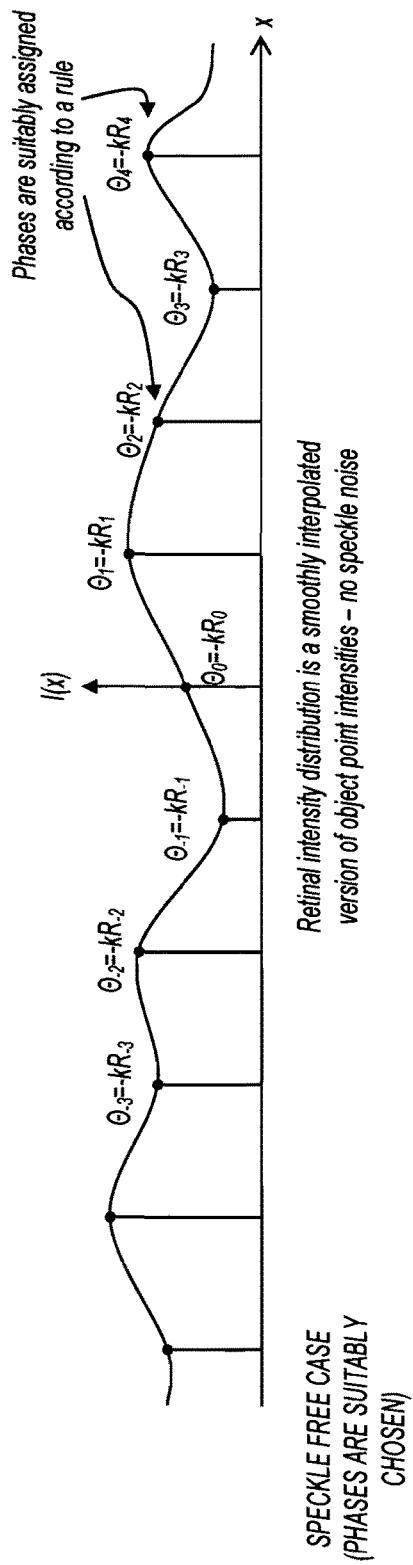
FIG. 66 ILLUSTRATION OF ONE DIMENSIONAL SPECKLE CORRUPTED AND SPECKLE FREE IMAGE FORMATIONS

SECTION A-A

SECTION A-A

NEAR-TO-EYE DISPLAY DEVICE WITH SPATIAL LIGHT MODULATOR AND PUPIL TRACKER

CROSS-REFERENCE TO RELATED APPLICATIONS

This is a divisional application of U.S. patent application Ser. No. 15/632,164 filed Jun. 23, 2017 by Hakan Urey et al., titled "NEAR-TO-EYE DISPLAY DEVICE," which is a continuation of, and claims priority benefit under 35 USC § 365(c) of, PCT Patent Application No. PCT/TR2014/000512 filed Dec. 26, 2014 by Hakan Urey et al., titled "NEAR-TO-EYE DISPLAY DEVICE," PCT Patent Application No. PCT/TR2014/000513 filed Dec. 26, 2014 by Hakan Urey, titled "NEAR-TO-EYE DISPLAY DEVICE WITH SPATIAL LIGHT MODULATOR AND PUPIL TRACKER," PCT Patent Application No. PCT/TR2014/000514 filed Dec. 26, 2014 by Hakan Urey et al., titled "NEAR-TO-EYE DISPLAY DEVICE WITH MOVING LIGHT SOURCES," PCT Patent Application No. PCT/TR2014/000515 filed Dec. 26, 2014 by Hakan Urey et al., titled "APPARATUS FOR GENERATING A COHERENT BEAM ILLUMINATION," and PCT Patent Application No. PCT/TR2014/000516 filed Dec. 26, 2014 by Hakan Urey et al., titled "NEAR-TO-EYE DISPLAY DEVICE WITH VARIABLE RESOLUTION," each of which is incorporated herein by reference in its entirety.

FIELD OF THE INVENTION

The present invention relates generally to optical systems, and more specifically to near-to-eye display devices.

BACKGROUND

Head-worn displays (HWD) typically employ a microdisplay on which a two-dimensional (2D) regular image is displayed. Since the physical distance between the microdisplay and the eye is typically much smaller than 25 cm (the closest distance at which the human eye can normally focus), a blurred image forms on the retina unless relay optics are placed in between. The relay optics typically consist of several lenses which serve to form a magnified virtual image of the microdisplay beyond 25 cm (mostly at infinity) on which the eye can then focus and form a sharp retinal image.

Lightweight HWD designs that employ microdisplays (those that use only a single magnifier lens, for instance) are mostly restricted to systems having small fields of view (FOV), since weight and bulk increase for large FOV designs due to additional components inserted to compensate for aberrations. As an example, the recently emerging Google Glass (which has a quite thin form factor) basically consists of a small (~1-cm diagonal) microdisplay and a simple positive lens, but has a limited FOV, beyond which aberrations become severe. On the other hand, high-end military-type displays may support an FOV approaching 150 degrees or more, but weigh as much as 5 kg or more and may contain more than 10 different lenses, most of which are present to compensate for aberrations that emerge due to the enlarged FOV. Having so many lenses is not merely a technological problem, but a fundamental one, since no single optical component can be designed to form an aberration free image of a large size microdisplay, due to the fact that the information emerging from the microdisplay quickly gets spread in space as it propagates.

Microdisplay-based HWD designs also fall short of providing the ultimate three-dimensional (3D) visual experience. These HWD designs typically provide only stereoscopic images, which invoke 3D perception essentially only through binocular disparity. Monocular cues, especially accommodation, are typically not supported, or are incorrect. Users of stereoscopic systems typically suffer from visual fatigue caused by the so-called accommodation-convergence conflict, in which eyes converge truly to the apparent position of a 3D object while accommodation is set incorrectly to the screen so as to make retinal images sharp. The fatigue is especially severe when virtual objects are closer than 50 cm.

BRIEF DESCRIPTION OF THE DRAWINGS

FIG. 57-64 show a number of space-angle (or space-frequency) distributions that illustrate the basics of the computation procedure;

FIG. 66 illustrates the fundamentals of the method for delivering speckle-free images to the retina of a user;

DESCRIPTION OF EMBODIMENTS

Figure 1:
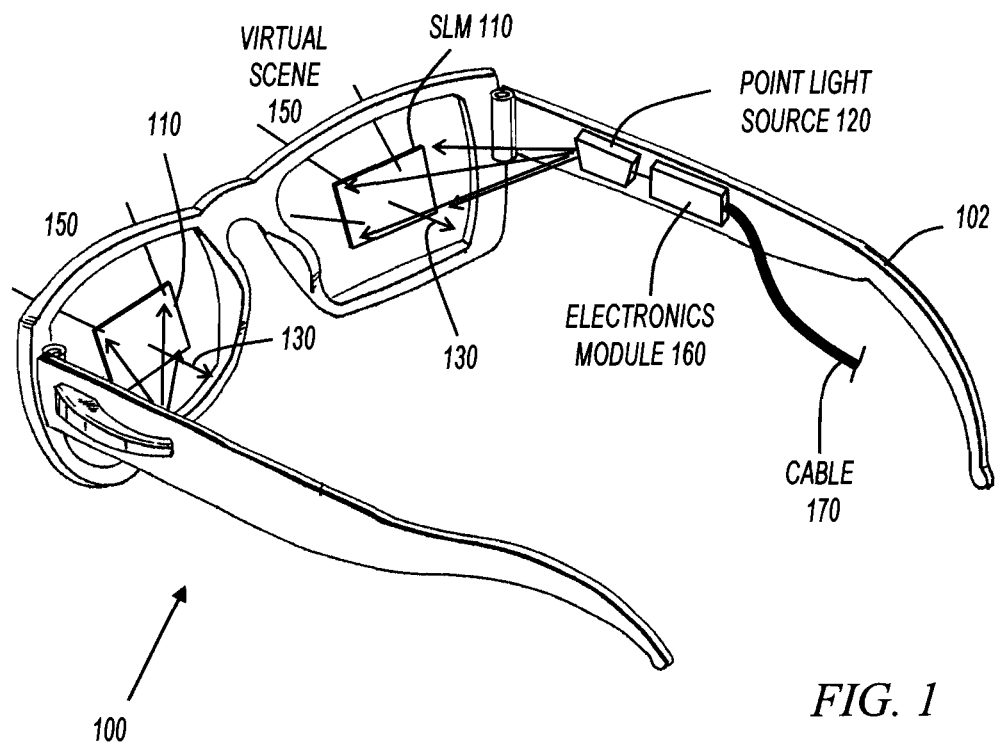
FIG. 1 shows a perspective view of a near-to-eye display device.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein in connection with one embodiment may be implemented within other embodiments without departing from the scope of the invention. In addition, it is to be understood that the location or arrangement of individual elements within each disclosed embodiment may be modified without departing from the scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

FIG. 1 shows a perspective view of a near-to-eye display device. Near-to-eye display device 100 includes a frame 102 in the shape of an eyeglass frame. Near-to-eye display device 100 also includes spatial light modulators (SLM) 110, point light source 120, electronics module 160, and cable 170. In embodiments represented by FIG. 1, the near-to-eye display device is a head-worn device (HWD), although this is not a limitation of the present invention. In some embodiments, near-to-eye display devices are not head-worn. Various examples of non-head-worn near-to-eye display devices are discussed further below.

Point light source 120 may include any type of light source. For example, in some embodiments, point light source 120 includes a laser light source. Also for example, in some embodiments, point light source 120 includes an ultraviolet (UV) light source, an infrared (IR) light source, or other source of visible or nonvisible light.

In operation, near-to-eye display device 100 displays a monochrome or full-color video of a 2D or 3D virtual scene 150 that appears to be located on the outer side of the eyeglass to the user. For each frame of the displayed video, point light source 120 generates a coherent light wave of a single wavelength that illuminates a spatial light modulator (SLM 110) that is mounted on the front section of the eyeglass. The SLM spatially modulates the phase and/or amplitude of the incident wave and reflects it towards the eye of the user, shown generally at 130. In some embodiments, near-to-eye display device 100 is a monochrome display device, and point light source 120 only generates a coherent light wave of a single color. In other embodiments, near-to-eye display device 100 is a full-color display device, and point light source 120 generates coherent light waves of different wavelengths in a time sequential manner.

For each video frame, the data on the SLM is a computer-generated holographic image of the virtual scene. The data on the SLM is computed and fed by a computer unit, which can be mounted on frame 102 as electronics module 160, or can be connected to the display device by cable 170 or wireless links (not shown).

Electronics module 160 may include any suitable components. For example, in some embodiments, electronics module 160 includes driver circuits to drive point light source 120, and digital processing components to store SLM data and to drive the SLMs 110 with that data. Also for example, electronics module 160 may include a processor and memory, or any other suitable electronics components.

In some embodiments, SLM data is computed real-time as it is displayed. In these embodiments, electronics module 160 computes the SLM data and drives SLMs 110 with the SLM data to create virtual scene 150 in real-time. The real-time SLM data may be a function of head-tracking data, pupil-tracking data, environmental data (e.g., ambient light, objects in the user's field of view, etc.).

In other embodiments, SLM data is precomputed and stored for retrieval at display time. For example, SLM data for an entire virtual environment may be precomputed and stored. As a user traverses the virtual environment, the appropriate SLM data is retrieved and displayed. In still further embodiments, portions of the SLM data are precomputed, and portions of the SLM data are computed real-time.

Point light source 120 is shown on an outer portion of frame 102, and SLM 110 is reflective. In other embodiments, point light source is located differently, and the SLM is transmissive. For example, in some embodiments, point light source 120 is mounted on the nose bridge between the two SLMs, and the light generated by point light source 120 is fed to a back-light unit that illuminates the SLM from the opposite side than shown in FIG. 1. These and other optical architectures are described below with reference to later figures.

Figure 2:
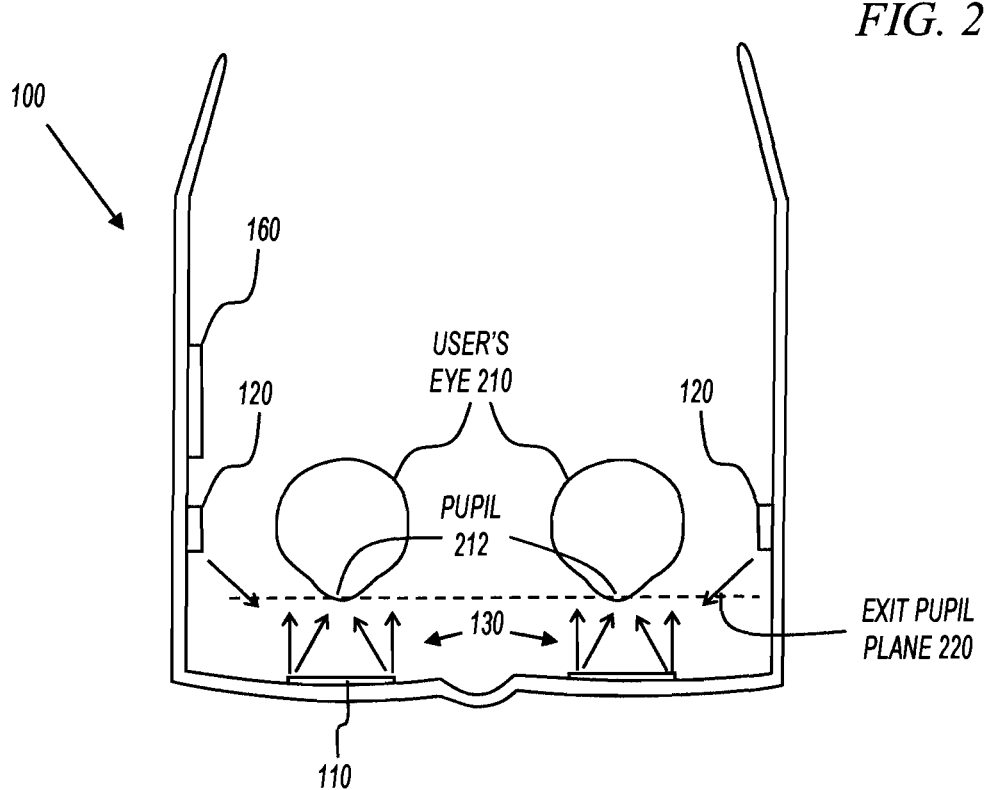
FIG. 2 shows a top view of the near-to-eye display device of FIG. 1.

FIG. 2 shows a top view of the near-to-eye display device of FIG. 1. The wave 130 reflected by SLM 110 propagates towards the user's eye 210 and forms a light wave distribution on the exit pupil plane 220, which is defined as the plane that lies just in front of the user's eye, and corresponds to the expected location of the user's eye pupil 212. Part of the light wave distribution formed on the exit pupil plane is intercepted by the user's eye pupil 212 and propagates to the retina, where a 3D image of the virtual scene is formed. In some embodiments, a real-world view is superimposed on the virtual scene, and in other embodiments, the real-world view is blocked, and the only image formed on the retina is the virtual scene.

In general, systems that display a virtual scene and block the real-world view are referred to as "virtual reality" (VR) systems, and systems that superimpose the real-world view with the virtual scene are referred to as "augmented reality" (AR) systems.

Figure 3:
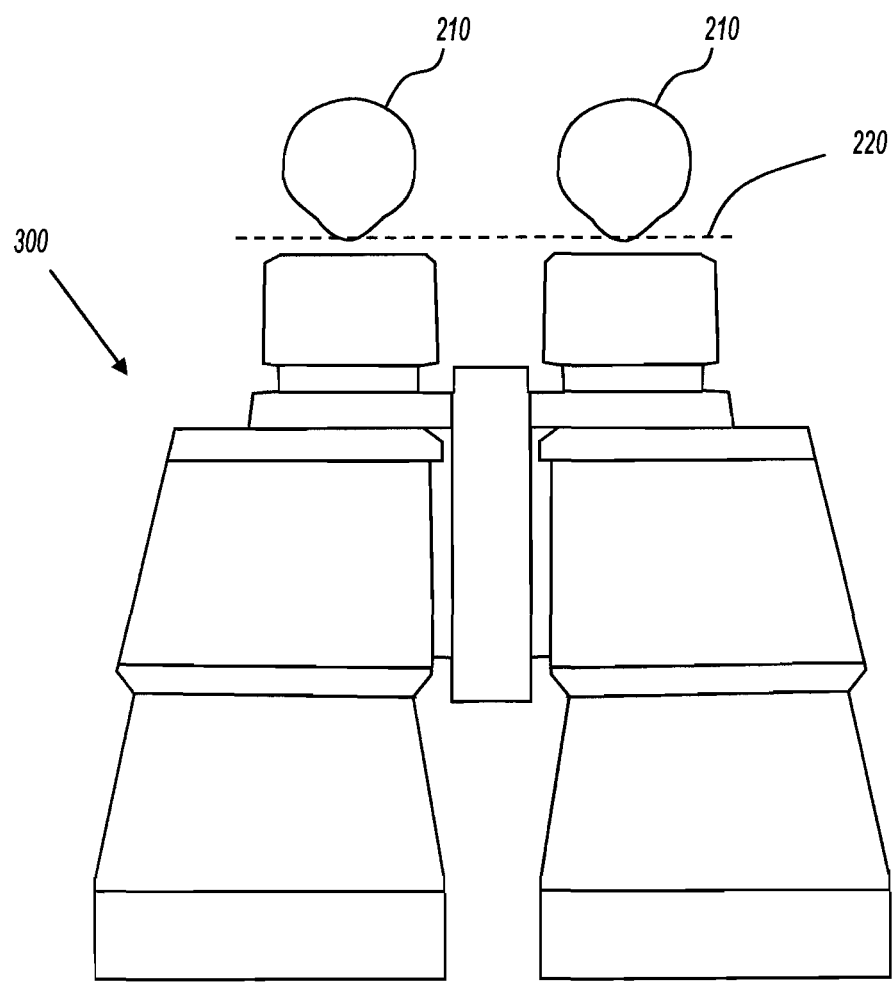
FIG. 3 shows a handheld near-to-eye display device.

FIG. 3 shows a handheld near-to-eye display device. As used herein, the term "near-to-eye display device" refers to any device that produces a light wave distribution of a virtual scene on an exit pupil plane from a physical distance that is less than the typical minimal distance at which the human eye can normally focus (e.g., 25 cm). A near-to-eye display device may be handheld as in FIG. 3, or may head-worn as in FIG. 1. A near-to-eye display device may also be stationary for applications in which a user is expected to place their head against or near the near-to-eye display device (e.g., VR demonstrators). The example handheld near-to-eye display device of FIG. 3 is in the shape of a pair of binoculars, but this is not a limitation of the present invention. Any type of near-to-eye display device: head-worn, handheld (e.g., electronic viewfinders in cameras, foldable image viewer, smartphones), or otherwise, may include embodiments of the present invention.

Any near-to-eye display device (e.g., near-to-eye display device 300) may include any of the invention embodiments described herein. For example, any near-to-eye display device may include any of the embodiments that produce a light wave distribution on the exit pupil plane 220 described herein.

Figure 4:
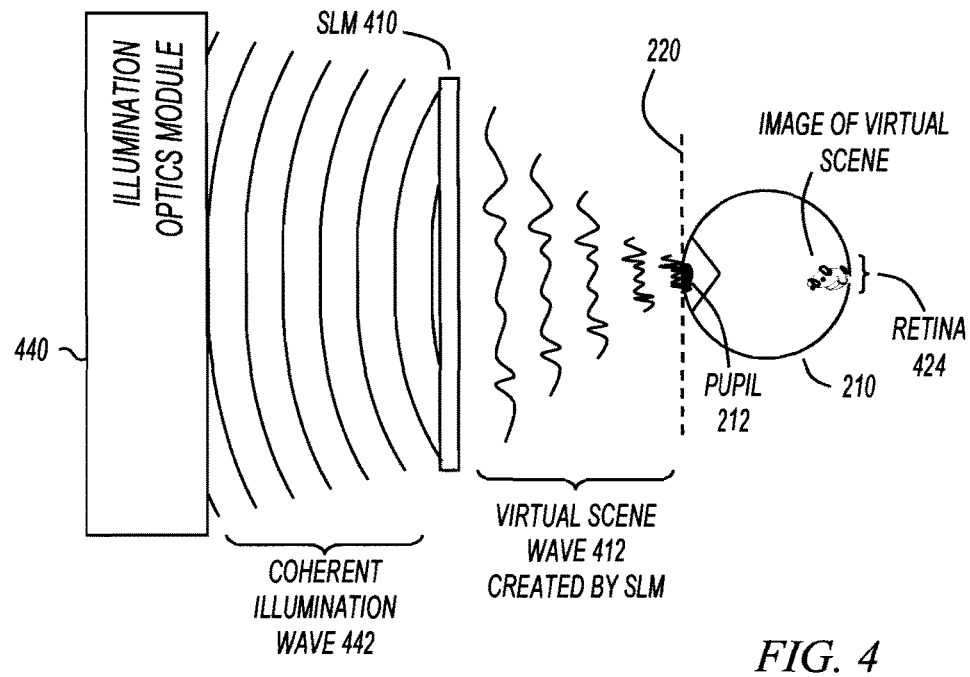
FIG. 4 shows a cross section of a spatial light modulator (SLM) being illuminated and generating a virtual-scene wave.

FIG. 4 shows a cross section of an SLM being illuminated and generating a virtual-scene wave. SLM 410 is shown as a transmissive SLM. Illumination optics module 440 produces, and illuminates SLM 410 with, a coherent illumination wave 442. SLM 410 modulates the light and creates virtual-scene wave 412. Encoded in virtual-scene wave 412 is a 3D virtual scene that is imaged on the user's retina 424. Only the portion of the virtual-scene wave that intersects the user's pupil 212 on the exit pupil plane 220 creates an image on the retina. Other information in the virtual-scene wave that falls outside the user's pupil is filtered out and does not enter the user's eye. Various invention embodiments that employ pupil filtering are discussed in more detail below.

Illumination optics module 440 shown here creates a converging illumination wave. In some embodiments, this is accomplished with light sources and optical components such as mirrors, micromirror arrays, lenses, and the like. Various embodiments of illumination optics modules are described in more detail below. In some embodiments, the illumination optics module does not necessarily generate a converging illumination wave. For example, one simple example of an illumination optics module is a point light source 120 (FIG. 1). In that case, the illumination wave is a diverging wave. Yet, in other embodiments shown below, the illumination wave is generated by arrays containing multiple point light sources. However, in any case, the illumination wave must possess a certain degree of spatial coherency over sufficiently large areas of the SLM.

SLMs are basically dynamically programmable diffractive optical elements. Various different SLM technologies exist. SLMs based on nematic liquid crystals (LC) make use of the electrically controlled refractive index of anisotropic LCs to modulate polarization, intensity or phase of incident light. The type of modulation depends on the mode of the LC that is used. Twisted nematic LCs rotate the polarization of incident light by some controlled amount, and are used along with polarizers on both sides to constitute intensity modulators suitable for incoherent light applications, most commonly, 2D displays. Parallel aligned nematic (PAN) (or electrically controlled birefringence (ECB)) mode LCs are most suitable for coherent light applications, and they can be used as multilevel phase only SLMs. Transmissive SLMs based on LCs have large pixel pitch due to the fact that electronic circuitry associated with each pixel must be embedded within the pixel aperture. Reflective SLMs based on Liquid Crystal on Silicon (LCoS) technology can be made to have much smaller pixel pitches, since electronics can be buried under the pixel. One advantage of SLMs based on nematic LCs is the multilevel modulation these devices can perform. However, their performance is limited by pixel crosstalk and low frame rates, which may be problematic in color field sequential holographic applications. SLMs based on ferroelectric LCs have much higher frame rates at the cost of merely binary modulation at each pixel.

Microelectromechanical systems (MEMS) based SLMs are advantageous in terms of frame rate and basically no pixel crosstalk. Digital Micromirror Device (DMD) can be used as SLM. However, it provides only binary modulation. Moreover, the complicated pixel structure of these devices makes it difficult to reduce the pixel pitch. Other MEMS SLMs can be implemented using deformable membrane structures, piston motion micromirror arrays, programmable diffraction gratings such as grating light valve devices, electro-wetting and magneto-optic Kerr effect devices, or MEMS laser scanners.

Various embodiments of the present invention may employ any of the SLM technologies discussed above, or others, including but not limited to: Optically Addressed SLMs, Acousto-Optical SLMs, Magneto Optical SLMs, MEMS mirrors, and the like.

Figure 5:
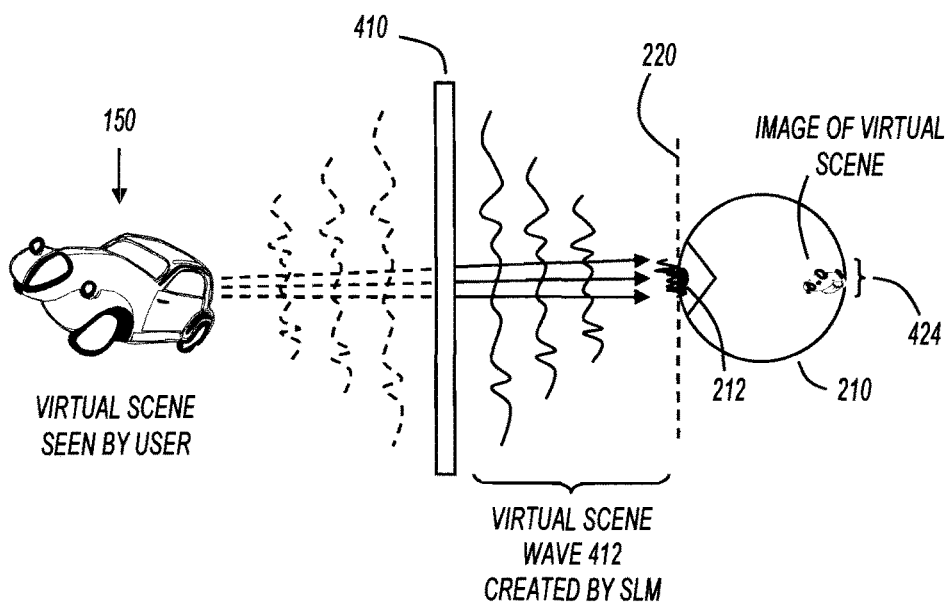
FIG. 5 shows the cross section of FIG. 4 depicting the virtual scene as seen by a user.

FIG. 5 shows the cross section of FIG. 4 depicting the virtual scene as seen by a user. Virtual scene 150 includes one virtual object: a 3D representation of a car. Any number of objects may be included in the virtual scene without departing from the scope of the present invention. In operation, SLM 410 converts the illumination wave to the virtual-scene wave that would be emanated by virtual scene 150.

The restrictions of SLMs have important implications on the capabilities, limitations, and design of the various embodiments of the invention. As explained above, and as shown in FIG. 4, in operation, the SLM is illuminated by a coherent wavefront, which is generated by a group of optical components and light sources that are part of illumination optics module 440. The computer-generated holographic image displayed on the SLM helps convert the illumination wave to the virtual-scene wave that would be emanated by virtual scene 150. Therefore, the SLM is the device where information about the virtual scene is fed to the light wave that is delivered to the eye of the user. However, due to the restrictions and limitations of real SLMs, the SLM is able to synthesize only a portion of the wave emanated by the virtual scene, and the incident wave is only partially converted to the wave emanated by the virtual scene.

In particular, real SLMs have finite spatial sizes, which restrict the size of a virtual scene that is displayed (or, the field of view (FOV) within which the virtual scene is visible), and finite spatial bandwidths (pixel pitches usually several multiples of wavelength), which limits the portion of the wave emanating from each virtual-scene point that can be reconstructed.

SLMs also generate higher diffraction orders as a result of their pixelated structure. These orders correspond to shifted replicas of virtual scenes that are to be displayed, which appear as ghost image replicas if they are allowed to enter the eye and propagate to the retina.

Further, computer-generated holographic images that perform the conversion of an illumination wave to waves emanated by the virtual scene are in general analog and complex-valued, whereas practical SLMs can only perform some restricted type of modulation: phase only, amplitude only, binary, etc., and do provide only a limited number of distinct values. Therefore, a restricted type computer-generated holographic image, which quantizes and encodes the ideal complex-valued computer-generated holographic image, is computed and displayed on the SLM. However, this procedure leads to the emergence of additional undesired beams, that we refer to as "noise beams," in addition to the desired wave. The encoding should be performed such that the resulting noise beams do not enter into the eye, because otherwise, significant background noise will be observed over displayed images.

In the case of SLMs that essentially provide real valued modulation, such as binary SLMs or amplitude only SLMs, a conjugate beam will be formed. This conjugate beam, which corresponds to the wave emitted by a second virtual scene which is the mirror image of the actual virtual scene with respect to the exit pupil plane, should also be prevented from entering the eye.

Further, some SLMs leave a component of the incident wave unmodulated. This component, which we refer to as the unmodulated "DC beam," should also be prevented from entering the eye.

Computational methods for generating the holographic images to be displayed on the SLM are described further below with reference to later figures.

Figure 6:
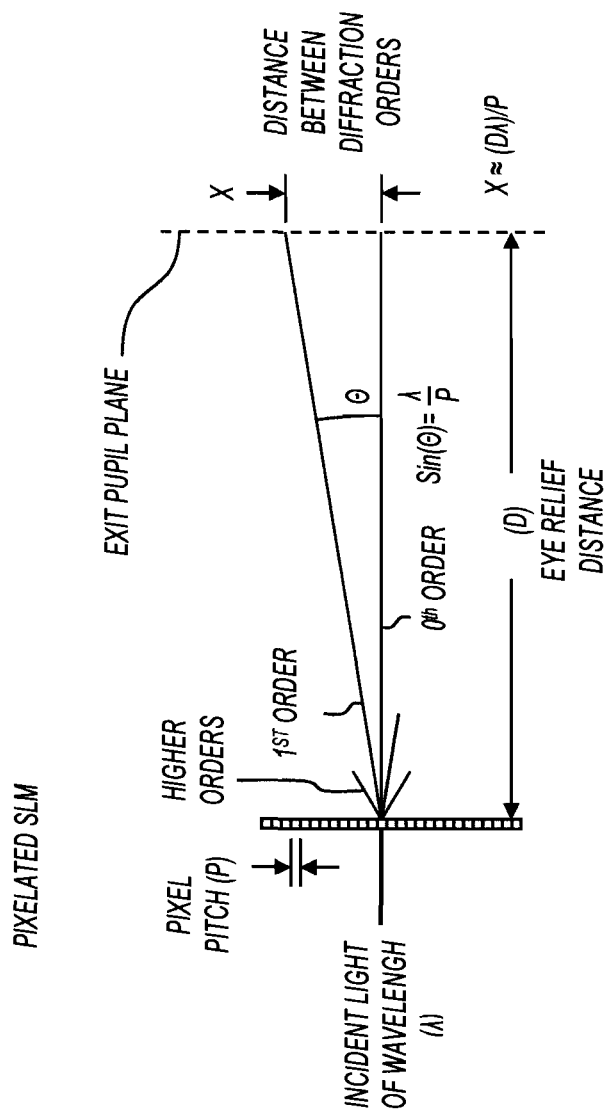
FIG. 6 shows a spatial light modulator with a pixelated structure.

FIG. 6 shows an SLM with a pixelated structure. The pixelated structure of SLMs is intimately linked with sampling and interpolation of light waves. The final analog optical-mask structure that is implemented on the SLM can be considered to be obtained by sampling and re-interpolating the ideal holographic image that is intended to be displayed on the SLM. Rate of sampling is determined by pixel pitch of the SLM, while the pixel aperture function of the SLM constitutes the interpolating function. It is well known that when a signal is sampled in the space domain, its spectrum is periodically replicated in the spatial frequency domain. Thus, the spectrum of the ideal holographic image that is intended to be displayed on the SLM is replicated as a result of sampling, where these replicas are referred to as "higher diffraction orders (HDO)." Since the pixel aperture function of practical SLMs are space limited functions (having Fourier transforms consisting of decaying but non-limited tails), the replicas partially survive in the Fourier transform of the final analog mask implemented by the SLM, leading to observable higher diffraction orders.

As a simple example, FIG. 6 shows an SLM having a pixel pitch P at an eye relief distance D from a user's eye.

The distance X between diffraction orders on the exit pupil plane can be approximated for small angles as $$X \approx \frac{D\lambda}{P} \qquad (1)$$

where $\lambda$ is the wavelength of light incident on the SLM.

As discussed further below, various embodiments of the present invention select values for pixel pitch, expected eye relief distance, wavelength, and other parameters, such that the user's eye pupil forms an effective spatial filter.

The hatch pattern shown in the SLM of FIG. 6 and other figures is not to any particular scale. The hatch pattern, when included, is used as a visual aid to differentiate SLMs from other optical components in the figures, and is not meant to imply an actual pixel-pitch scale.

Figure 7:
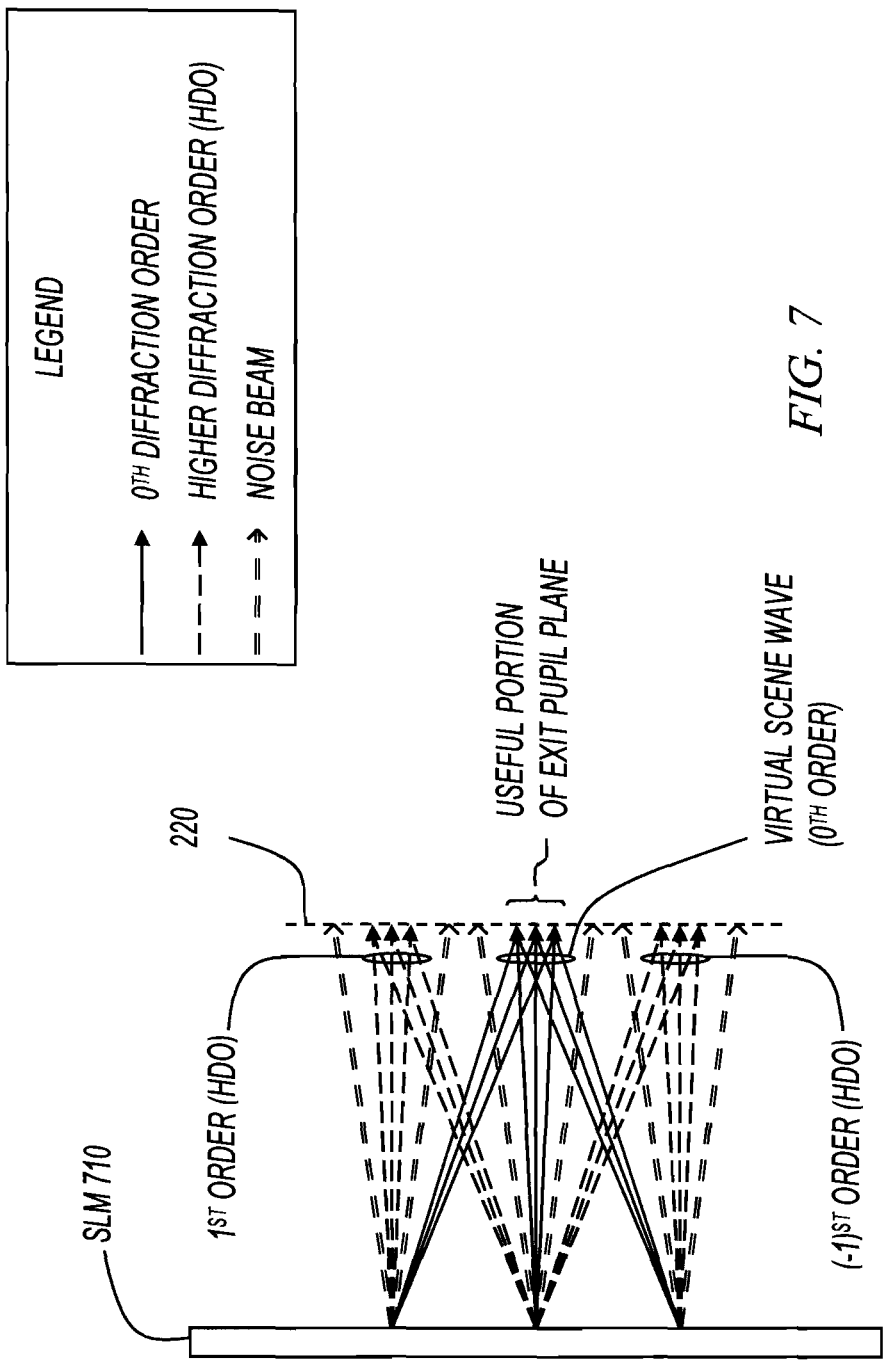
FIG. 7 shows a cross section of an SLM that generates noise beams and multiple diffraction orders.

FIG. 7 shows a cross section of an SLM that generates noise beams and multiple diffraction orders. SLM 710 may be either transmissive or reflective. FIG. 7 shows the light modulated by the SLM, but does not show the illumination wave. The illumination wave may come from any direction. The light wave distribution falling on the exit pupil plane 220 includes the virtual-scene wave (the $0^{th}$ order), higher diffraction orders (HDO), and noise beams.

The useful portion of the exit pupil plane is that portion that ideally includes the virtual-scene wave and nothing else. As shown in FIG. 7, noise beams and HDOs are not included in the useful portion of the exit pupil plane. As described further below, when a user's eye pupil is substantially aligned with the useful portion of the exit pupil plane, the correct virtual scene represented by the virtual-scene wave is imaged on the user's retina.

Figure 8:
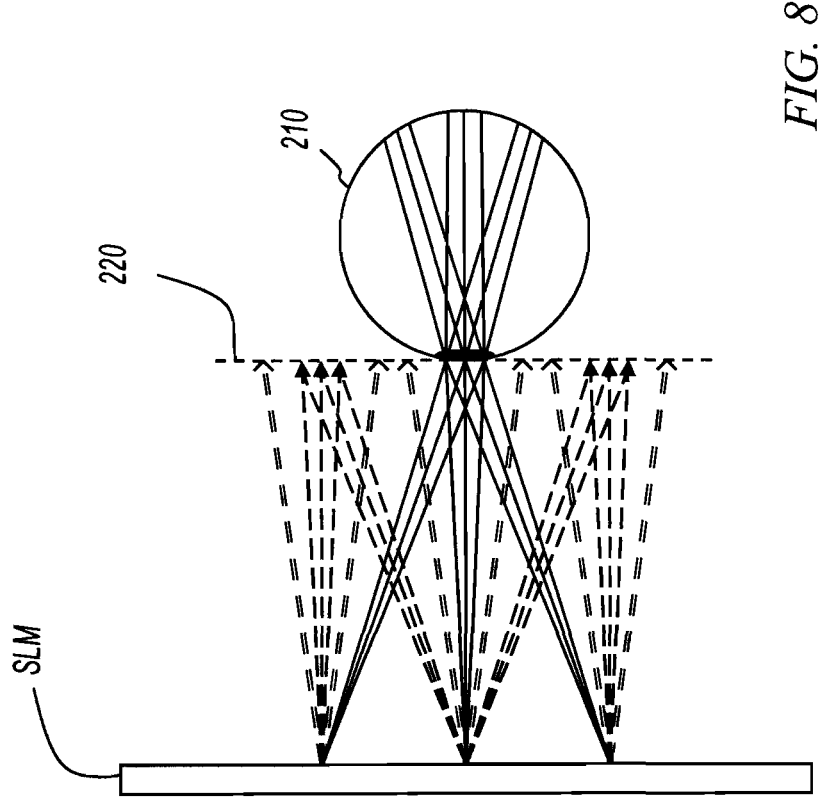
FIG. 8 shows the cross section of FIG. 7 with a user's eye pupil filtering out unwanted noise beams and diffraction orders.

FIG. 8 shows the cross section of FIG. 7 with a user's eye pupil filtering out unwanted noise beams and diffraction orders. Embodiments represented by FIG. 8 eliminate HDOs, noise beams, DC beams, conjugate beams, and other possibly disturbing beams by using the eye pupil of the user as a spatial filter. In these embodiments, no attempt to eliminate the undesired beams is made (optically or computationally) within the near-to-eye display device before these beams reach the exit pupil plane. However, the optical architecture of the system is designed and the holographic image on the SLM is computed such that on the exit pupil plane, there is a useful portion within which only the virtual-scene wave exists, and all other undesired beams fall outside this region. If the size of this useful portion is at least equal to the size of the pupil of the user, and (if needed) this useful portion is steered to follow the pupil movements of the user, then the undesired beams are automatically eliminated by the user's pupil and do not propagate to the retina. This technique, which we refer to as "pupil filtering," has the benefit of reducing the bulk within optical designs, but demands the SLM pixel pitch to be sufficiently small, or equivalently, spatial bandwidth of the SLM to be sufficiently high (see FIG. 6).

In some embodiments where pupil filtering is not applicable, optical filters (such as 4f filters) may be used within the system to eliminate HDOs and noise beams before they reach the exit pupil plane. However, in these embodiments, the bulk within the system increases. Most embodiments of the invention described herein employ pupil filtering, and therefore benefit from reduced bulk and weight.

Figure 9:
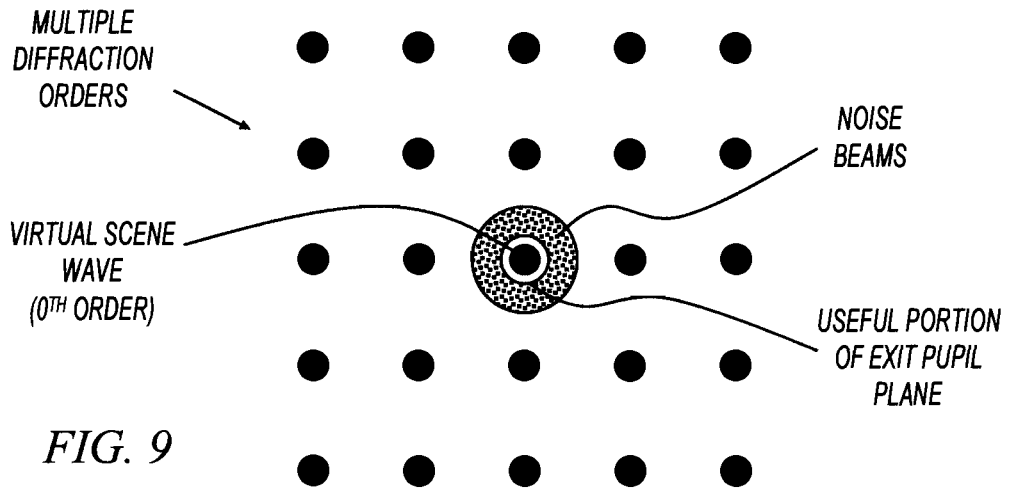
FIGS. 9, 10, and 11 show multiple diffraction orders on an exit pupil plane with a useful portion.
Figure 10:
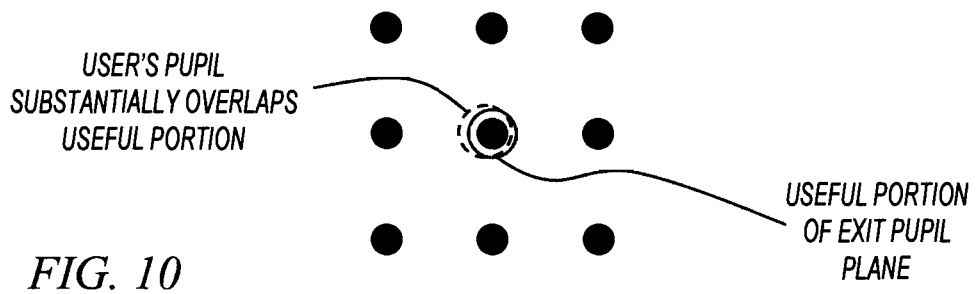
Figure 11:
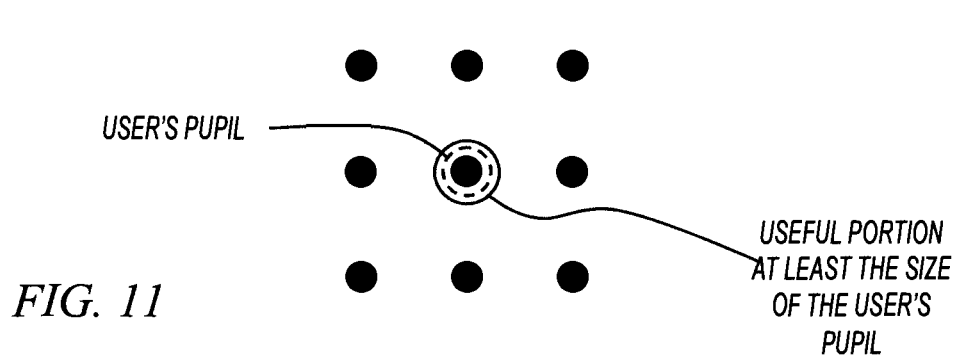

FIGS. 9, 10, and 11 show multiple diffraction orders on an exit pupil plane having a useful portion. Each of FIGS. 9, 10, and 11 show multiple diffraction orders as black dots. The centermost diffraction order is the virtual-scene wave, which includes the information desired to be propagated to the retina. FIG. 9 also shows a schematic representation of the noise beams surrounding the virtual-scene wave. In operation, the noise beams have a finite distribution not shown in the figures.

The ideal useful portion of the exit pupil plane includes all of the virtual-scene wave and nothing else. Pupil filtering works when the user's pupil is substantially aligned with the useful portion of the exit pupil plane such that the virtual-scene wave is allowed to propagate to the retina while everything else is filtered out. In practice, ideal pupil filtering may not always be achieved. For example, in some embodiments, the user's pupil substantially overlaps the useful portion of the exit pupil plane (FIG. 10). These embodiments provide less-than-perfect pupil filtering.

Some embodiments generate a useful portion of the exit pupil plane large enough so that it is at least the size of an expected pupil size. Physically, the minimum pupil width is typically assumed to be 2 mm. However, what is of concern to us is the physical size of the image of the pupil in front of the cornea (i.e., entrance pupil of the eye), which typically has a width slightly greater than 2 mm due to lensing effect at the cornea. Three mm might be a typical minimum value. Hence, some embodiments of the present invention create a useful portion having a width no smaller than about 3 mm. If the width of the useful portion is smaller than 3 mm, some part of the undesired beams may enter through the pupil, degrading the image quality at the retina. Further, some embodiments maintain the amount of average light power that is delivered to the eye above a certain threshold, in order to guarantee that the user's pupil size stays at the lower size limit when the display device is in use.

FIGS. 12-34 show various optical architectures suitable for use in near-to-eye display devices described herein. Some employ transmissive SLMs and some employ reflective SLMs. Some block the real-world views to create a virtual reality, and some superimpose the real-world view on the virtual scene to create an augmented reality. No near-to-eye display device described herein is limited to any one (or any set) of the optical architectures. In general, subsets of each of the optical architectures may be considered as part of an illumination optics module (440, FIG. 4). Further, the optical architectures in many of the figures below are shown for a single eye. In some embodiments, they are replicated to create two sides of a display. Further, in some embodiments, when they are replicated, they are mirrored to provide symmetry.

Figure 12:
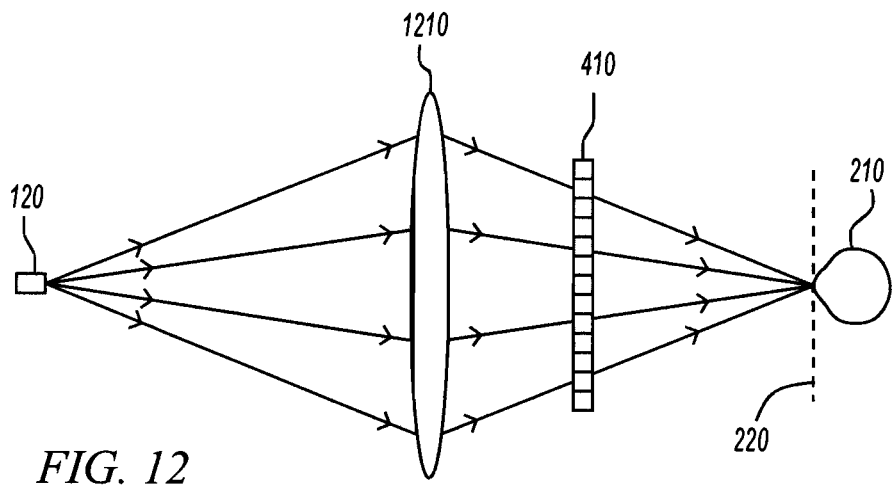
FIG. 12 shows an optical architecture in which the SLM is placed on a converging beam path.

FIG. 12 shows an optical architecture in which the SLM is placed on a converging beam path, where the converging beam is obtained from a point light source 120 by an optical component with a positive refractive power (here shown as a positive lens 1210) placed between the point light source 120 and the transmissive SLM 410. Note that in this architecture, the point light source is actually imaged on the exit pupil plane 220. Therefore, the point light source is optically at a conjugate plane of the exit pupil plane. Also note that the SLM, under the assumption that it is closer to the eye than the normal closest point of the human eye (25 cm), is not at a plane that is conjugate to the retina. One advantage of this architecture is that the directivity patterns of the light waves emerging from each pixel of the SLM are made to almost completely overlap on the exit pupil plane. Thus, wherever the useful portion is located, a uniform light power is intercepted from each pixel of the SLM. In this architecture, the SLM acts as the optical mask that transforms the converging illumination beam to the part of the virtual-scene wave that propagates to and fills the useful portion of the exit pupil plane. The spatial bandwidth requirement of the SLM is directly proportional to the width of the useful portion of the exit pupil plane. In order for the pupil-filtering technique to work, SLM bandwidth must be sufficiently large so that the useful portion is greater than at least the expected minimum size of user's eye pupil. The pixel pitch of the SLM must at least be smaller than the multiplication of the wavelength of light produced by the point light source and the distance between the SLM and the exit pupil plane divided by minimum size of the eye pupil. When the SLM provides only certain type of restricted modulation, a smaller pixel pitch is needed, so that some of the additional SLM bandwidth can be used to distribute the noise beam. If the SLM provides real valued modulation (such as binary amplitude or phase modulation, or intensity modulation), the pixel pitch must be halved, since half of the bandwidth will be occupied by the conjugate beam. In case the SLM generates an unmodulated DC beam, the useful portion can be located at a slightly off axis eye position so that the DC beam can also be filtered by the eye pupil. Finally, the optical component that focuses the diverging light from the point light source to the exit pupil plane, in a practical implementation, might represent a reflective element, such as an elliptical mirror, a spherical mirror, etc. Such a component both acts as a lens and also changes the optical axis.

Figure 13:
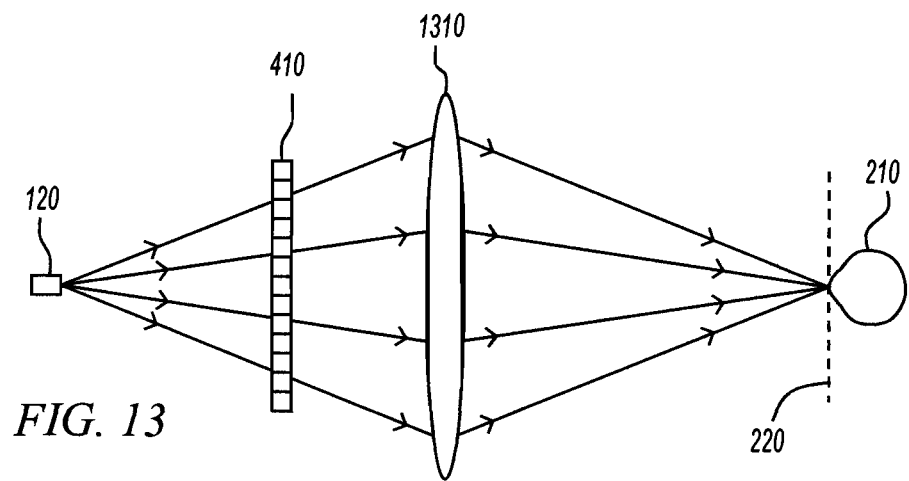
FIG. 13 shows an optical architecture in which the SLM is illuminated by a diverging wavefront.

FIG. 13 shows an optical architecture in which the SLM is illuminated by a diverging wavefront. The light modulated by the SLM, which has an overall diverging character, is then collected by an eyepiece lens 1310 and directed towards the eye. The point light source and the exit pupil plane are again conjugate planes. The SLM might or might not be at a plane that is conjugate to the retina depending on its position. In this architecture, the eyepiece lens basically forms an image of the SLM, which might be virtual or real depending on the position of the SLM. This image of the SLM is referred to herein as the "effective SLM" and it appears to be illuminated by a converging wave. Thus, from the perspective of the effective SLM, the architecture is equivalent to the architecture shown in FIG. 12. Hence, the pupil-filtering technique works if the pixel pitch of the effective SLM is sufficiently small as discussed in FIG. 12. In a practical architecture, a reflective surface, such as an elliptical, spherical, etc. mirror may be the optical equivalent of the eyepiece lens illustrated here. This architecture constitutes a convenient option for designing augmented-reality displays, especially in cases where the SLM is reflective and non-transparent. In such cases, the SLM might be placed on the side of the eyeglass frame, and the light from the SLM can be directed toward the eye by a semitransparent reflective surface, which is the optical equivalent of the eyepiece lens illustrated here. Such architectures are illustrated in subsequent figures.

Figure 14:
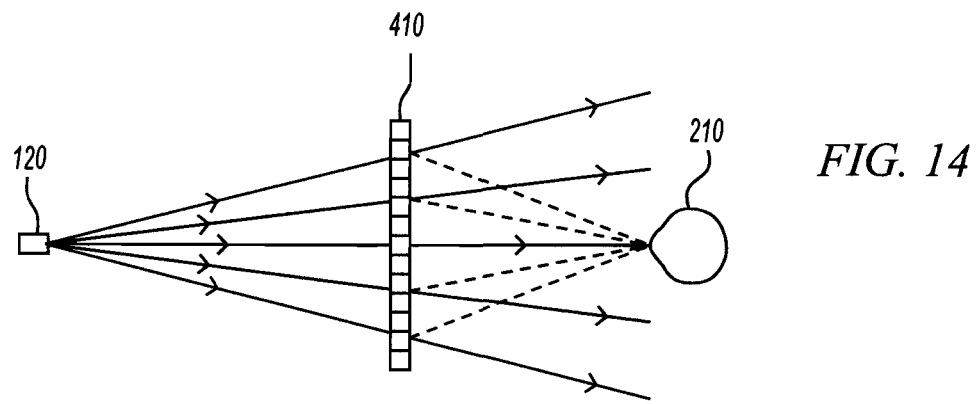
FIG. 14 shows an optical architecture with a point light source and SLM, with no other components with refractive power.

FIG. 14 shows an optical architecture with a point light source and SLM, with no other components with refractive power. In contrast to the previous two cases, the point light source is not at an optical conjugate plane of the exit pupil plane, since it is not imaged on the exit pupil plane. Similarly, the SLM is not at an optical conjugate plane of the retina. The greatest advantage of this architecture is its simplicity, thus the potential for realizing near-to-eye display devices with quite thin form factors, since no components other than the SLM and point light source are present. However, since the SLM is illuminated with diverging light, and the light from the SLM retains its overall diverging character at the exit pupil plane, directivity patterns of light waves from each pixel of the SLM do not overlap on the exit pupil plane. Hence, there is a variation in the power level that is intercepted from each pixel of the SLM, leading to a similar variation on the virtual scene. This variation can partially be reduced during computation of the holographic image to be displayed on the SLM. However, some variation and dark regions will inevitably be present.

Some embodiments use SLMs with lower fill factors. In these embodiments, though there is a loss in light efficiency, the directivity patterns of SLM pixels become uniform, i.e., SLM pixels optically behave closer to isotropic point light sources, and the intensity variation described above no longer exists. Further, in embodiments where the SLM generates an unmodulated DC beam, that beam is not focused to a single spot on the exit pupil plane, but spreads over a large area. Hence, some part of it enters into the useful portion. However, since the energy is spread out, only a little portion of the unmodulated DC beam is intercepted, and the related background noise on the retina is quite low if not perceivable at all.

Figure 15:
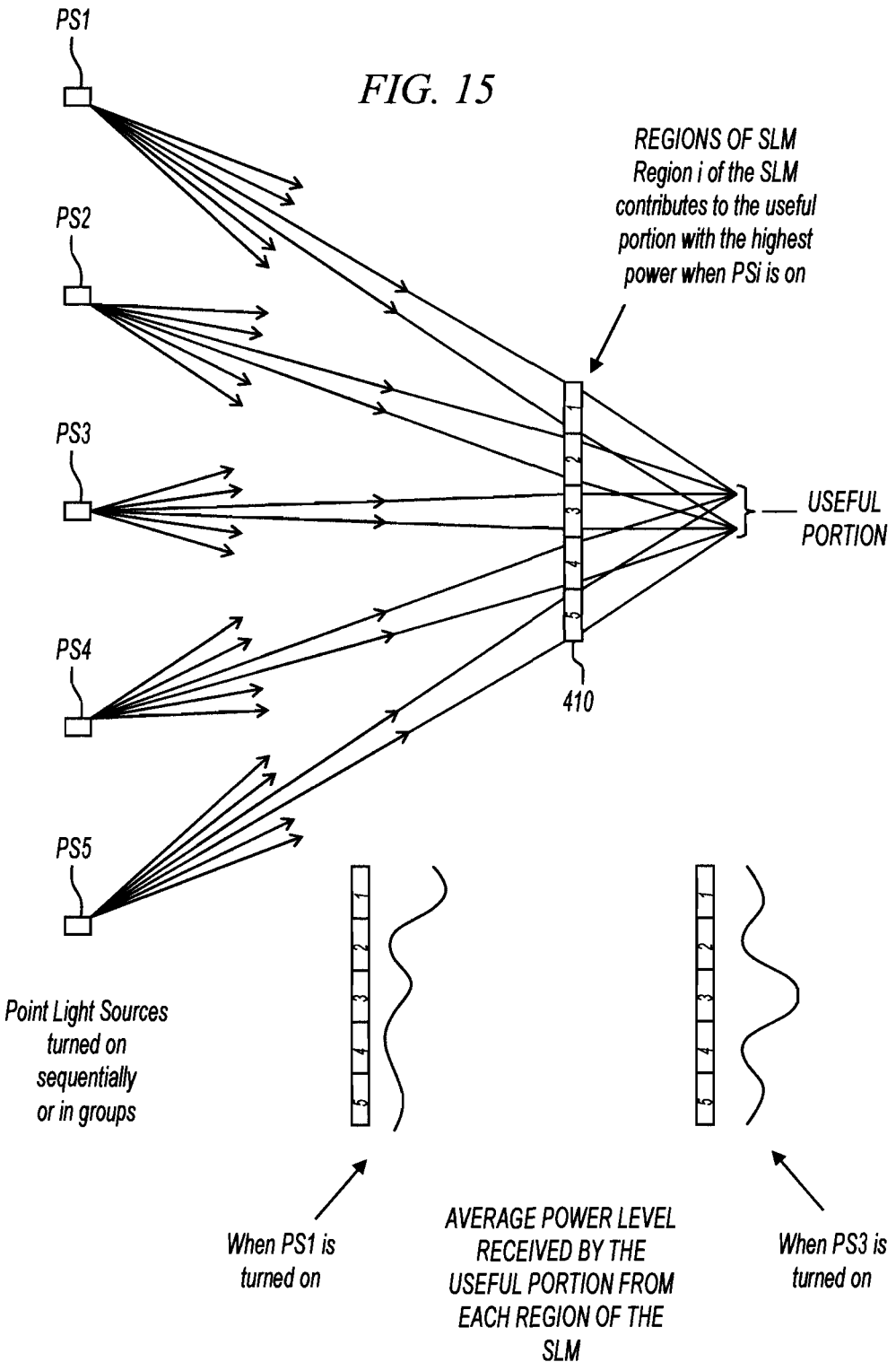
FIG. 15 shows an optical architecture in which an SLM is illuminated in a time sequential manner by an array of point light sources.

FIG. 15 shows an architecture in which an SLM is illuminated in a time sequential manner by an array of point light sources. As an example, five point-light sources PS1 to PS5 are illustrated where PS3 is assumed to be on. When only one of the point light sources is considered, the architecture is the same with the architecture in FIG. 14, and the non-uniform brightness problem discussed in FIG. 14 is present. However, as the point light source that is switched on changes, the part of the SLM that contributes to the useful portion with the highest power changes. Alternatively, the power contributed by a particular section of the SLM to the useful portion changes as the point light source that is turned on changes. In particular, the number and positions of point light sources are arranged such that when time averaged, every part of the SLM sends equal power to the useful portion. Therefore, the point light source array enables us to obtain a uniform variation of brightness in the field of view by time integration of retinal images created by different point light sources. Embodiments represented by FIG. 15 demand a higher frame rate SLM than previously described embodiments. The higher frame rate is driven in synchronism with the point light sources, and the deployment of multiple point light sources. Also, for each point light source, the holographic image on the SLM must be updated according to the new position of the illumination wave. Therefore, multiple holographic images need to be computed for each video frame of the virtual scene.

In general, point light sources should be turned on one at a time only if all light sources significantly illuminate every part of the SLM and no crosstalk at all among reconstructions by different point light sources is tolerable. In some embodiments capable of tolerating some weak level of crosstalk, it is possible to group the light sources and turn each group on at a time. For example, point light sources PS1, PS3, and PS5 may form the first group, and PS2 and PS4 may form the second group. The crosstalk between the point light sources in any of these groups is weak due to the fact there is sufficient separation between the light sources and the light power received from a part of the SLM is dominated by one of the sources. In this way, the demand on SLM frame rate is decreased. Note that in this strategy, the holographic image on each region of the SLM is computed according to the point light source through which the highest power is delivered to the useful portion from that region.

Figure 16:
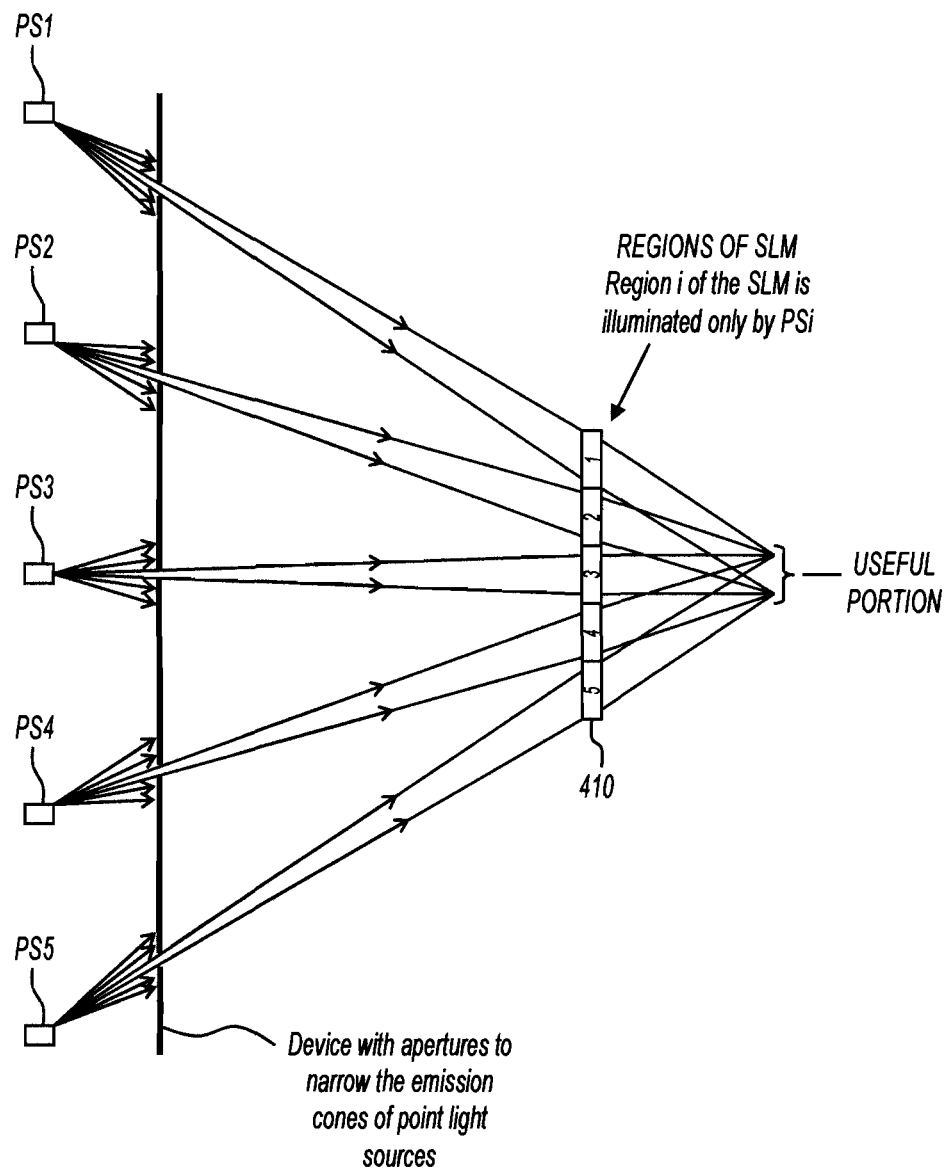
FIG. 16 shows an optical architecture with multiple light sources and apertures to the associated emission cones.

FIG. 16 shows an architecture, which is similar to the architecture illustrated in FIG. 15 with the difference that all point light sources are simultaneously turned on, and the directivity angles of point light sources are constrained, possibly by apertures placed in front of the point light sources. In this architecture, the SLM surface is divided into a number of nonoverlapping regions (labeled 1-5 for example purposes), where each of these regions are essentially illuminated by only one of the point sources. Therefore, the light wave in the useful portion is formed by the superposition of the waves from multiple point light sources. The holographic image on each of the regions of the SLM is computed according to the corresponding light source, and the final holographic image displayed on the SLM is obtained by concatenating these individual holographic images. One advantage of this architecture over the architecture shown in FIG. 15 is that there is no need for a higher frame rate SLM, and the computation of a single holographic image for each video frame is sufficient. One drawback, however, is that the apertures placed in front of the point light sources somewhat increase the bulk of the system. In addition, some diffraction artifacts and corresponding resolution loss will be observed for virtual-scene points that lie close or in the direction of the boundary regions of the SLM that are illuminated by different point light sources.

Some embodiments use a second group of point light sources interspersed with the existing group, such that the second group again divides the SLM surface into non-overlapping regions, but this time with boundaries falling into the middle of the regions formed by the first group of light sources. In these embodiments, the first and second groups of light sources are turned on in a time sequential manner. Object points that lie close to the one set of boundaries might be skipped when the corresponding group of light sources are turned on, and they may be displayed only when the other group of light sources are turned on, with doubled intensity so that average power stays the same. In this way, diffraction artifacts and resolution loss for virtual-scene points that lie close to the boundary regions can be avoided, however, twice a frame rate is demanded from the SLM.

Figure 17:
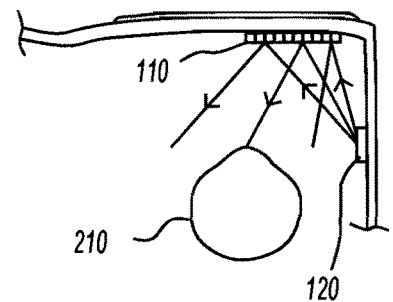
FIG. 17 shows an optical architecture in which a reflective SLM is placed directly in front of the user's eye.

FIG. 17 shows an optical architecture in which a reflective SLM is placed directly in front of the user's eye. In FIG. 17, a reflective SLM 110 is placed directly in front of the eye and is illuminated by a point light source 120 mounted on the side of the eyeglass. The system is optically equivalent to the system depicted in FIG. 14, and constitutes a non-see-through display since the SLM blocks the vision of real world.

Figure 18:
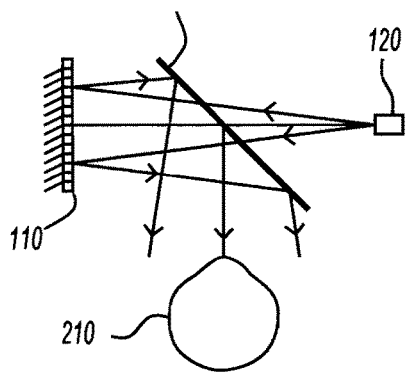
FIGS. 18, 19, and 20 show optical architectures in which real-world vision is not blocked by the SLM.

FIG. 18 shows an architecture in which the SLM is placed such that real-world vision is not blocked. In FIG. 18, a reflective SLM 110 is placed at a position such that real-world vision is not blocked. The SLM is illuminated by a point light source 120 mounted on the side of the eyeglass. The light reflected from the SLM 110 is directed to the user's eye by a beamsplitter 1810. The system is optically equivalent to the system depicted in FIG. 14, and constitutes a see-through display.

Figure 19:
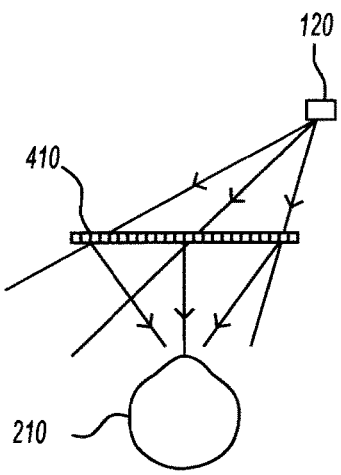

In FIG. 19, a transmissive SLM 410 is placed directly in front of the eye such that real-world vision is not blocked, however, as the real-world light passes through the SLM, the image of the real world might be slightly corrupted. The SLM is illuminated by a point light source 120 mounted on the side of the eyeglass at a location that is further to the eye than the SLM. The system is optically equivalent to the system depicted in FIG. 14, and constitutes a see-through display with some degradation of real-world view.

Figure 20:
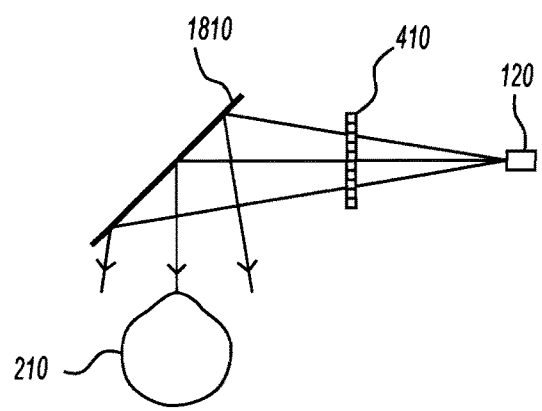

In FIG. 20, a transmissive SLM 410 is placed at a position so that real-world vision is not affected by its presence. The SLM is illuminated by a point light source 120 mounted on the side of the eyeglass. The light transmitted by the SLM is directed to the eye by a beamsplitter 1810. The system is optically equivalent to the system depicted in FIG. 14, and constitutes a see-through display with no degradation of real-world view.

Figure 21:
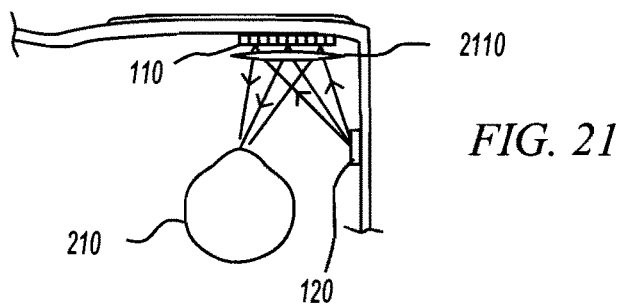
FIG. 21 shows an optical architecture in which a reflective SLM is placed in front of the user's eye.

FIG. 21 shows an optical architecture in which a reflective SLM 110 is placed in front of the user's eye. In FIG. 21, a look at display is implemented with a reflective SLM. A positive lens 2110 is placed in front of the SLM. The focal length of the positive lens is equal to eye relief distance. The lens converts the diverging wave from the point light source 120 to a collimated beam, which hits the SLM with a slight angle, gets modulated and reflected, and passes once again through the same lens which now acts as an eyepiece lens and directs the light towards the pupil. The system is optically equivalent to the system in FIG. 13.

Figure 22:
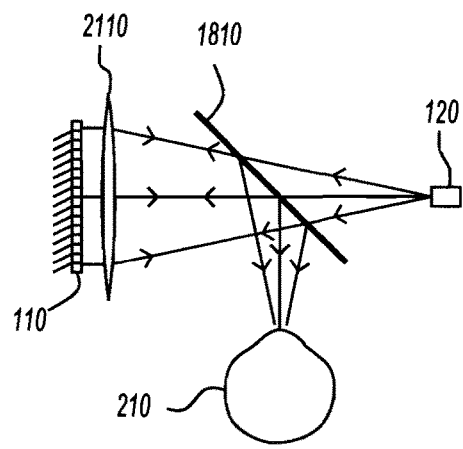
FIGS. 22-28 show optical architectures in which real-world vision is not blocked by the SLM.

FIGS. 22-28 show optical architectures in which real-world vision is not blocked by the SLM. In FIG. 22, the reflective SLM 110 is placed to the side of the eyeglass frame so that the reflective SLM does not block the real-world view. An additional beamsplitter 1810 is used to direct SLM light to the eye pupil of the user. The system is optically equivalent to the system in FIG. 12, and constitutes a see-through display.

Figure 23:
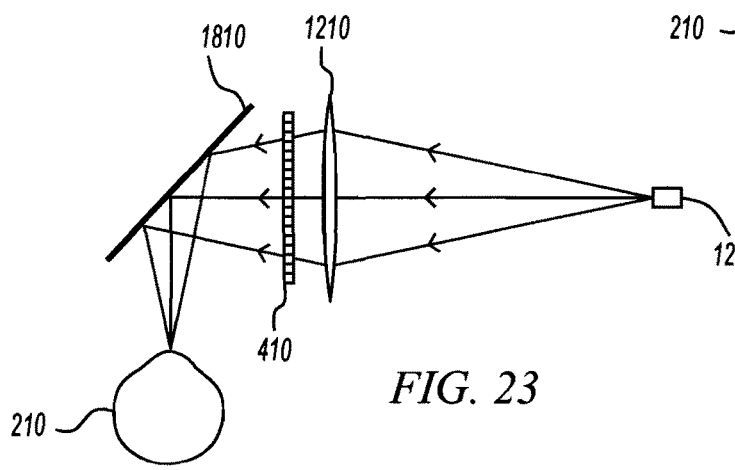

In FIG. 23, a see-through display is implemented with a transmissive SLM 410. The diverging light wave from a point light source 120 is converted to a converging wave by a positive lens 1210. The converging wave passes through the SLM and gets modulated. The SLM wave is directed towards the eye with a beamsplitter 1810. Though the SLM is transmissive, the lens and the SLM are both placed before the beamsplitter so that real-world view is not affected by their presence. The system is optically equivalent to the system in FIG. 12.

Figure 24:
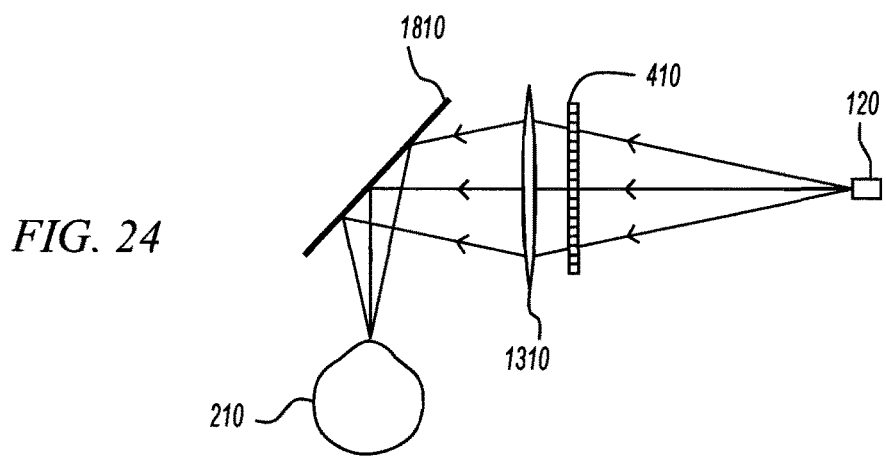

In FIG. 24, a see-through display is implemented with a transmissive SLM. Essentially, the places of the lens and the SLM in FIG. 23 are interchanged. The system is optically equivalent to the system in FIG. 13.

Figure 25:
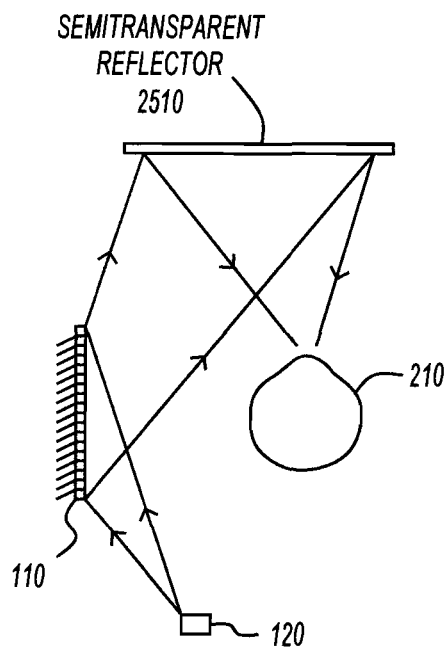

In FIG. 25, a see-through display with a reflective SLM 110 is illustrated. The system is optically equivalent to the system in FIG. 13, where the eyepiece lens is replaced by the semi-transparent reflector 2510 placed in front of the eye. The reflector 2510 can either be a single piece curved component, such as an elliptical or spherical mirror, or it can be a flat component with an array of micromirrors with different tilt angles.

Figure 26:
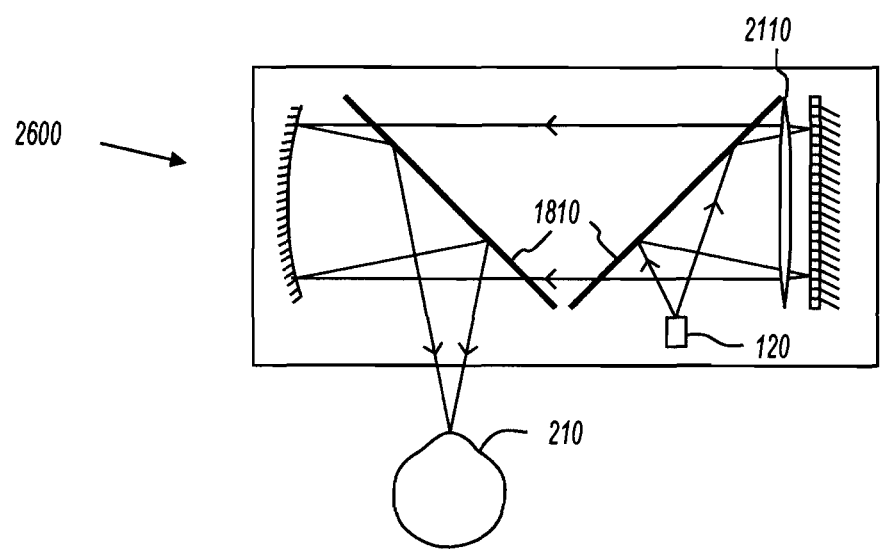

In FIG. 26, a see-through display with a reflective SLM is illustrated. The system is optically equivalent to the system in FIG. 13. The beamsplitter on the right and the lens form a virtual image of the point light source, and SLM is illuminated by a diverging spherical wave which seems to emerge from the said virtual image of the point light source. This wave gets modulated, and then is bent towards the eye pupil with the combination of lens and curved mirror. The architecture is advantageous in that it is compact and provides undistorted see-through vision.

Figure 27:
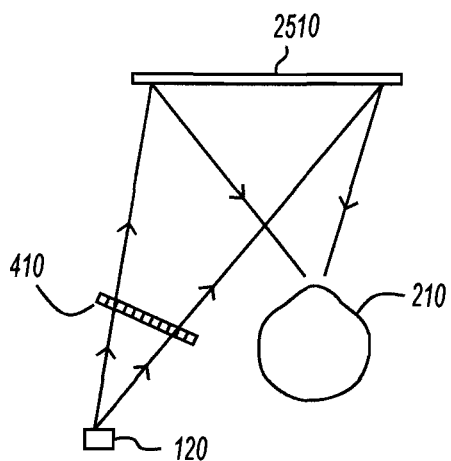

In FIG. 27, a see-through display with a transmissive SLM 410 is illustrated. The system is optically equivalent to the system in FIG. 13 and different from the system in FIG. 25 only in that the SLM is transmissive.

Figure 28:
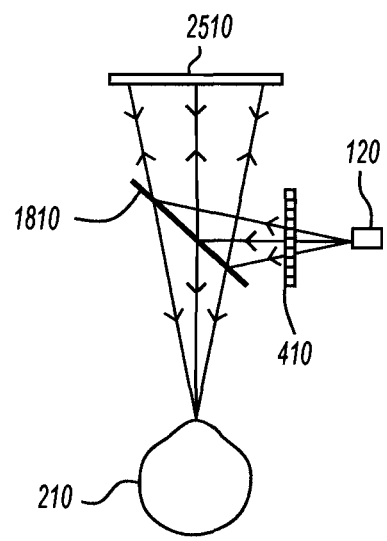

In FIG. 28, a see-through display with a transmissive SLM 410 is illustrated. The system is optically equivalent to the system in FIG. 13 and different from the system in FIG. 27 only in that beamsplitter 1810 is included.

Figure 29:
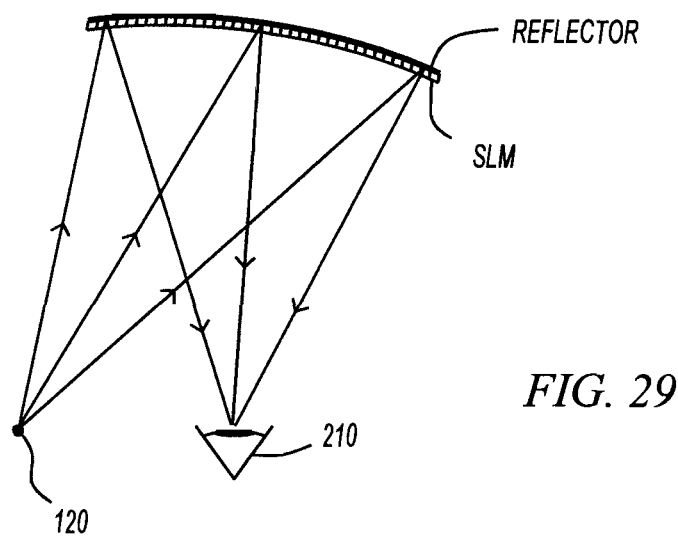
FIG. 29 shows an optical architecture in which an SLM and reflector are combined.

FIG. 29 shows an optical architecture in which an SLM and reflector are combined. As shown in FIG. 29, the SLM is fabricated directly on the semitransparent reflector. The diverging light from the point light source 120 illuminates the SLM, which is directly fabricated on top of a semi-transparent reflector. The SLM-reflector combination can be considered as a single device, which is similar to LCoS SLMs, but fabricated on a transparent substrate. Because the SLM and reflector are essentially a single device, any light ray hitting the SLM also exits the SLM at the same point. The system is optically equivalent to FIG. 13.

Figure 30:
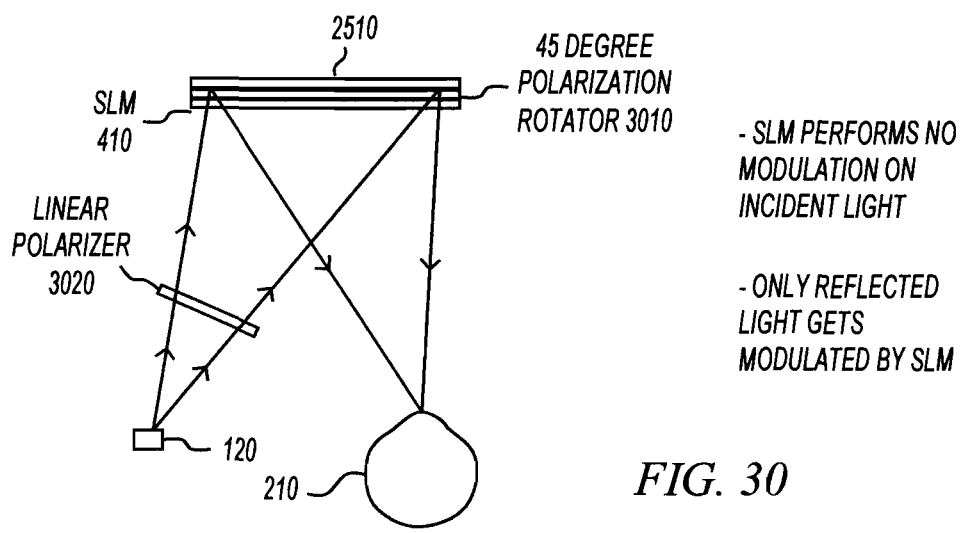
FIG. 30 shows a reflector based solution for modulation in a single direction.

FIG. 30 shows a reflector based solution for modulation in a single direction. FIG. 30 illustrates an embodiment of the invention in which a transmissive SLM 410 is placed between a semi-transparent reflector 2510 and the eye to constitute a see-through display. In some embodiments, the reflector and the SLM are separate devices, with considerable space in between. If the polarizers 3020 and 3010 were not present, the wave emanated from the point light source 120 would get modulated by the transmissive SLM twice: firstly during the initial passage, secondly after getting reflected from the semi-transparent reflector. This double modulation is undesired especially when some of the incident light rays are modulated by different sections of the SLM. In order to eliminate this double modulation, light wave emitted by the point light source is first passed through a polarizer 2920. As the transmissive SLM, a liquid crystal SLM in Parallel Aligned Nematic (PAN) mode may be used, where the LC director axis of the liquid crystal is orthogonal to the axis of the polarizer 3020 that is placed in front of the point light source. Then, the light emanated by the point source does not get modulated by the SLM during the first passage. After passing the SLM, the light wave passes through a 45-degree polarization rotator 3010, then gets reflected from the semi-transparent reflector 2510, and then passes once again through the 45-degree polarization rotator 3010 after which its polarization becomes parallel to the LC director of the SLM. Then the wave enters the SLM once again, and gets modulated this time. In this manner, double modulation is avoided and the incident light wave is modulated by the SLM only during its second passage.

Figure 31:
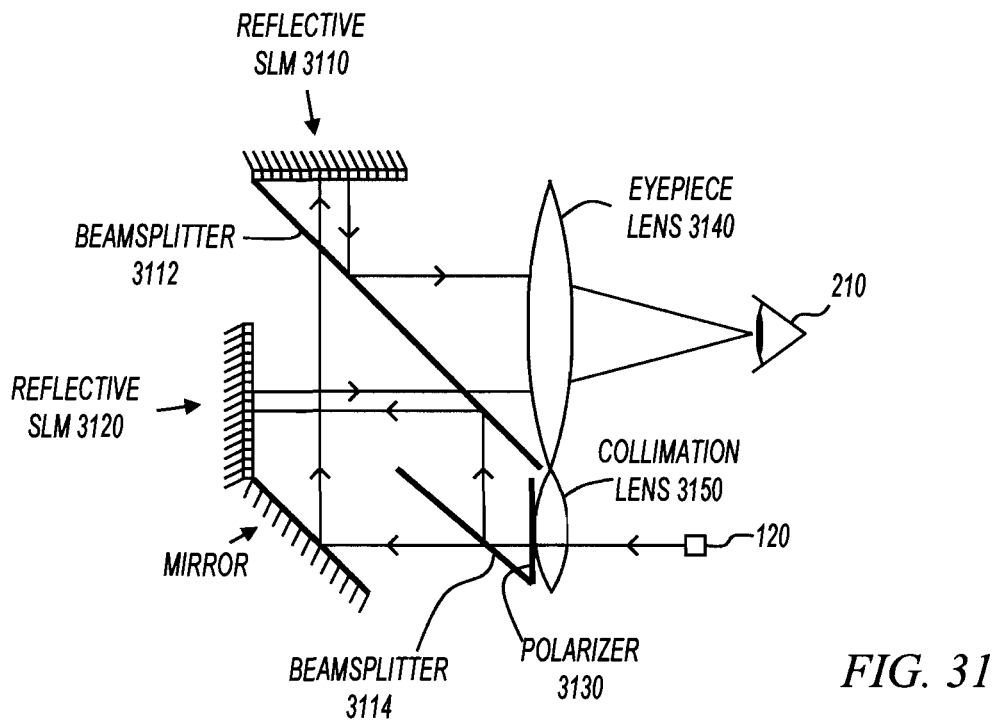
FIG. 31 shows a virtual-reality (VR) architecture with SLM tiling.

FIG. 31 shows a virtual-reality (VR) architecture with SLM tiling. Light from point light source 120 is collimated by collimation lens 3150, passed through a polarizer 3130, and split into two with beamsplitter 3114. One portion is fed to the first reflective SLM 3110, and the other portion is fed to the second reflective SLM 3120. Modulated light coming from the SLMs are joined by beamsplitter 3112 and then passed through a common eyepiece lens 3140 and directed to the eye. The architecture is particularly useful when it is not possible to place SLMs side by side due to their external frames that contain the electronic control circuitry. The SLMs used in the architecture can be identical.

Figure 32:
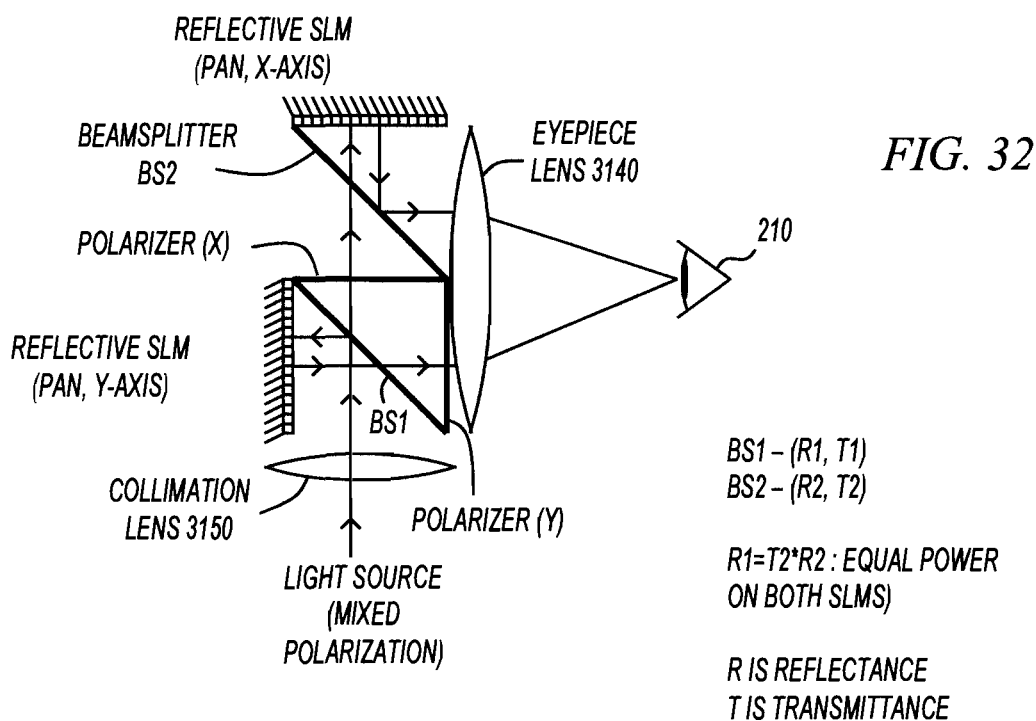
FIG. 32 shows a VR architecture with SLM tiling.

FIG. 32 shows a VR architecture with SLM tiling. This architecture has a smaller form factor than the architecture in FIG. 31, but it requires the LC director axis of the SLMs to be perpendicular to each other. In addition, the R1=T2R2 condition is required so that both SLMs receive equal amount of light power.

Figure 33:
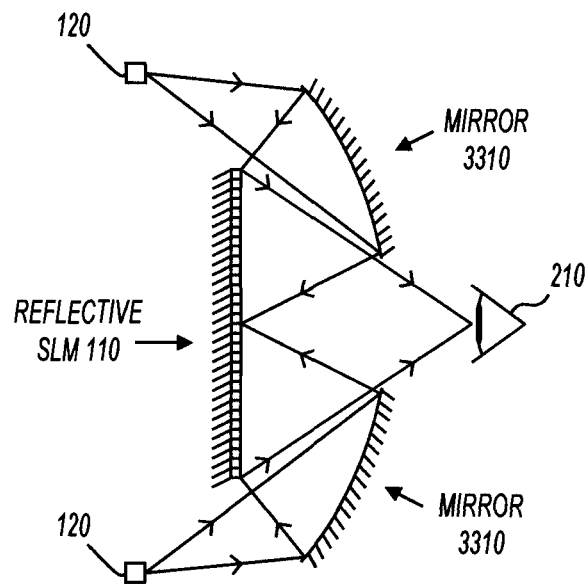
FIG. 33 shows a VR display architecture.

FIG. 33 shows a VR display architecture. A concave mirror 3310, such as used in telescopes, has an opening. The diverging waves emitted by two point-light sources 120 are converted to two pieces of converging waves by the mirror. The converging waves illuminate the reflective SLM 110. The light modulated by the SLM propagates to the exit pupil plane through the opening between the mirrors.

Figure 34:
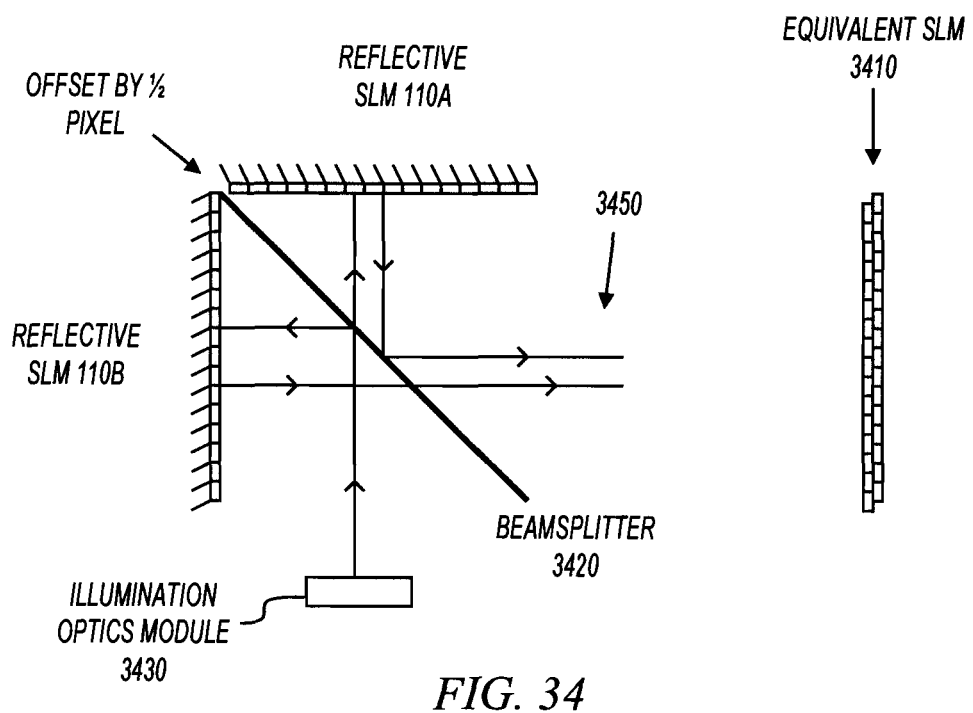
FIG. 34 shows two tiled SLMs to double resolution.

FIG. 34 shows two tiled SLMs to double resolution. Two identical reflective SLMs 110A and 110B are placed facing opposite surfaces of beamsplitter 3420. The SLMs are illuminated by collimated light sent from an illumination optics module 3430. The light emerging at 3450 is equivalent to the light generated by a single SLM that is obtained by adding the complex transmittances of the two SLMs. The SLMs are positioned such that they are offset on the transverse plane by half a pixel pitch with respect to each other during the addition. The equivalent SLM 3410 then has a pixel pitch that is half the pixel pitch of each reflective SLM. The pixel aperture function of the equivalent SLM is the same as the pixel aperture function of the reflective SLM. Since the effective SLM has a higher pixel pitch, its bandwidth and the angular separation between diffraction orders are increased. Such a structure can be used to enlarge the size of the useful portion that can be obtained.

Figure 35:
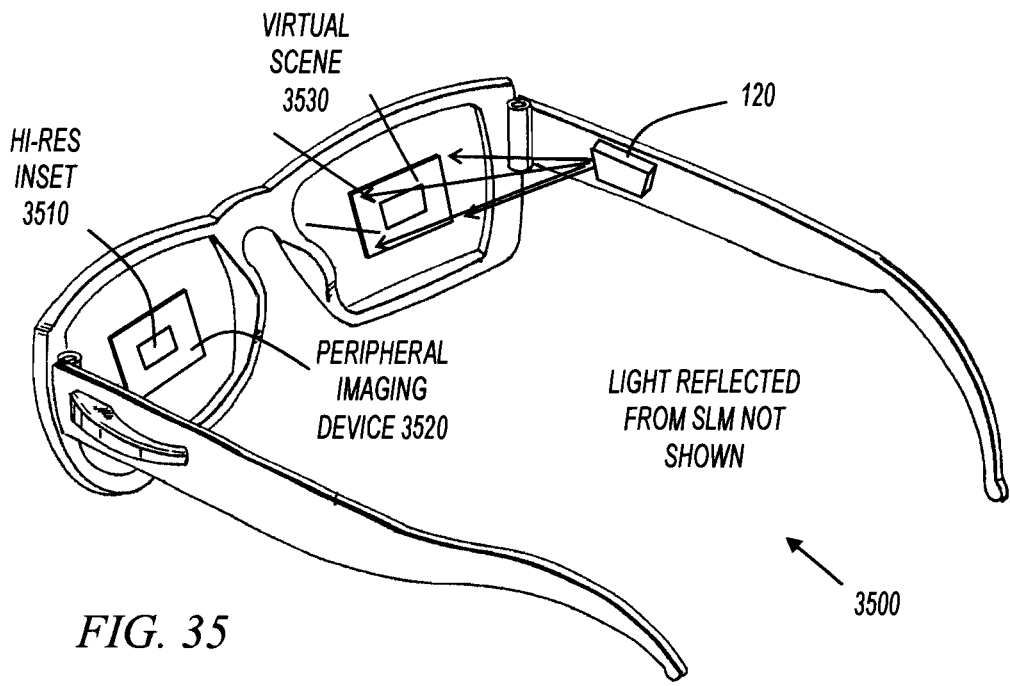
FIG. 35 shows a near-to-eye display device with a high-resolution portion and a low-resolution portion.

FIG. 35 shows a near-to-eye display device with a high-resolution portion and a low-resolution portion. The high-resolution portion is provided by inset 3510 and low-resolution portion is provided by peripheral imaging device 3520. In some embodiments, peripheral imaging device 3520 includes a microdisplay device such as an organic light emitting diode (OLED) display, a liquid crystal display (LCD), or a reflective LCD.

In some embodiments, the high-resolution inset is an SLM that provides a virtual scene to the user as described above. In these embodiments, the SLM has a fixed location and so does the high-resolution inset within the resulting display. In these embodiments, near-to-eye display device 3500 includes an SLM that provides about 30-40 degrees high-resolution central foveal vision with natural depth cues, and a regular 2D display that provides a low-resolution peripheral image. The idea presented here depends on the promise that though the human eyes have a large FOV—around 170 degrees—a very small portion of this FOV (around 6 degrees) constitutes sharp foveal vision at a time. Humans typically enlarge the FOV for sharp foveal vision to about 30-40 degrees by eye motion before resorting to head motion. Therefore, a display that supports a high-quality foveal vision within a FOV of 30-40 degrees, and supplements this with a low-quality peripheral vision will be an economical solution for large FOV designs. The image provided by the SLM carries all natural depth cues in addition to being high resolution. The eye can focus on the virtual objects seen through the SLM as in natural vision. The peripheral image provided by the regular 2D display is not focused on the retina and is low resolution. However, it still establishes a degree of peripheral awareness.

Figure 36:
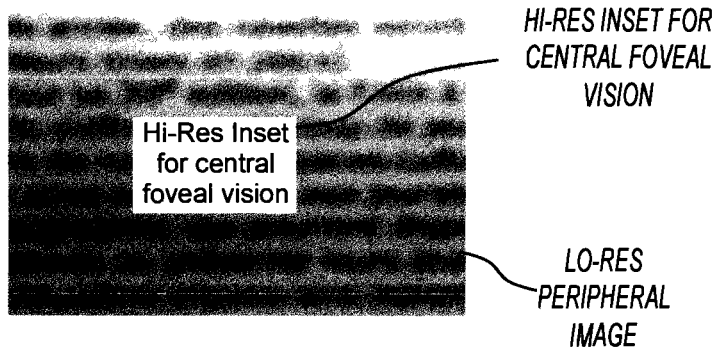
FIG. 36 shows a high-resolution image for foveal vision and lower resolution for peripheral vision.

FIG. 36 shows a high-resolution image for foveal vision and lower resolution for peripheral vision. Image 3600 represents an image seen by a user using near-to-eye display device 3500. The part of the virtual scene that falls in the central-vision part of the FOV appears as a high-resolution image, while the part that falls in the peripheral-vision part appears as a low resolution and defocused image.

Figure 37:
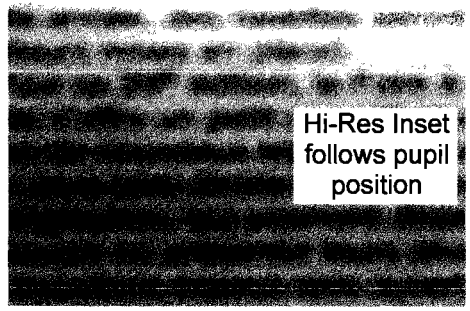
FIG. 37 shows the high-resolution image being steered to a user's pupil position.

FIG. 37 shows the high-resolution image being steered to a user's pupil position. Some embodiments provide for the high-resolution image to be moved within the field of view. Examples of these embodiments are described with reference to figures that follow. Image 3700 represents an image seen by a user when the user's pupil is tracked as the user looks to the right within the FOV. The high-resolution inset is steered to follow the user's eye movement.

Figure 38:
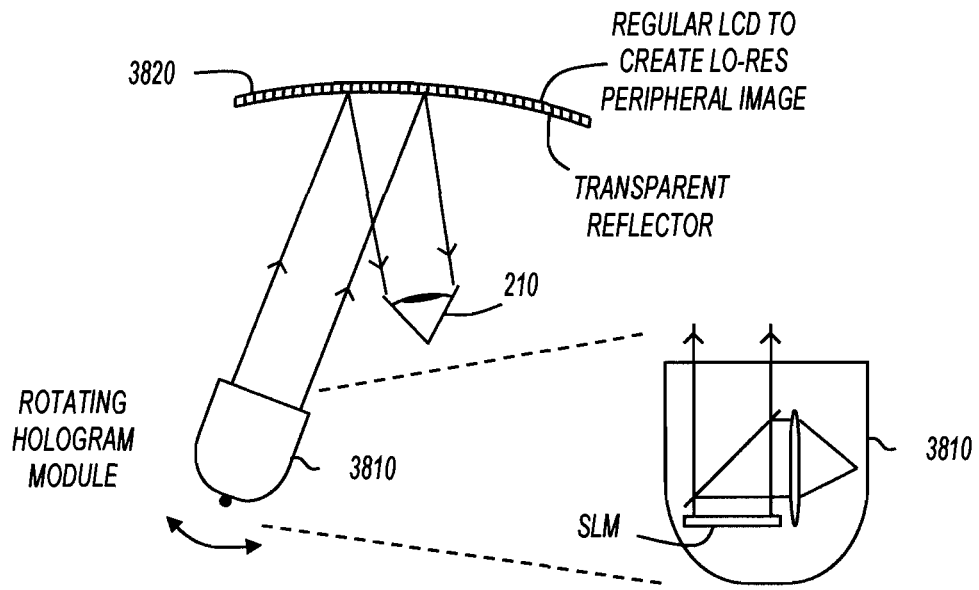
FIGS. 38 and 39 show a display system with a rotating hologram module to create a steerable high-resolution image.
Figure 39:
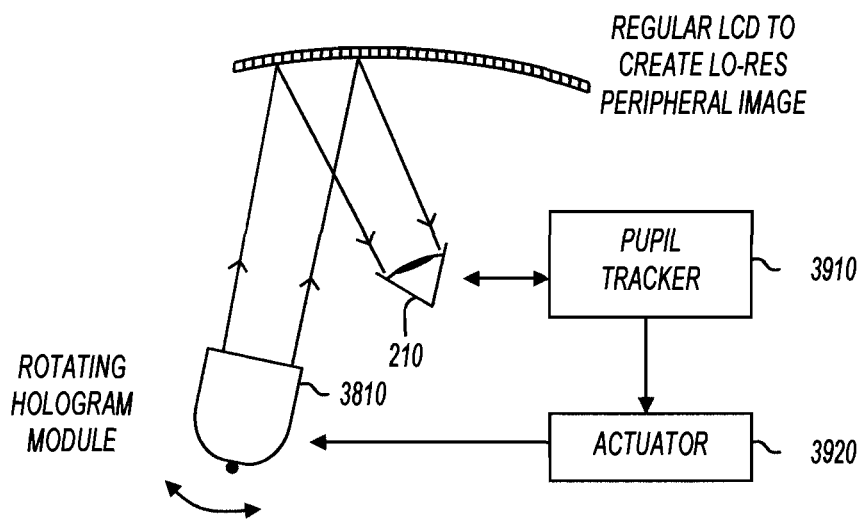

FIGS. 38 and 39 show a display system with a rotating hologram module to create a steerable high-resolution image. In some embodiments represented by FIGS. 38 and 39, only the 6-10 degree portion of the FOV is provided by the SLM at a single time. In other embodiments, more than 6-10 degrees is provided at a time. The rest of the FOV is covered by a regular 2D display. Pupil movements of the user are tracked, and the hologram module 3810 is rotated based on those movements to steer the SLM light towards the pupil. Part of the 2D display image that lies within the central-vision region is temporarily blackened, so that the central vision is formed only by the SLM and thus is high resolution. The reflector is designed such that the SLM light is directed towards the eye pupil for any position of the eye pupil.

Rotating hologram module 3810 is shown with an SLM, lens, beamsplitter, and light source. Any of the optical architectures described herein may be employed within rotating hologram module 3810 without departing from the scope of the present invention.

In some embodiments, LCD 3820 is used as peripheral imaging device 3520 (FIG. 35), and rotating hologram module 3810 illuminates a portion of LCD 3820 to create the high-resolution inset 3510 (FIG. 35). Rotating hologram module 3810 may be physically location on the frame of near-to-eye display device 35. For example, rotating hologram module 3810 may be co-located with a point light source 120.

FIG. 39 shows pupil tracker 3910 tracking movement of the user's eye 210 and actuator 3920 used to rotate rotating hologram module 3810. When the user moves eye 210, pupil tracker 3910 sends a signal to actuator 3920 to cause the hologram module to rotate. Pupil tracker 3910 may include any suitable components capable of performing as described. For example, pupil tracker 3910 may include one or more cameras, one more light sources (e.g., infrared), and a processing element to interpret the pupil-tracking data and to command actuator 3920. Actuator 3920 may include any type of component capable of performing as described. For example, actuator 3920 may be a stepper motor or series of stepper motors coupled to rotating hologram module 3810.

Figure 40:
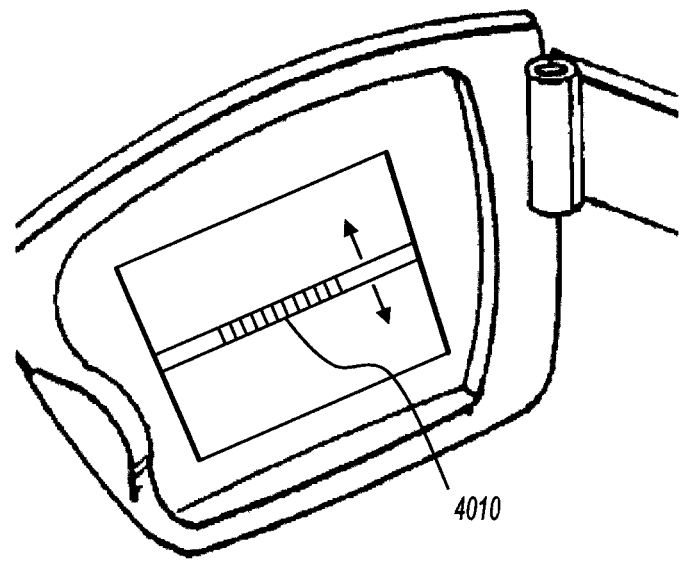
FIG. 40 shows a portion of a near-to-eye display device having a moving platform.

FIG. 40 shows a portion of a near-to-eye display device having a moving platform. Moving platform 4010 moves within the field of view of the user. Moving platform 4010 is actuated by circuits (not shown) mounted on the near-to-eye display device, or connected to the near-to-eye display device with cabling or wirelessly. In some embodiments, moving platform includes light sources and/or SLMs. In these embodiments, the light sources and/or SLMs are driven by circuits (not shown) mounted on the near-to-eye display device, or connected to the near-to-eye display device with cabling or wirelessly. Various embodiments of moving platforms are now described.

Figure 41:
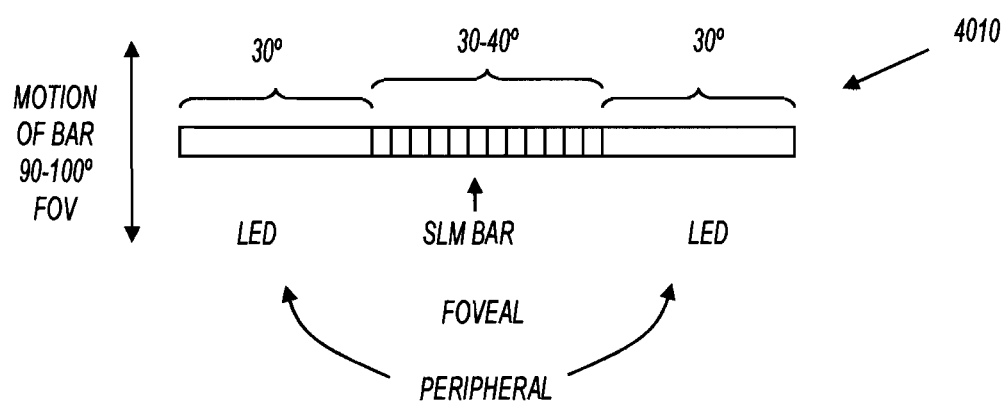
FIG. 41 shows a moving platform upon which an SLM is mounted.

FIG. 41 shows a moving platform upon which an SLM bar that covers about 30-40 degrees of central FOV is mounted, along with two LED bars each of which covers about 30 degrees of peripheral FOV. The SLM bar includes a plurality of pixels, the spacing of which satisfies the criteria described herein with respect to the useful portion of the exit pupil plane. The LED bars may include any number of pixels. In some embodiments, the resolution of the LED bars is less than the resolution of the SLM bar. The entire platform 4010 can move up and down periodically to scan the vertical direction. The display is considered see-through since the moving platform does not continuously block any part of the user's FOV, but does so only for a short duration of time. Both the SLM bar and the LED bar have high refresh rates.

Figure 42:
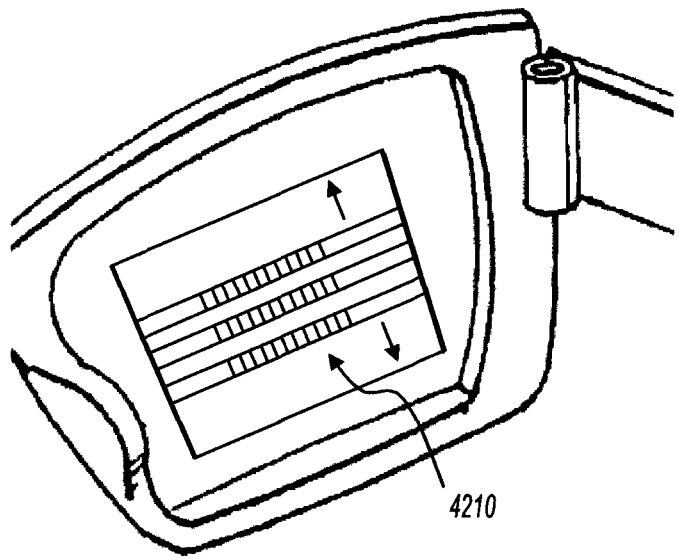
FIG. 42 shows a portion of a near-to-eye display device having a moving platform with an array of bars.

FIG. 42 shows a portion of a near-to-eye display device having a moving platform with an array of bars. Moving platform 4210 includes more than one bar that moves up and down in the vertical direction to fill the FOV. Moving platforms that include a plurality of bars, such as platform

4210 are also referred to herein as "slotted platforms." Moving platform 4210 is actuated synchronously with the SLM data being driven on the various SLM elements on moving bar 4210. The idea is similar to FIG. 40, except for the fact that an array of bars are used so that each of the bars needs to scan a smaller vertical range, relieving the framerate constraint on the SLM bar and LED bar.

Portions of moving platform 4210 are considered to include a microdisplay. For example, the portions of bars 4010 that include LEDs and the LED bars above and below bars 4010 constitute a microdisplay. In some embodiments, microdisplays on moving bars have a lower resolution than SLM bars. Also in some embodiments, microdisplays on moving bars have a greater pixel pitch than SLM bars.

Figure 43:
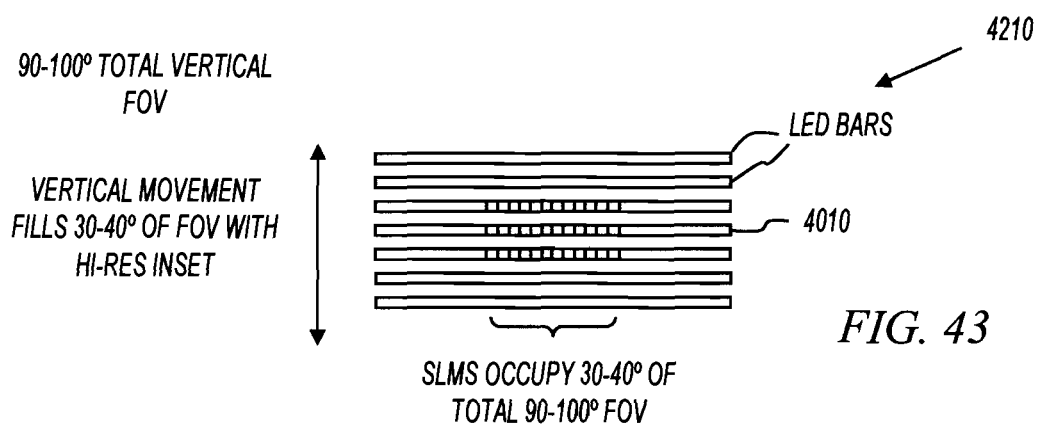
FIG. 43 shows a moving platform having an array of bars upon which SLMs and microdisplays are mounted.

FIG. 43 shows a moving platform having an array of bars upon which SLMs and microdisplays are mounted. Moving platform 4210 includes a plurality of bars equivalent to 4010, and a plurality of bars that only include LEDs. The SLM bar is mounted only on the bars in the middle so that 30-40 degrees of FOV is covered in the vertical direction as well. The top and bottom bars only consist of LEDs, since they are not responsible for central foveal vision but only peripheral vision.

Figure 44:
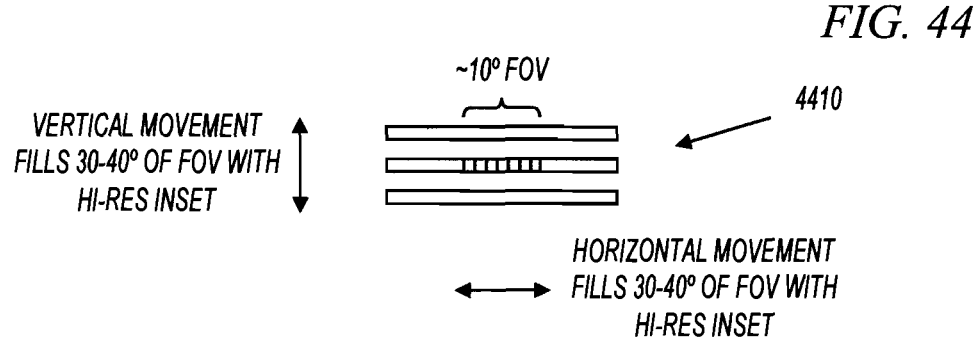
FIG. 44 shows a moving platform that moves in two dimensions to increase resolution.

FIG. 44 shows an even simpler design where only a small SLM is mounted on the middle bar for central vision, while two more LED bars are placed to provide peripheral vision. At a single time, the SLM bar only covers about 6-7 degrees of horizontal FOV. For a fixed position of eye pupil, the bar only scans in the vertical direction to cover 6-7 degrees of vertical FOV as well. When the eye pupil moves, the SLM bar also moves in the horizontal direction to cover the portion of the FOV for central vision. In some embodiments, all bars shown move as described, and in other embodiments, only the middle bar with the SLM moves as described.

Figure 45:
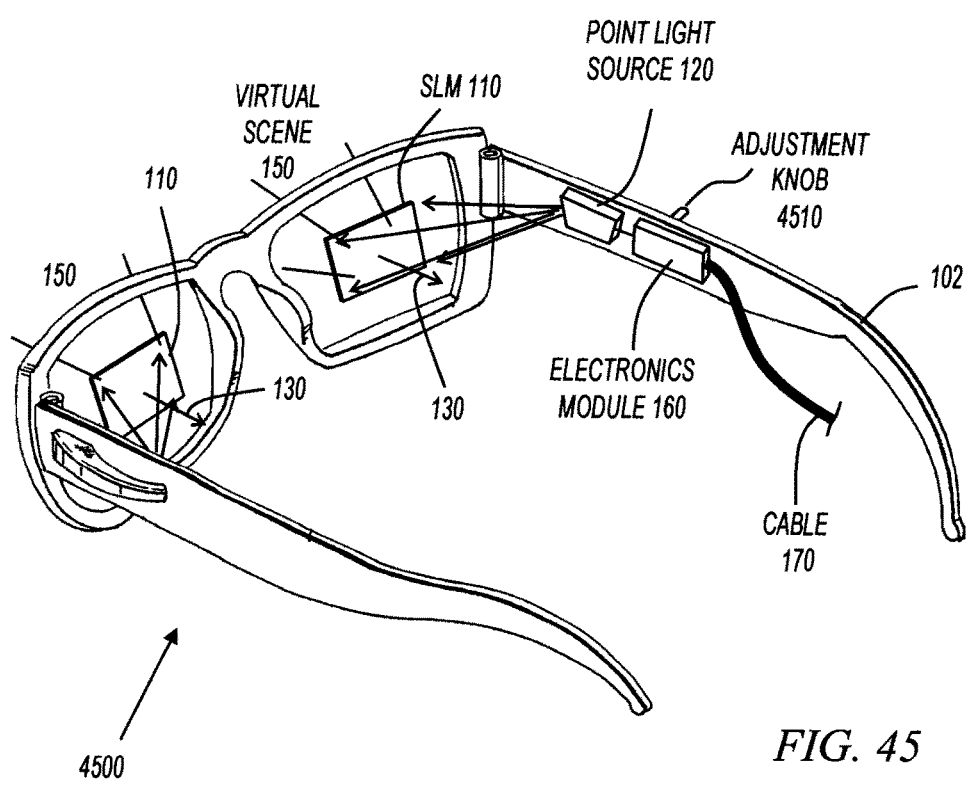
FIG. 45 shows a near-to-eye display device with a transducer to interact with a user for calibration.

FIG. 45 shows a near-to-eye display device with a transducer to interact with a user for calibration. Near-to-eye display device 4500 is similar to near-to-eye display device 100 (FIG. 1) with the addition of adjustment knob 4510. Adjustment knob 4510 is an example of a transducer that allows the user to interact with the near-to-eye display device. For example, in some embodiments, near-to-eye display device 4510 may perform calibration actions in which the user is asked to provide feedback using the transducer. Various calibration embodiments are now described.

FIGS. 46, 48, 50, and 52 show flowcharts of calibration methods in accordance with various embodiments of the present invention. In some embodiments, these methods, or portions thereof, are performed by a near-to-eye display device, embodiments of which are shown in, and described with reference to, the figures of this disclosure. In other embodiments, these methods are performed by a computer or an electronic system. The various calibration methods are not limited by the particular type of apparatus performing the method. Further the disclosed actions in the calibration methods may be performed in the order presented, or may be performed in a different order. Also, in some embodiments, some actions listed in the figures are omitted while performing method embodiments.

Figure 46:
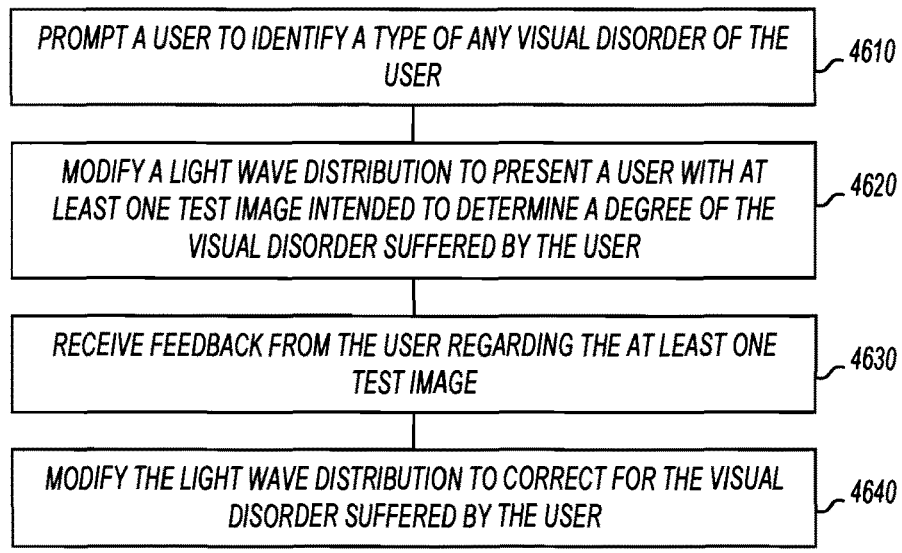
FIG. 46 shows a flowchart of calibration methods in accordance with various embodiments of the invention.
Figure 47:
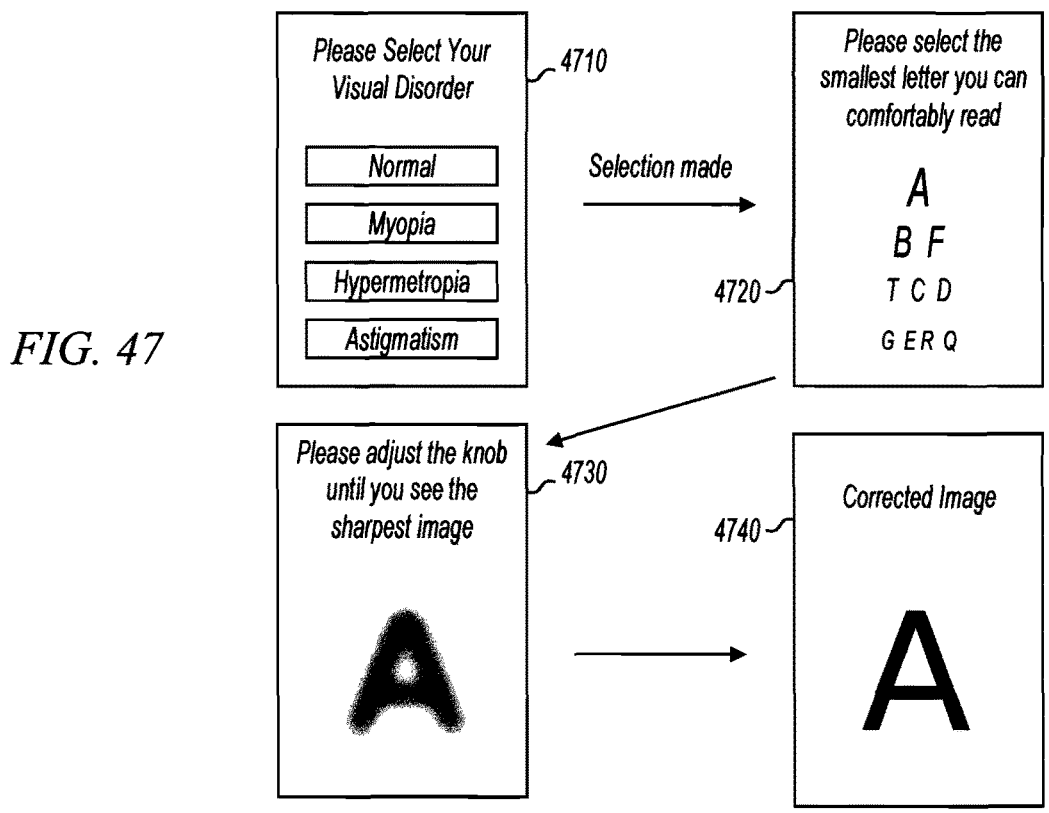
FIG. 47 shows example images shown to a user during calibration.

In calibration embodiments according to FIG. 46, a user is prompted to identify a type of any visual disorder. An example image to prompt a user is shown at 4710 (FIG. 47). Once the user has entered a type of disorder, the near-to-eye display device may display a chart from which the user may make a selection. For example, in the example execution of the method shown in FIG. 47, the user has selected myopia, and the system presents a chart prompting the user to select the smallest letter the user can comfortably read. In some embodiments, a user may make a selection by looking at it, in which case built in pupil-tracking hardware can interpret the selection. In other embodiments, a user may interact with a transducer, such as adjustment knob 4510 (FIG. 45) to make the selection, and in still further embodiments, a user may interact with a touch-sensitive portion of the display area on the near-to-eye display device.

At 4620, a light wave distribution is modified to present the user with at least one test image intended to determine a degree of the visual disorder suffered by the user. For example, in some embodiments, a single image such as that shown at 4730 (FIG. 47) is shown to the user. In other embodiments, multiple images such as those shown at 4920 (FIG. 9) are shown to the user.

At 4630, feedback is received from the user regarding the at least one test image. In some embodiments, this corresponds to a user selecting an image using a transducer. In other embodiments, this corresponds to a user turning an adjustment knob. For example, as a user interacts with adjustment knob, the image at 4730 may be focused at different distances until the user's myopia has been overcome.

At 4640, the light wave distribution is modified to correct for the visual disorder suffered by the user. This is shown at 4740 (FIG. 47). The different images displayed are generated using an SLM as described above. Visual disorders may be corrected using the computation of the SLM data. Computation of SLM data is described further below.

Figure 48:
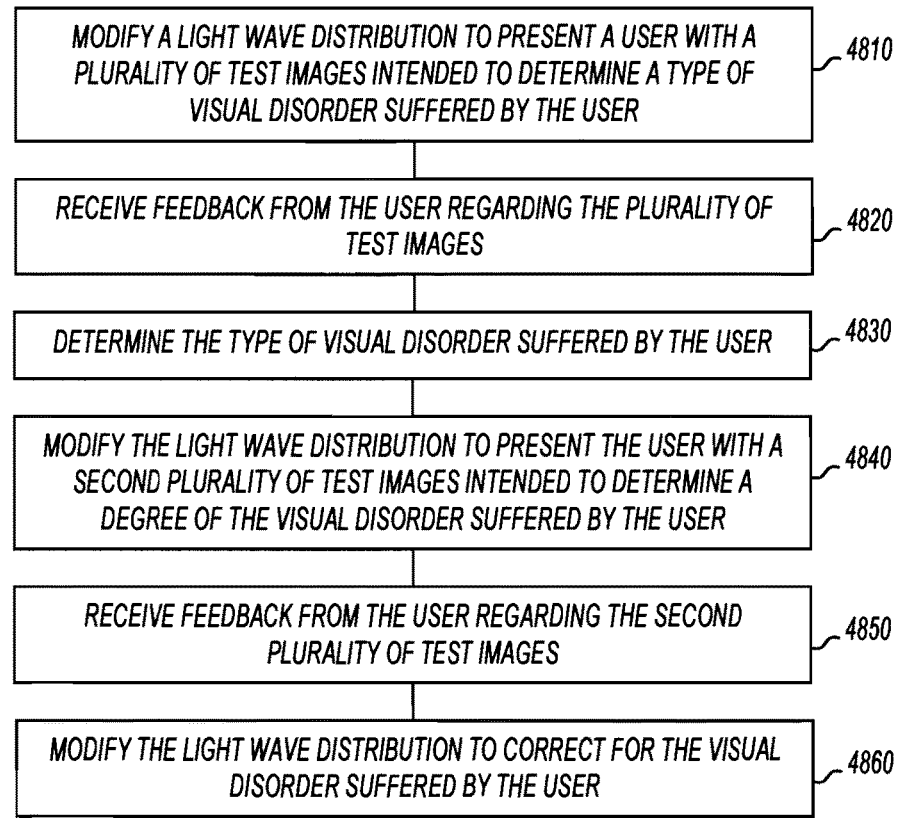
FIG. 48 shows a flowchart of calibration methods in accordance with various embodiments of the invention.

In calibration embodiments according to FIG. 48, a light wave distribution is modified to present the user with a plurality of test images intended to determine a type of visual disorder (if any) suffered by the user. For example, in some embodiments, images such as that shown at 4910 (FIG. 49) are shown to the user. At 4820, feedback is received from the user regarding the plurality of test images. In some embodiments, this corresponds to a user selecting an image using a transducer. In other embodiments, this corresponds to a user turning an adjustment knob. In still further embodiments, this corresponds to a user interacting with a touch-sensitive portion of the display.

At 4830, the type of visual disorder suffered by the user is determined based on the feedback received. In the example execution of the method shown in FIG. 49, the user has selected an image corresponding to myopia.

At 4840, the light wave distribution is modified to present the user with a second plurality of test images intended to determine a degree of the visual disorder suffered by the user. For example, in some embodiments, multiple images such as those shown at 4920 (FIG. 9) are shown to the user.

At 4850, additional feedback is received from the user regarding the second plurality of test images. In some embodiments, this corresponds to a user selecting an image using a transducer. In other embodiments, this corresponds to a user turning an adjustment knob or interacting with a touch-sensitive display. In some embodiments, 4840 and 4850 are performed more than once to determine the proper correction to be applied to correct the user's visual disorder.

Figure 49:
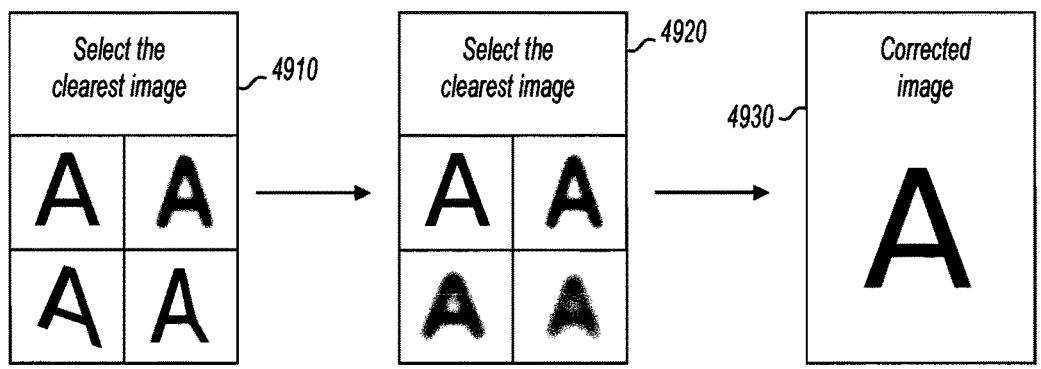
FIG. 49 shows example images shown to a user during calibration.

At 4860, the light wave distribution is modified to correct for the visual disorder suffered by the user. This is shown at 4930 (FIG. 49). The different images displayed are generated using an SLM as described above. Visual disorders may be corrected using the computation of the SLM data. Computation of SLM data is described further below.

Figure 50:
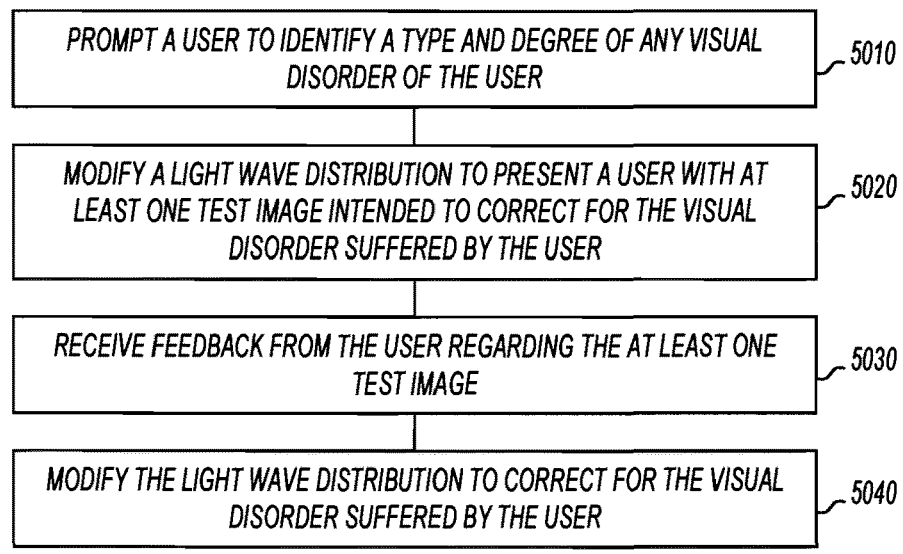
FIG. 50 shows a flowchart of calibration methods in accordance with various embodiments of the invention.
Figure 51:
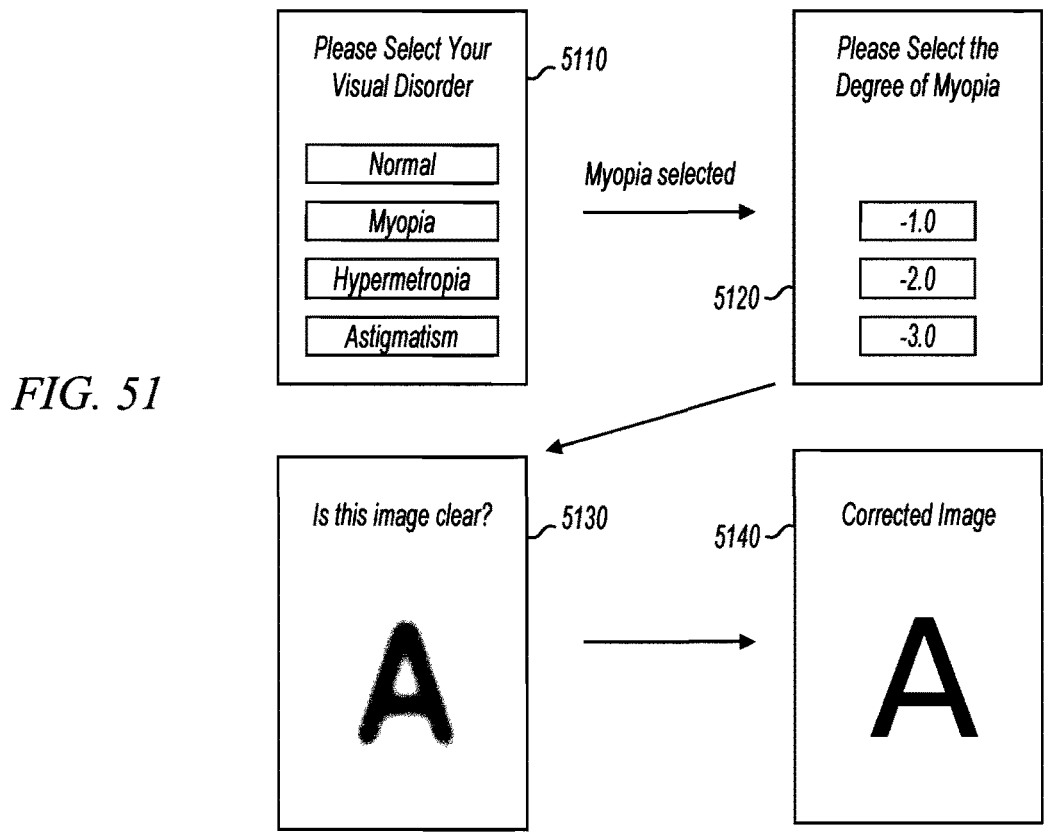
FIG. 51 shows example images shown to a user during calibration.

In calibration embodiments according to FIG. 50, the user is prompted to enter the type and degree of the visual disorder at 5010. Example images to prompt a user are shown at 5110 and 5120 (FIG. 51). Once the user has entered the type and degree of disorder, the near-to-eye display device modifies a light wave distribution to present the user with at least one test image intended to correct for the visual disorder suffered by the user at 5020. This is shown at 5130.

At 5030, feedback is received from the user regarding the at least one test image. In some embodiments, this corresponds to a user selecting an image using a transducer. In other embodiments, this corresponds to a user turning an adjustment knob or interacting with a touch-sensitive display. For example, as a user interacts with adjustment knob, the image at 5130 may be focused at different distances until the user's myopia has been overcome At 5040, the light wave distribution is modified to correct for the visual disorder suffered by the user. This is shown at 5140 (FIG. 51). The different images displayed are generated using an SLM as described above. Visual disorders may be corrected using the computation of the SLM data. Computation of SLM data is described further below.

In some embodiments, user profiles are stored within the near-to-eye display device for later retrieval. Also in some embodiments, the calibration methods described also provide actions to allow for brightness, contrast, and color correction. Any type of visual setting may be applied and any type image enhancement may be incorporated without departing from the scope of the present invention.

Figure 52:
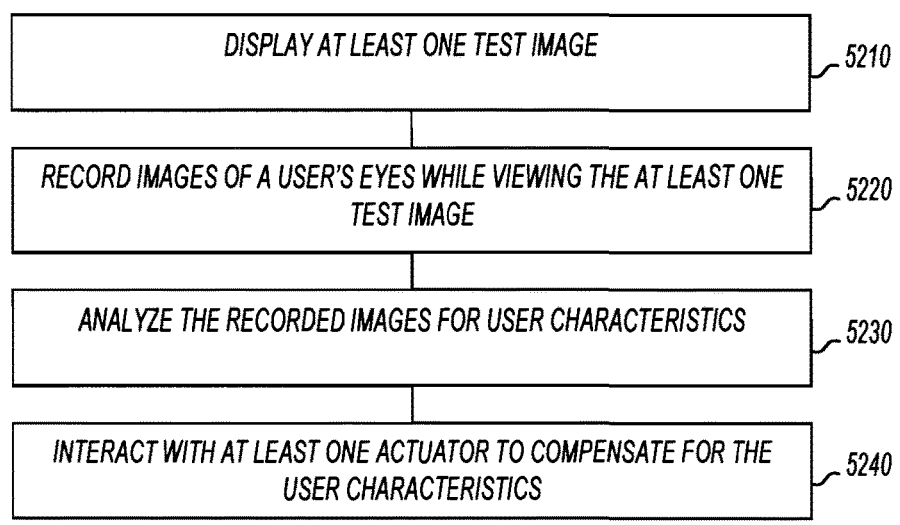
FIG. 52 shows a flowchart of calibration methods in accordance with various embodiments of the invention.

FIG. 52 shows a flowchart of calibration methods in accordance with various embodiments of the invention. Methods represented by FIG. 52 differ from the previously described calibration methods in that methods represented by FIG. 52 interact with one or more actuators on the near-to-eye display device to correct for anomalies.

Figure 53:
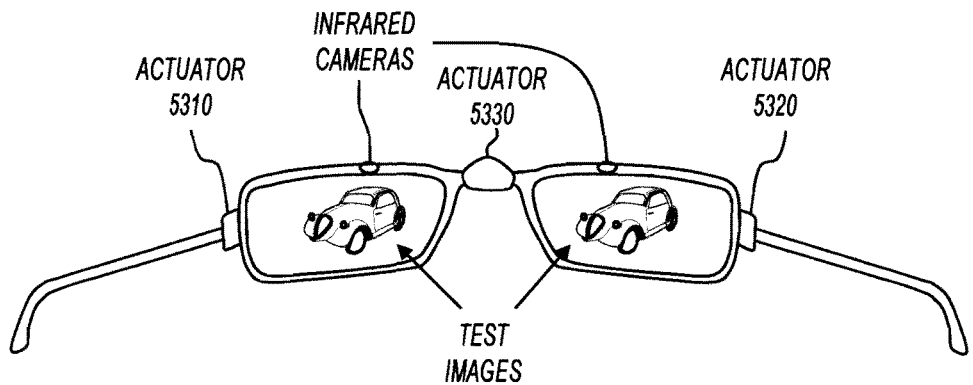
FIG. 53 shows a near-to-eye display device with actuators for calibration.

At 5210, at least one test image is displayed. This is shown in FIG. 53. Note that in all calibration embodiments, test images are not actually displayed on an eyeglass lens, but rather, test images are made to be part of a virtual scene using the SLM and pupil-filtering methods described above.

Figure 54:
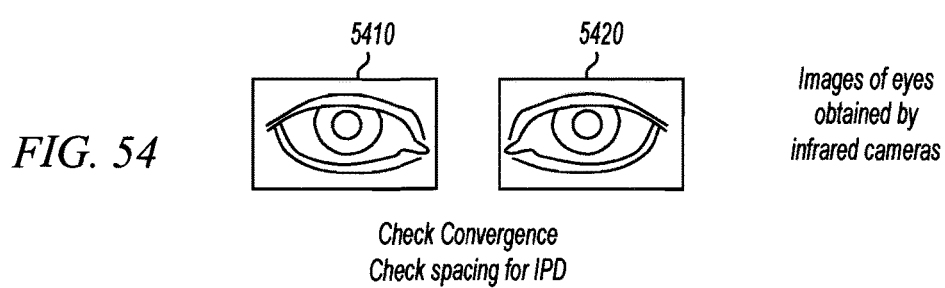
FIG. 54 shows images of a user's eyes used for calibration.

In some embodiments, the user is shown multiple test images that are at different depths and transverse positions. During this procedure, two cameras (that are mounted on the HWD and well calibrated with respect to each other) may record the position of her pupils at 5220. As shown in FIG. 53, the cameras may be infrared cameras. Example images that may be recorded are shown in FIG. 54.

At 5230, the recorded images are analyzed for user characteristics such as interpupil distance (IPD), and convergence when viewing 3D images. For example, images of the eyes captured by the cameras may be analyzed to determine the convergence points of the eyes. In some embodiments, the images from the infrared cameras are processed to precisely understand the eye relief distance, orientation of the display with respect to the head and eyes of the user, inter pupillary distance of the user, etc. In particular, the sizes of the iris, limbus, and locations of and distances between Purkinje images (images of infrared light sources generated by reflections from different layers of user's eye) are detected and analyzed to get the best prediction about the values of the relative positional parameters between the eyeglass and the user's eyes.

Figure 55:
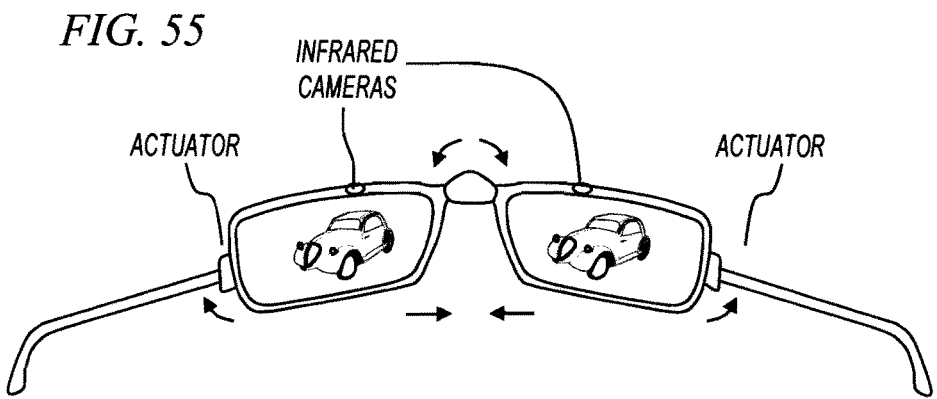
FIG. 55 shows the near-to-eye display device of FIG. 53 with actuation for calibration.

Based on this information, the near-to-eye display device may cause the actuators 5310, 5320, and 5330 to change physical characteristics of the device to accommodate a user's physical characteristics. For example, the near-to-eye display device may adjust SLM position, position of light sources, distance between the two SLMs, and the like. Examples are shown in FIG. 55.

The various embodiments of the present invention provide for precise calibration between left and right display units, which enables correct and comfortable 3D vision. Once the display is calibrated for a user, she can save the parameters in a user profile stored in the system. When she wears the display the next time—after another user—she can select her own profile. In this way, the display can be shared by multiple users in a convenient manner.

Further, when a user wears the display, the cameras may take a quick photo of the eyes, and use iris-recognition algorithms to recognize a user who used the display before. Then, automatic re-calibration of the display for that user can be performed.

Figure 56:
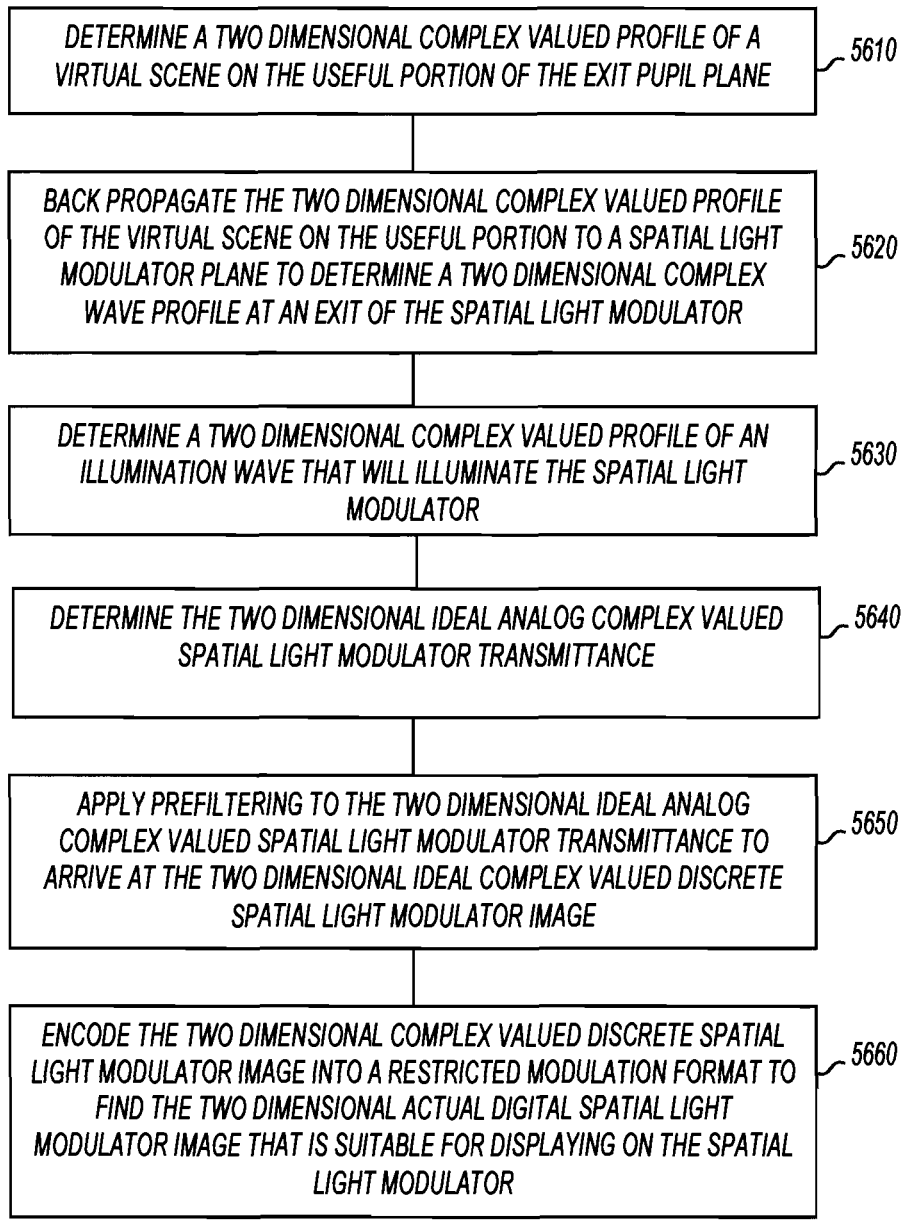
FIG. 56 shows a flowchart representing computation of SLM data.

FIG. 56 shows a flowchart representing computation of SLM data. In some embodiments, method 5600, or portions thereof, is performed by a near-to-eye display device, embodiments of which are shown in previous figures. In other embodiments, method 5600 is performed by a computer or an electronic system. Method 5600 is not limited by the particular type of apparatus performing the method. The various actions in method 5600 may be performed in the order presented, or may be performed in a different order. Further, in some embodiments, some actions listed in FIG. 56 are omitted from method 5600.

As described previously, in various embodiments of the present invention, the display system delivers, to the useful portion, the light wave that would be generated by a virtual scene. In particular, an SLM is the component through which the information about the virtual scene is imposed on the light waves generated by the light source or sources within the display. Therefore, the SLM transforms the non-information-bearing wave illuminating it to the information-bearing wave part of which is delivered to the useful portion. Under this view, the main computational steps to determine SLM data for a frame of video (for a generic architecture) are as follows:

1. Compute the "2D complex-valued profile of virtual-scene wave on useful portion" as shown at 5610.

2. Back-propagate the "2D complex-valued profile of virtual-scene wave on useful portion" computed in step 1 to the SLM plane—possibly pass backwards through intermediate components—find the "ideal 2D complex-valued profile of wave at the exit of SLM" as shown at 5620.

3. Find the "2D complex-valued profile of wave illuminating the SLM", by propagating the wave emitted by the point light source and tracing it through the possibly present intermediate components as shown at 5630.

4. Determine the "2D ideal analog complex-valued SLM transmittance", which is the transmittance the SLM must implement as the multiplicative mask profile that transforms the "2D complex-valued profile of wave illuminating the SLM" computed in step 3 to the "ideal 2D complex-valued profile of wave at the exit of SLM" computed in step 2 as shown at 5640.

5. Apply appropriate prefiltering to the "2D ideal analog complex-valued SLM transmittance" to compensate for the effects of SLM structure (sampling and interpolation) to arrive at the "2D ideal complex-valued discrete SLM image" that needs to be displayed on the SLM as shown at 5650.

6. Quantize and encode the ideal "2D ideal complex-valued discrete SLM image" obtained in Step 5 into a phase-only, binary, amplitude-only, etc. representation depending on the modulation capabilities of the SLM, and find the "2D actual digital SLM image" that is suitable for displaying on the SLM as shown at 5660. During this step, actions are taken to make sure that the resulting noise beams fall outside the useful portion of the exit pupil plane.

A more detailed explanation of computation steps follows.

1. Computation of "2D Complex-Valued Profile of Virtual-Scene Wave on Useful Portion."

In various embodiments of the present invention, the user sees a virtual scene by intercepting the light wave delivered to the useful portion of the exit pupil plane. Therefore, the computational procedure starts by the computation of the light wave that should be delivered to the useful portion, which is referred to herein as the "2D complex-valued profile of virtual-scene wave on useful portion". This wave carries all the information about the virtual scene. Ideally, the display system delivers only this wave within the useful portion and nothing else. However, as discussed above, due to the restrictions of the SLMs, several undesired beams are also generated by the SLM and they propagate to the exit pupil plane, but hopefully fall outside the useful portion. In order to compute the "2D complex-valued profile of virtual-scene wave on useful portion", first of all, we need a computer-graphics model to represent the virtual scene. Various models exist in the literature to represent virtual scenes on a computer, ranging from simple point cloud models to more complicated polygon mesh based models.

In some embodiments of the presented invention, a point cloud model is used to represent a virtual scene. In this model, the virtual scene is assumed to consist of a finite number of point light sources. Depending on the location of the useful portion, some of these virtual-scene points are visible, while some others are non-visible, due to occlusion. The "2D complex-valued profile of virtual-scene wave on useful portion" can be computed (for a single wavelength) by superposing the diverging spherical waves emitted by each of the visible virtual scenes on the useful portion as follows:

$$U_{vs}(x, y) = \sum_{i=1}^{M} \left[ \sqrt{I_i} \, (e^{J\phi_i}) \frac{e^{(J\frac{2\pi}{\lambda} R_i)}}{R_i} \right] \quad (2)$$

where:

$$R_i = \sqrt{(x - x_i)^2 + (y - y_i)^2 + z_i^2}, \quad (3)$$

$U_{VS}(x, y)$ is the 2D complex-valued profile of virtual-scene wave on useful portion, M is number of virtual-scene points that are visible, $I_i$ is the intensity of the $i^{th}$ virtual-scene point, $\phi_i$ is the phase of the $i^{th}$ virtual-scene point, $(x_i, y_i, z_i)$ is the location of the $i^{th}$ virtual-scene point, $\lambda$ is the wavelength, and $J=\sqrt{-1}$.

The computation according to the formula above applies for a single color. Therefore, the computation should be repeated for all different color components in a multicolor display embodiment.

The computation according to the formula above also applies only for a certain position of the pupil position. In some embodiments of the present invention, providing a motion parallax upon changing positions of eye pupils of the user (as a result of eye or head motion) is not critical or demanded at all. In these cases, the computation in the above equation does not need to be updated, and it is sufficient to only steer the display light to the new position of the eye pupil, using mechanisms that are described more fully below.

In some other embodiments of the present invention, it is desired for the system to provide a motion parallax. In that case, when the position of the eye pupil changes, which corresponds to a change in perspective from which the virtual scene is viewed, one needs to identify the new set of virtual-scene points that become visible, and the new set of occluded virtual-scene points. Then, the "2D complex-valued profile of virtual-scene wave on useful portion" should be recalculated as described above.

In some embodiments of the present invention, the polygon mesh models might be more suitable, especially when system compatibility with or expandability on existing computer-graphics hardware and software is of concern. In that case, most of the computer-graphics-related tasks such as occlusion, shading, etc. can be accomplished on a graphical processing unit (GPU). In particular, for a viewpoint of interest (or, for a given position of the useful portion), the virtual scene, which is represented by polygon mesh models, can be rendered by a GPU, which handles any occlusion, shading etc. effects as currently done with standard GPUs embedded in computers, smart phones etc. Then, the final rendered RGB image, as well as the depth or z buffer data (which is a standard piece of data stored in GPUs and represents the distance of each rendered virtual-scene point to viewpoint under consideration) can be imported from the GPU. For each pixel of the RGB image, a spherical wave term, emitted from the depth location of the point as inferred from the z or depth buffer, can be superposed to compute the "2D complex-valued profile of virtual-scene wave on useful portion", as described above.

2. Computation of the "Ideal 2D Complex-Valued Profile of Wave at the Exit of SLM"

This step involves numerically back-propagating the "2D complex-valued profile of virtual-scene wave on useful portion" through any optical components that lie in the pathway between the exit pupil plane and the SLM, including sections of free space, and determining the "ideal 2D complex-valued profile of wave at the exit of SLM". Here, the identifier "ideal" stresses that if this field were present at the exit of the SLM, the light wave distribution on the exit pupil plane would not consist of any undesired components.

In some embodiments of the present invention, the SLM is placed directly in front of the user's eye. Therefore, there are no optical components in between except for a section of free space. In this case, the "ideal 2D complex-valued profile of wave at the exit of SLM" can be found as:

$$U_{ExS}(x,y) = \{U_{VS}(x,y) W_{up}(x,y)\} **h_{-D_{ex}}(x,y) \quad (4)$$

where:

$$W_{up}(x, y) = \begin{cases} 1 & \text{within useful portion} \\ 0 & \text{outside useful portion} \end{cases}, \quad (5)$$

$$h_D(x, y) = \frac{D}{J\lambda} \frac{e^{J\frac{2\pi}{\lambda} R}}{R^2}, \quad (6)$$

$$R = \sqrt{x^2 + y^2 + D^2}, \quad (7)$$

$U_{ExS}(x, y)$ is the ideal 2D complex-valued profile of wave at the exit of SLM, $U_{VS}(x, y)$ is the 2D complex-valued profile of virtual-scene wave on useful portion, $W_{up}(x, y)$ is the aperture function of useful portion, and $h_D(x, y)$ is the impulse response of free-space propagation.

In some embodiments of the present invention, there are some other optical components between the SLM and exit pupil plane. In that case, in addition to the free-space-propagation computations between different components, detailed wave optics models to account for the behavior of the components should be developed. These models should relate the light wave distribution at the entrance side to the light wave distribution at the exit side of a component. Note that when the model for each component is sufficiently detailed; aberrations, distortions, diffraction effects, and other effects introduced by the components between the eye and the SLM are incorporated into the computations automatically.

3. Computation of "2D Complex-Valued Profile of Wave Illuminating the SLM."

This step involves development of detailed wave optics models for components that lie in the pathway between the point light source and the SLM, and propagating the light wave emitted by the point light source and passing it through the related components. Aberrations introduced by components between the point light source and the SLM are incorporated in the computations in this manner.

4. Computation of "2D Ideal Analog Complex-Valued SLM Transmittance."

The SLM ideally should act as a multiplicative optical mask that transforms "2D complex-valued profile of wave illuminating the SLM" computed in step 3 to the "ideal 2D complex-valued profile of wave at the exit of SLM" computed in step 2. Thus, "2D ideal analog complex-valued SLM transmittance" can be found by dividing the "ideal 2D complex-valued profile of wave at the exit of SLM" computed in step 2 by the "2D complex-valued profile of wave illuminating the SLM" computed in step 3, under the assumption that the latter wave does not vanish at any point on the SLM. Therefore, $$U_{SLM}(x, y) = \frac{U_{ExS}(x, y)}{U_{ill}(x, y)} \quad (8)$$

where:

$U_{SLM}(x, y)$ is the 2D ideal analog complex-valued SLM transmittance, $U_{ExS}(x, y)$ is the ideal 2D complex-valued profile of wave at the exit of SLM, and $U_{ill}(x, y)$ is the 2D complex-valued profile of wave illuminating the SLM.

If the SLM had submicron pixels and were full complex, the "2D ideal analog complex-valued SLM transmittance" could directly be sampled and displayed on the SLM. However, the restrictions on the SLM necessitate further processing.

5. Computation of "2D Ideal Complex-Valued Discrete SLM Image."

The finite pixel pitch of the SLM is associated with sampling of the "2D ideal analog complex-valued SLM transmittance". In order to avoid aliasing, the bandwidth of the "2D ideal analog complex-valued SLM transmittance" over any small region of the SLM must not exceed the inverse of SLM pixel pitch. Under the assumption that this condition is satisfied, the "2D ideal analog complex-valued SLM transmittance" can be safely sampled. However, the actual SLM has a finite aperture function, which is the interpolating function for the sampled discrete image implemented on the SLM. Since a non-impulsive interpolating function imposes variations over the frequency spectrum of the interpolated digital image, a compensation prefilter is applied to the "2D ideal analog complex-valued SLM transmittance" prior to discretization. Hence, "2D ideal complex-valued discrete SLM image" is obtained by first applying a compensation prefilter and then sampling the "2D ideal analog complex-valued SLM transmittance".

6. Computation of "2D Actual Digital SLM Image."

As described above, real SLMs mostly perform some restricted type of modulation—such as phase only, amplitude only, binary, etc. Moreover, each pixel of a real SLM usually has a finite number of available values. Therefore, the "2D ideal complex-valued discrete SLM image" needs to be quantized and encoded into a restricted type image that is suitable for displaying on the SLM. The quantization and encoding procedure will inevitably generate some noise beams. However, it is possible to perform the mentioned encoding and quantization such that the resulting noise beam falls outside the useful portion as much as possible. This may be performed using any suitable method, including, but not limited to, Iterative Fourier Transform Algorithm, Gerschberg-Saxton algorithm, Fineup Algorithm with Don't Care, Error Diffusion, Direct Binary Search, etc.—These are all existing commonly known and used algorithms. In particular, when the noise generated as a result of encoding is distributed in spatial frequency domain to regions that are outside the support of the "2D ideal complex-valued discrete SLM image", the noise beams, after getting generated by the SLM plane and propagate to the exit pupil plane, get distributed outside the useful portion.

Computations for embodiments that include moving SLM bar (e.g., FIGS. 40, 42) are the same with the exception that the SLM is partitioned into a number of slices, and the entire "2D actual digital SLM image" is displayed slice by slice in a time sequential manner depending on the scan location of the SLM bar. The scan is completed in the frame time reserved for the "2D actual digital SLM image".

FIGS. 57-64 show a number of space-angle (or space-frequency) distributions that illustrate the basics of the computation procedure. Space angle distributions are a well-known concept in the literature and illustrate the distribution of rays as a function of transverse spatial position over various planes in an optical system, and provide insight. In FIGS. 57-64, it is assumed that the SLM is illuminated by a converging spherical wave obtained from a point light source and a positive lens combination, as in FIG. 12. For sake of simplicity, a full complex SLM with impulsive pixels and a 2D space is assumed, where x is assumed to denote the transverse coordinates and z denotes the longitudinal propagation axis. The angle of each ray is measured from z axis towards +x axis.

In FIG. 57, the typical space-angle distribution of the "2D complex-valued profile of virtual-scene wave on useful portion" on the exit pupil plane is illustrated, where it is assumed that the pupil is centered around the optical axis. Note that the spatial extent is given by the size of the useful portion, and the angular extent is given by the desired field of view, as expected.

In FIG. 58, the space angle distribution of the "ideal 2D complex-valued profile of wave at the exit of SLM" is illustrated. The distribution here is essentially equal to the horizontally sheared version of the distribution in FIG. 57 as a result of the free-space-propagation relation in between.

Figure 59:
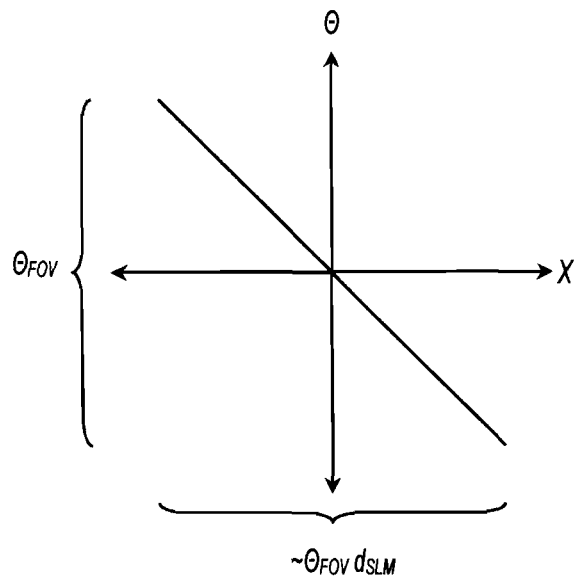

Next, in FIG. 59, the space angle distribution of the "2D complex-valued profile of wave illuminating the SLM" is illustrated, under the assumption that the lens in FIG. 12 forms a perfect converging spherical wave with no optical aberrations. Then, in FIG. 60, the space angle distribution of the "2D ideal analog complex-valued SLM transmittance", which is obtained by dividing the "ideal 2D complex-valued profile of wave at the exit of SLM" to the "2D complex-valued profile of wave illuminating the SLM", is illustrated. It is shown that the required minimum size of the SLM is determined by the FOV of the display, and the required minimum pixel rate is determined by the width of the useful portion.

Figure 60:
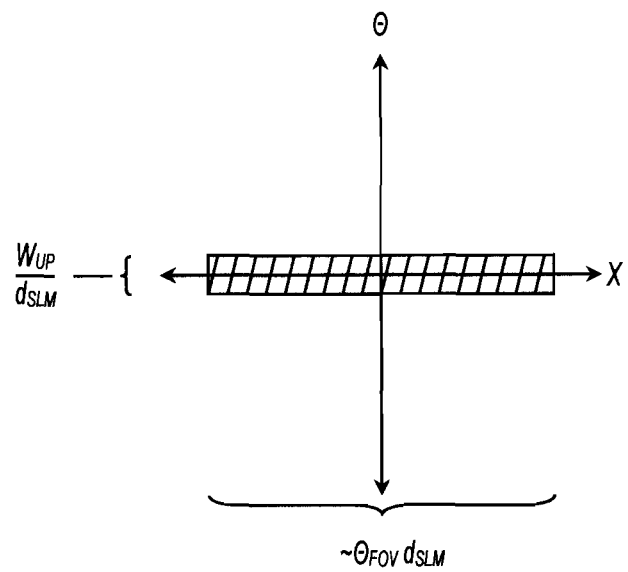
Figure 61:
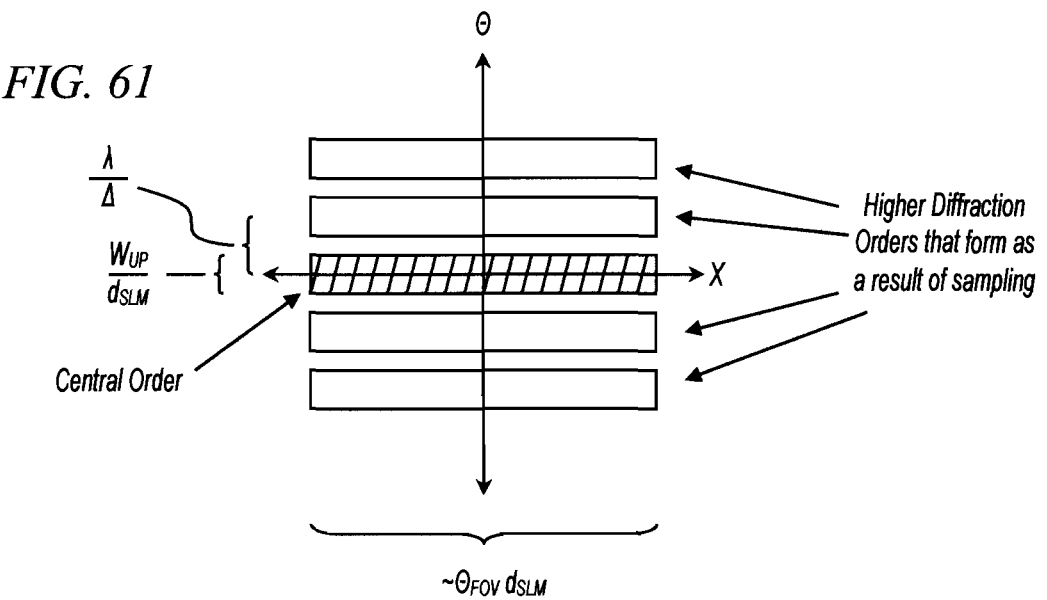
Figure 62:
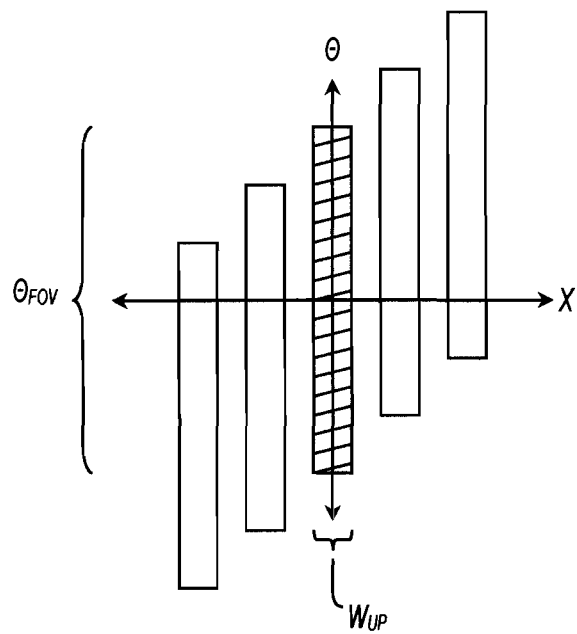

When the "2D ideal analog complex-valued SLM transmittance" is sampled to obtain the "2D ideal complex-valued discrete SLM image," the space distribution in FIG. 61 is obtained, where the distribution in FIG. 60 is replicated in the angular direction as a result of sampling. FIG. 62 shows the final distribution that is obtained on the exit pupil plane. Since the pixel pitch of the SLM is sufficiently small, higher order replicas have distributions that fall outside the spatial extent of the useful portion.

Figure 63:
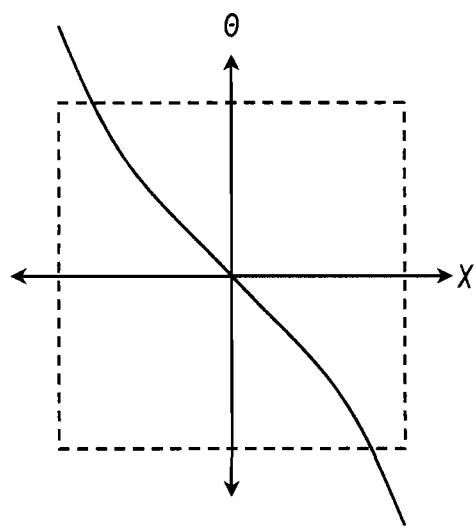
Figure 64:
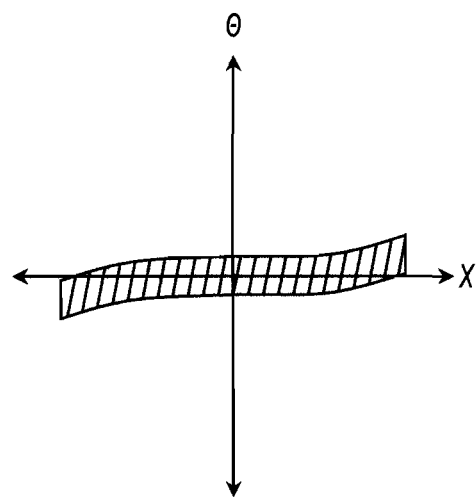

In FIG. 63, the space angle distribution of the "2D complex-valued profile of wave illuminating the SLM" is illustrated, under the assumption of a more realistic behavior for the lens in FIG. 12 that forms a converging spherical wave with spherical aberrations. Then, the space angle distribution of the "2D ideal analog complex-valued SLM transmittance" is obtained as illustrated in FIG. 64, where it is seen that there is some bending around the edges of the distribution to compensate for the presence of spherical aberration within the converging wave provided to the SLM. Since the overall distribution at any point fits within a band that is smaller than the pixel rate of the SLM, the aberration of the lens in FIG. 12 has no severe consequences and is automatically handled by computing the "2D ideal complex-valued discrete SLM image" from the space distribution in FIG. 64 instead of the distribution in FIG. 60.

Figure 65:
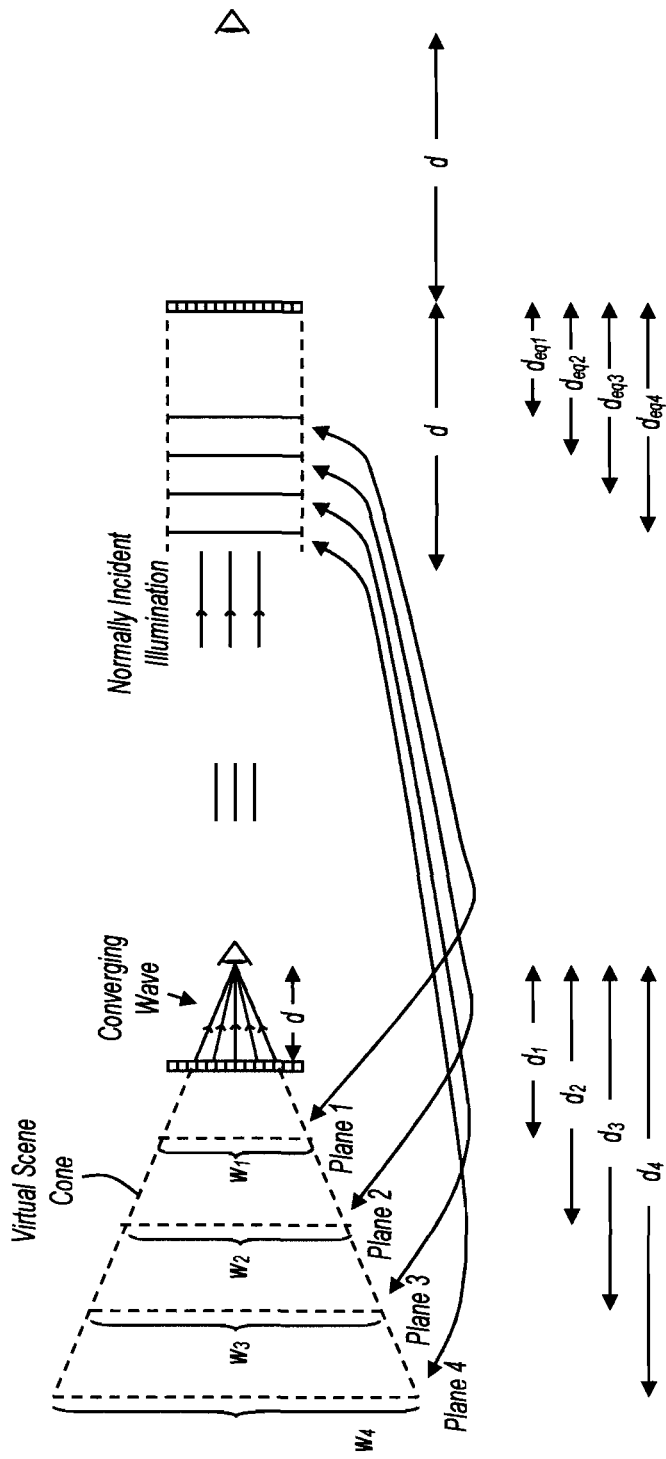
FIG. 65 shows fast hologram computation.

FIG. 65 shows a method for fast hologram computation. The computational steps detailed above in general comprise wave propagation simulations that require large storage memory and high computational power. However, in some embodiments of the present invention, there are certain mathematical relations that enable the skipping of some of the steps of the general method. One such case is that of embodiments in which the SLM is placed directly in front of the eye and is illuminated by a converging spherical wave. In that case, the mathematical relation between the "2D ideal analog complex-valued SLM transmittance" and each planar cross section of a virtual scene becomes simpler and a direct one. To see this, let us first assume that the converging illumination wave is generated by a collimated beam of light and a thin positive lens with a focal length given by D (the distance between SLM and eye), that is placed immediately before the SLM. Second, we should note that the orders of the SLM and the lens can be changed, since both are assumed to be thin multiplicative components. As a result, we get an equivalent system in which collimated light illuminates the SLM and then passes through an eyepiece lens to get directed towards the eye. Finally, consider the virtual scene shown in FIG. 65, in particular, the planar cross section labeled as Plane 4. Each point on this planar cross section, which is assumed to be quite far away from the eye, would send an almost parallel bundle of rays to the useful portion. These rays, when traced backwards to the above-mentioned eyepiece lens and passed backwards through it, get focused on the plane situated at $d_{eq4}$, and form a demagnified image of the planar cross section named Plane 4. Hence, the portion of the "2D ideal analog complex-valued SLM transmittance" responsible from Plane 4 of the virtual scene is actually equivalent to the diffraction pattern of the demagnified image of plane 4 that lies on $d_{eq4}$. The discussion applies similarly to other planar cross sections of the virtual scene. As seen in FIG. 65, the images of the planar cross sections all have the same size, and each point of these images only send a narrow cone of rays to the SLM surface that is almost parallel to the optical axis. Hence, the computation procedure can be carried out with a larger step size, and with simulation windows of a common and smaller size, lowering the memory requirements drastically. Also, the computation procedure for each planar cross section is completed in parallel through the well-known Angular Spectrum method, hence no loops over the points on a planar cross section are needed.

Accordingly, the two-dimensional complex-valued profile of a virtual-scene wave on a useful portion of an exit pupil plane may in some embodiments be determined by:

partitioning the virtual scene into a plurality of spherical surfaces concentric at the center of the useful portion of the exit pupil plane with different radius;

forming a matrix for each of the spherical surfaces where each element of the matrix is associated with a specific angular location on the sphere, and each element is filled with the complex amplitude of the point source at that angular location on the sphere;

inverse Fourier transforming the matrix to create a result;

multiplying the result by a common diverging lens term with a focal length equal to the radius of the sphere; and repeating the partitioning, forming, inverse Fourier transforming, and multiplying for each of the plurality of spherical surfaces and superposing to find the two-dimensional complex-valued profile of the virtual-scene wave on the useful portion of the exit pupil plane.

FIG. 66 illustrates the fundamentals of the method for delivering speckle free images to the retina of a user. Speckle noise is observed when real objects are imaged by a user under coherent light, due to the fact that surface irregularities of real objects lead to a random phase distribution over the object. In particular, each point of a real object point is imaged as an Airy disk on the retina due to diffraction from eye pupil. Hence, individual images of object points overlap on the retina. Since the illumination is coherent, these individual images do interfere with each other. The random phase on the real object points causes this interference pattern to exhibit rapid constructive and destructive interference patterns, which are seen as the speckle noise over the image of a real object. It is also well known that speckle noise depends on the relative position between eyes of an observer and the object that is imaged, and the speckle noise pattern changes as the eye moves.

The various embodiments of the present invention are not imaging real objects under coherent illumination. Rather, they are delivering images of virtual objects to the retina using coherent illumination. This case is different than the case of real objects in that we have total control over the phase distribution that we can assign to virtual object points.

In FIG. 66, the image on the retina of a virtual object that consists of a number of point sources is illustrated for two cases. In both cases, the final continuous intensity function that forms on the retina is obtained as an interpolated version of the discrete images of virtual object points. In fact, assuming a rectangular eye pupil with dimensions $wp_x$ and $wp_y$ and centered around $(x_p, y_p)$, and a planar virtual object placed at a distance d from the eye that consists of M point sources located at $(x_i, y_i)$ on the transverse plane, the effective intensity distribution as seen by the eye becomes:

$$I_{EO}(x, y) = \left| \sum_{i=1}^{M} c_i e^{j\frac{2\pi}{\lambda} R_i} \mathrm{sinc}\left(\frac{x - x_i}{\left(\frac{\lambda d}{wp_x}\right)}\right) \mathrm{sinc}\left(\frac{y - y_i}{\left(\frac{\lambda d}{wp_y}\right)}\right) \right|^2 \quad (9)$$

where:

$$\mathrm{sinc}(x) = \frac{\sin(\pi x)}{\pi x}, \quad (10)$$

$$R_i = \sqrt{(x_i - x_p)^2 + (y_i - y_p)^2 + d^2}, \quad (11)$$

$I_{EO}(x, y)$ is the intensity of effective object that is seen by the eye at the current position of eye pupil, $c_i$ is the complex amplitude of the $i^{th}$ object point, ($wp_x$, $wp_y$) are the dimensions of the eye pupil—assumed to be rectangular here, and ($x_i$, $y_i$) are the transverse coordinates of each object point.

In the upper case, a random phase variation is assigned to the object points. As a result, the intensity function exhibits rapid intensity variations between the discrete images of virtual object points. The user perceives these rapid changes as the speckle noise. In the lower case, an appropriate phase distribution has been assigned to the virtual object points. As a result, the intensity function that forms on the retina is a smoothly interpolated version of discrete images of virtual object points. Hence, the image delivered by the system resembles the image that would be seen under incoherent illumination, free of speckle noise.

In particular, if the light from each of the individual virtual object points arrives at the retina of the user with the same phase, then the interpolation that forms on the retina becomes smooth. An equivalent condition is that light waves from each object point to arrive at the pupil of the user in phase. Therefore, if a virtual object point that has a distance of R to the center of the pupil is assigned a phase of $e^{-jkR}$ with k denoting the wave number, the light from all virtual object points arrives on the pupil of the user in phase, and form a speckle-free retinal image. Note that the proposed phase assignment is specific to a certain pupil position and wavelength. Hence, it must be updated when the pupil location changes, and when the object wave within the useful portion is calculated for a different color.

To sum up, in the embodiments of this invention, during the computation of the "2D complex-valued profile of virtual-scene wave on useful portion" (see FIG. 66); the phase assignment rule explained here is used. In this manner, the virtual objects are imaged free of speckle.

Various embodiments of Back-Light Units (BLUs) are now described. Many of the BLUs described below are suitable for use in an illumination optics module such as illumination optics module 440 (FIG. 4). Various BLU embodiments create coherent light beams that may be converging, diverging, or collimated. BLUs are also described as being part of near-to-eye display devices. The BLUs may be incorporated in any near-to-eye described herein, including for example those described with reference to FIGS. 1, 3, 35, and 53.

Figure 67:
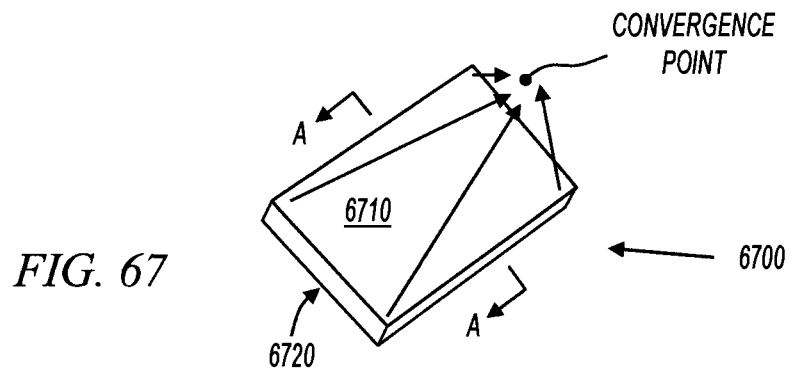
FIG. 67 shows a perspective drawing of a back-light unit that generates a two-dimensional converging beam.

FIG. 67 shows a perspective view of a back-light unit that generates a two-dimensional converging beam. The rays emanate from a transparent substrate and focus on the convergence point. Back-light unit 6700 includes first face 6710 from which a converging light beam emanates. Back-light unit 6700 also includes second face 6720. In some embodiments, faces 6710 and 6720 are parallel, but this is not a limitation of the present invention.

Apparatus 6700 is referred to as a "back-light unit" in part because it can be used to "back light" an SLM with a converging beam (or other type of beam). Optically, back-light unit 6700 is equivalent to the combination of point light source 120 and lens 1210 as shown in FIG. 12; however, back-light unit 6700 provides a significant space savings as compared to the system shown in FIG. 12.

Figure 68:
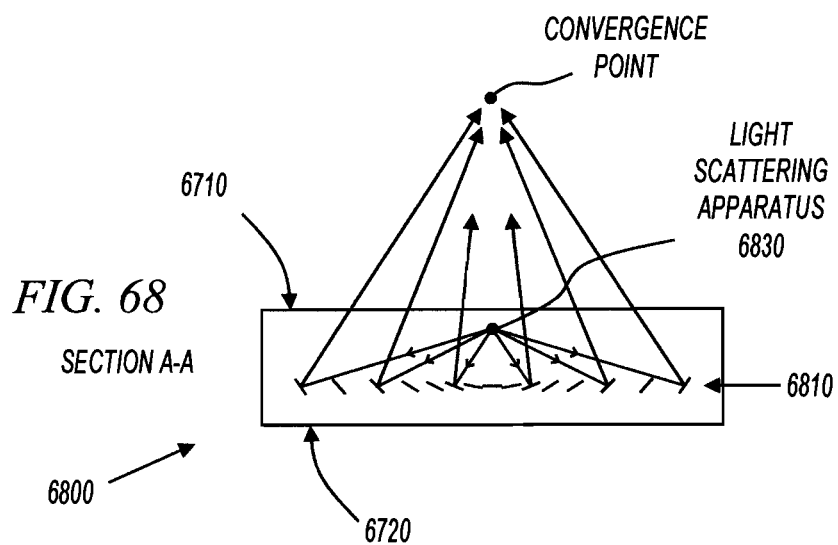
FIG. 68 shows a cross section of the back-light unit of FIG. 67 showing a scattering point and linearly arranged micromirror array.

FIG. 68 shows a cross section of a back-light unit. Back-light unit 6800 corresponds to back-light unit 6700 (FIG. 67) implemented with a light-scattering apparatus 6830 and a reflective optical element arranged as a planar micromirror array 6810. The term "planar micromirror array" as used herein refers to the individual mirrors being arranged on a plane, and is not meant to infer that each mirror has the same tilt angle. The light emanating from light-scattering apparatus 6830 hits the micromirror array and then focuses on the convergence point. The position of each individual micromirror in the array 6810 is arranged such that it reflects the incoming ray from light-scattering apparatus 6830 to the convergence point. In order to have a transparent substrate, the micromirror array 6810 is buried in a refractive index matched medium. In some embodiments, the reflectivity of the micromirror array can be provided either by notch coating, semi-reflective thin metal coating, or the like.

Light-scattering apparatus 6830 scatters light away from the first face 6710, and micromirror array 6810 reflects the light from scattering apparatus 6830 to first face 6710 and creates the converging light beam. In some embodiments, light-scattering apparatus 6830 receives light from an external light source (not shown), and in other embodiments, light-scattering apparatus 6830 is co-located with one or more light sources embedded within the back-light unit, and scatters light away from the first face 6710. For example, in some embodiments, an organic light emitting diode (OLED) is embedded within the substrate to provide light to the light-scattering apparatus 6830. Also for example, in some embodiments, red, green, and blue (RGB) OLEDs are included in back-light unit 6800. Further, in some embodiments, a fluorescent molecule such as a quantum dot is embedded in the substrate as a light source. In general, any of the back-light units described herein may include any internal or external light source.

In some embodiments, the light-scattering apparatus 6830 includes a diffusive material such as silver epoxy or epoxy with embedded microparticles. Further, in some embodiments, the same scattering apparatus is provided for all the colors. Some embodiments include multiple scattering apparatus (a "source array") in order to increase FOV.

Figure 69:
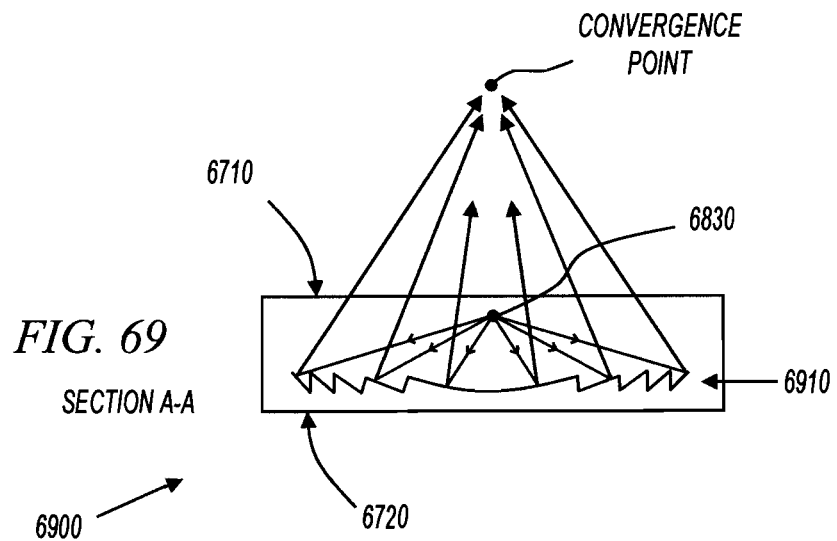
FIG. 69 shows a cross section of the back-light unit of FIG. 67 showing a light-scattering apparatus and a reflective optical element arranged as a Fresnel mirror.

FIG. 69 shows a cross section of a back-light unit. Back-light unit 6900 corresponds to back-light unit 6700 (FIG. 67) implemented with light-scattering apparatus 6830 and reflective optical element 6910 arranged as a Fresnel mirror. Light-scattering apparatus 6830 scatters light away from the first face 6710, and Fresnel mirror 6910 reflects the light from scattering apparatus 6830 to first face 6710 and creates the converging light beam.

Figure 70:
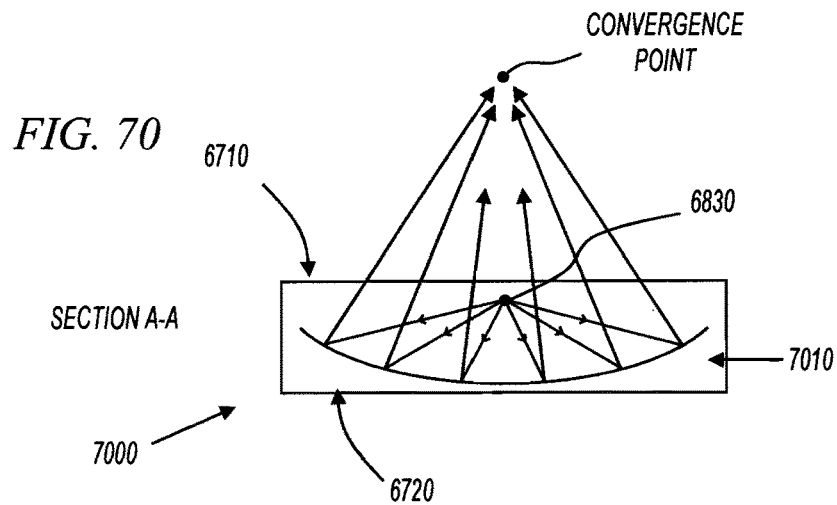
FIG. 70 shows a cross section of the back-light unit of FIG. 67 showing a light-scattering apparatus and a reflective optical element arranged as a free form concave reflector.

FIG. 70 shows a cross section of a back-light unit. Back-light unit 7000 corresponds to back-light unit 6700 (FIG. 67) implemented with light-scattering apparatus 6830 and a reflective optical element arranged as a free-form concave reflector 7010. Light-scattering apparatus 6830 scatters light away from the first face 6710, and reflector 7010 reflects the light from scattering apparatus 6830 to first face 6710 and creates the converging light beam.

Figure 71:
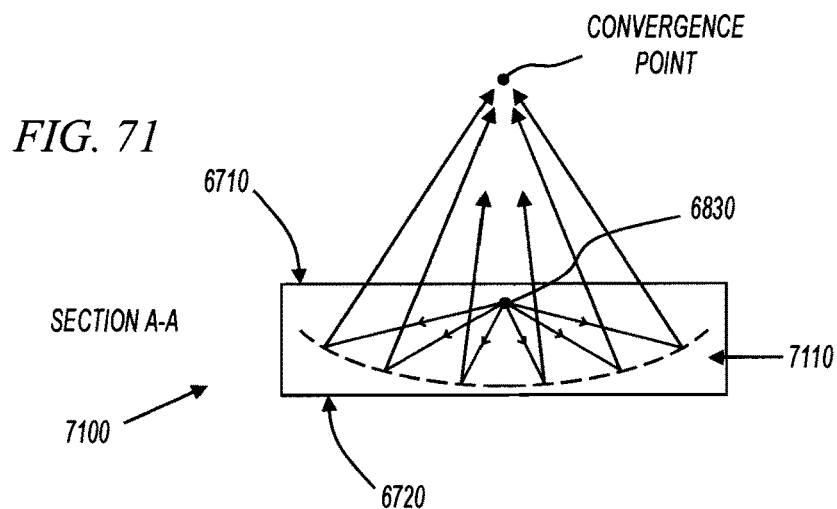
FIG. 71 shows a cross section of the back-light unit of FIG. 67 showing a scattering point and nonlinearly arranged micromirror array.

FIG. 71 shows a cross section of a back-light unit. Back-light unit 7100 corresponds to back-light unit 6700 (FIG. 67) implemented with light-scattering apparatus 6830 and a reflective optical element arranged as a nonplanar micromirror array 7110. Light-scattering apparatus 6830 scatters light away from the first face 6710, and nonplanar micromirror array 7110 reflects the light from scattering apparatus 6830 to first face 6710 and creates the converging light beam. Nonplanar micromirror array 7110 reduces the shadowing effects in between the individual mirrors of a planar micromirror array.

Figure 72:
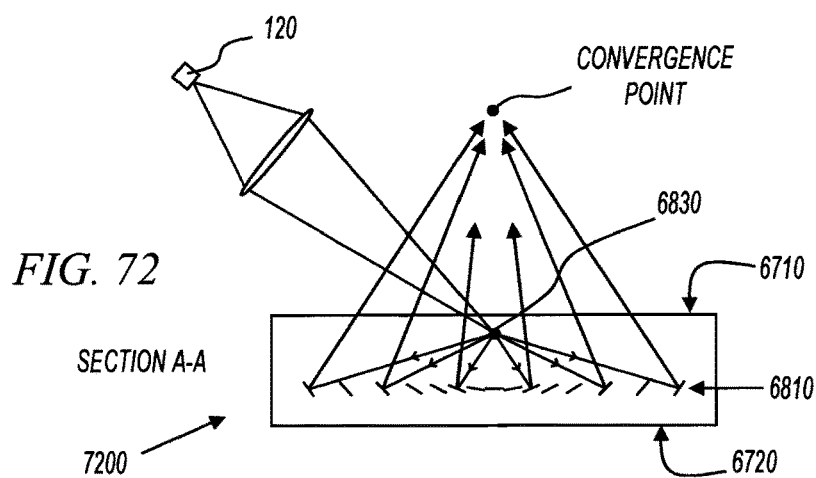
FIG. 72 shows a back-light unit with an external light source.

FIG. 72 shows a cross section of a back-light unit and an external point light source. Back-light unit 7200 corresponds to back-light unit 6700 (FIG. 67) implemented with light-scattering apparatus 6830 and a reflective optical element arranged as a planar micromirror array 6810. Light-scattering apparatus 6830 scatters light away from the first face 6710, and planar micromirror array 6810 reflects the light from scattering apparatus 6830 to first face 6710 and creates the converging light beam. The light emanates from an external point light source 120, and is focused on light-scattering apparatus 6830 inside the transparent substrate.

Figure 73:
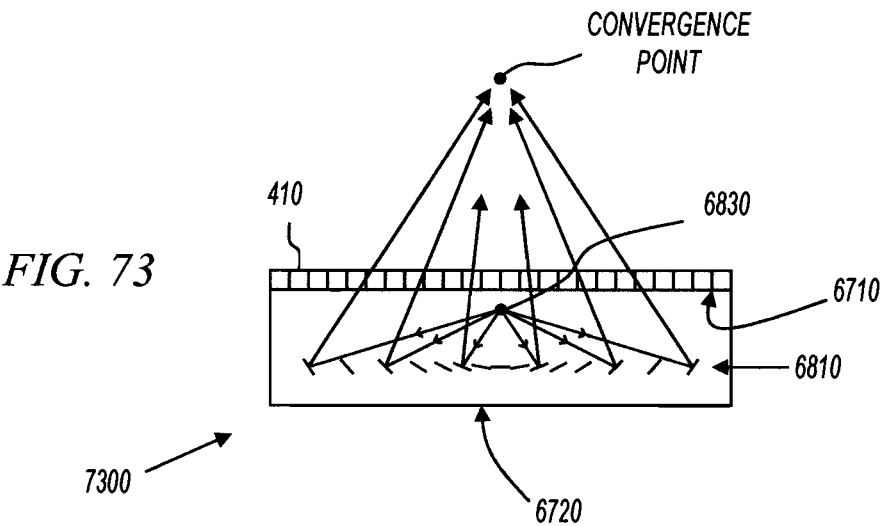
FIG. 73 shows a cross section of a back-light unit with transmissive SLM.

A combination of an SLM and a transparent back-light unit with converging beam output can be used as a near-to-eye display device. FIG. 73 shows a near-to-eye display device that includes back-light unit 7300 and transmissive SLM 410. Back-light unit 7300 corresponds to back-light unit 6700 (FIG. 67) implemented with light-scattering apparatus 6830 and a reflective optical element arranged as a planar micromirror array 6810. Light-scattering apparatus 6830 scatters light away from the first face 6710, and micromirror array 6810 reflects the light from scattering apparatus 6830 to first face 6710 to create the converging light beam. The converging beam at the output of the back-light unit passes through transmissive SLM 410 and then focuses on the eye pupil. In this configuration, the SLM has a computer-generated hologram written on it in order to construct the desired light field on the retina.

Figure 74:
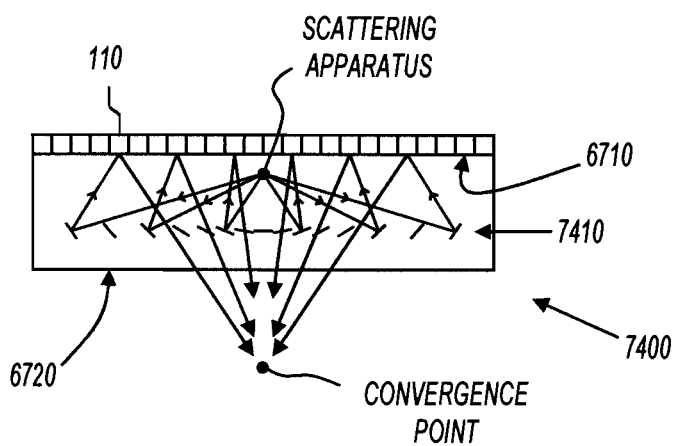
FIG. 74 shows a cross section of a back-light unit with a reflective SLM.

Alternatively, a reflective SLM 110 can be used in the near-to-eye display device instead of the transparent SLM as can be seen in FIG. 74. FIG. 74 shows a near-to-eye display device that includes back-light unit 7400 and reflective SLM 110. Back-light unit 7400 corresponds to back-light unit 6700 (FIG. 67) implemented with light-scattering apparatus 6830 and a linearly arranged transreflective micromirror array 7410. Light-scattering apparatus 6830 scatters light away from the first face 6710, and transreflective micromirror array 7410 reflects the light from scattering apparatus 6830 to first face 6710 where it is modulated and reflected by reflective SLM 110. The modulated virtual-scene wave passes back through transreflective micromirror array 7410 and emanates from the second face 6720 as a converging beam that focuses on the eye pupil. In this configuration, the SLM has a computer-generated hologram written on it in order to construct the desired light field on the retina.

Figure 75:
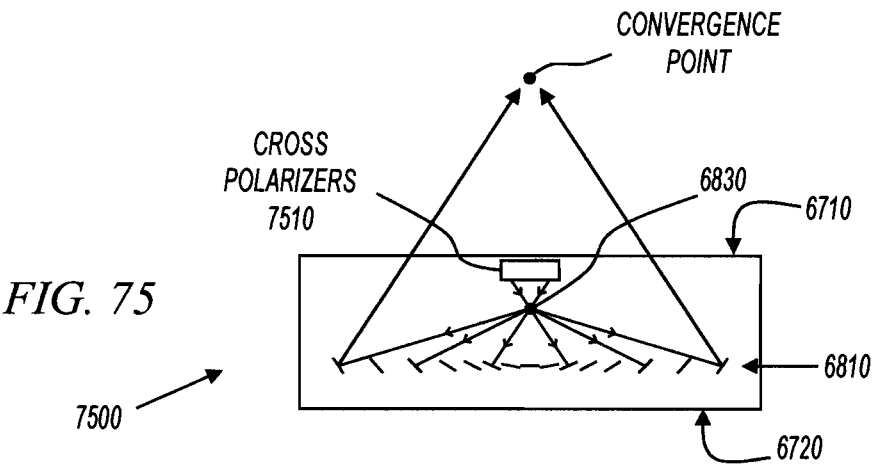
FIG. 75 shows a cross section of back-light unit with cross polarizers.

The light scattered in the direction of the convergence point from the light-scattering apparatus can create a bright spot on the retina in near-to-eye display device applications. This unwanted portion of the scattered light can be blocked by using cross polarizers between the light-scattering apparatus and the convergence point as can be seen in FIG. 75. Back-light unit 7500 corresponds to back-light unit 6700 (FIG. 67) implemented with light-scattering apparatus 6830 and micromirror array 6810. Light-scattering apparatus 6830 scatters light away from the first face 6710, and micromirror array 6810 reflects the light from scattering apparatus 6830 to first face 6710 and creates the converging light beam. Back-light unit 7500 also includes cross polarizers 7510. In some embodiments, cross polarizers 7510 are two orthogonally polarized optical elements to block the passage of light. When cross polarizers 7510 are included, the bright spot referred to above is not present on the retina.

Figure 76:
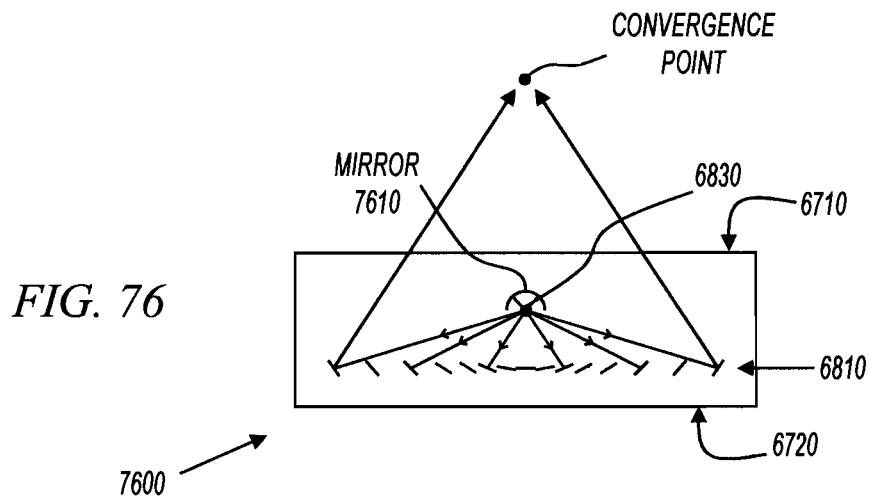
FIG. 76 shows a cross section of back-light unit with a mirror.

Alternatively, a buried curved mirror, which reflects the rays back to the scattering apparatus, can be used instead of cross polarizers as can be seen in FIG. 76, making it more light efficient. FIG. 76 shows a cross section of a back-light unit. Back-light unit 7600 corresponds to back-light unit 6700 (FIG. 67) implemented with light-scattering apparatus 6830 and a reflective optical element arranged as a planar micromirror array 6810. Light-scattering apparatus 6830 scatters light away from the first face 6710, and planar micromirror array 6810 reflects the light from scattering apparatus 6830 to first face 6710 and create the converging light beam. Back-light unit 7600 also includes mirror 7610. Mirror 7610 blocks light reflected from micromirror array 6810 that would otherwise create a bright spot on the retina. When mirror 7610 is included, the bright spot referred to above is not present on the retina.

Figure 77:
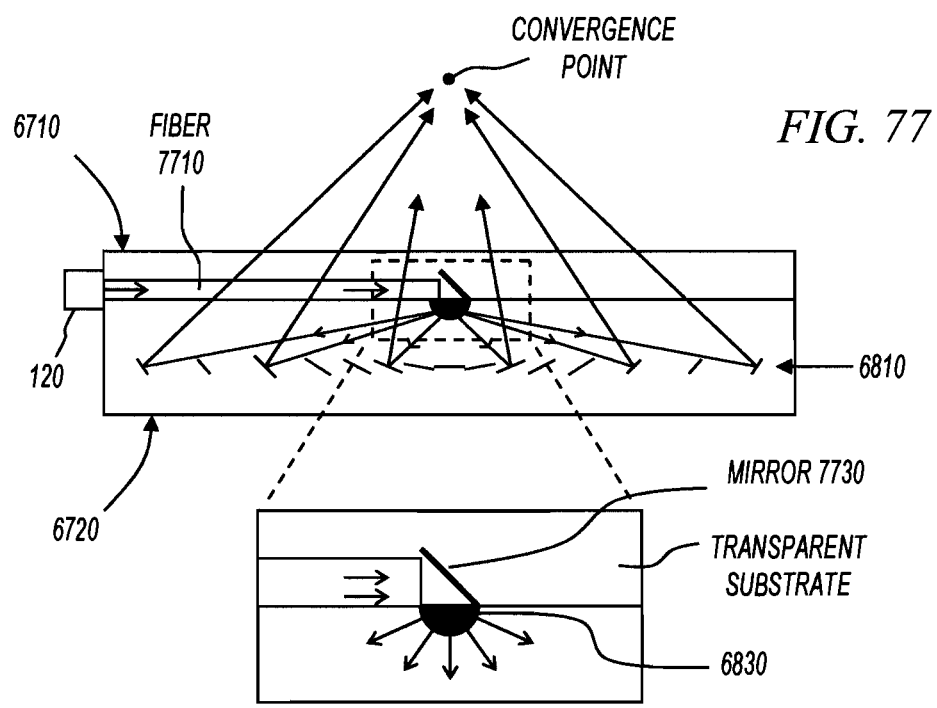
FIG. 77 shows a cross section of a back-light unit with a fiber.

FIG. 77 shows a cross section of a back-light unit with a fiber. The light carried by the fiber hits the 45°-angled mirror 7730 and is directed to light-scattering apparatus 6830, which is used for increasing the solid angle of the ray bundle for fully covering the micromirror array. Light-scattering apparatus 6830 scatters the light away from first face 6710 and towards the micromirror array 6810. The scattered light is then reflected off the micromirror array 6810 and emanates from first face 6710 as a converging beam.

In some embodiments, light-scattering apparatus 6830 can be realized by using high refractive index transparent nanoparticles. One advantage of this system can be explained as follows: the different colors can be coupled into the same fiber and directed to the same scattering apparatus. Therefore, the effective positions of the different-colored light sources do not change with respect to the micromirror array, which reduces the chromatic aberrations. In some embodiments, the end face of fiber 7710 is polished with a 45° angle and coated with metal, which is used instead of mirror 7730.

Figure 78:
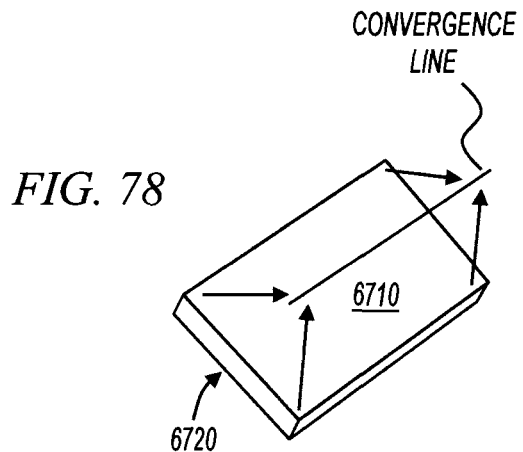
FIG. 78 shows a perspective view of a back-light unit that generates one-dimensional converging beam.
Figure 79:
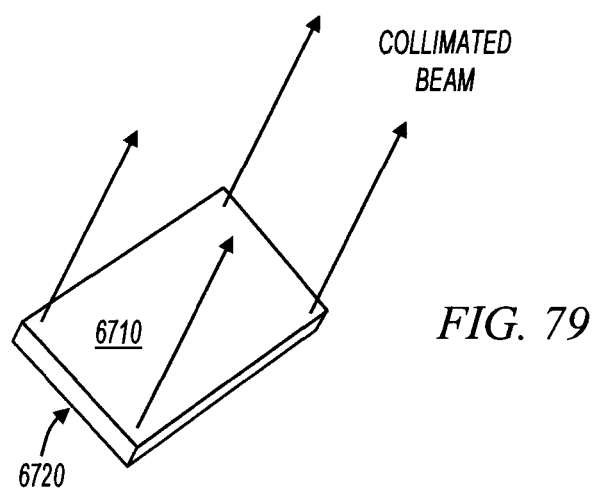
FIG. 79 shows a perspective view of a back-light unit that generates a collimated beam.
Figure 80:
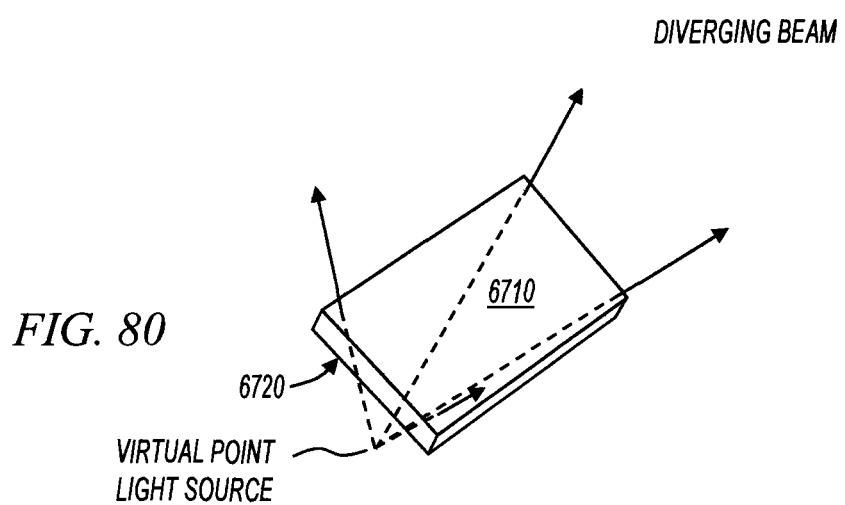
FIG. 80 shows a perspective view of a back-light unit that generates a diverging beam.

The back-light unit can be arranged such that the output beam has a profile different than the converging beam. For example, by arranging the position of the individual mirrors in the micromirror array, a one-dimensional converging beam can be generated as shown in FIG. 78. Similarly, collimated and diverging beams can be generated as can be seen in FIG. 79 and FIG. 80, respectively.

Various embodiments of wedge-based back-light units are now described. Many of the wedge-based back-light units may be used in illumination optics modules such as illumination optics module 440 (FIG. 4). Wedge-based back-light units are also described as being part of near-to-eye display devices. The wedge-based back-light units may be incorporated in any near-to-eye display device described herein, including for example those described with reference to FIGS. 1, 3, 35, and 53.

Figure 81:
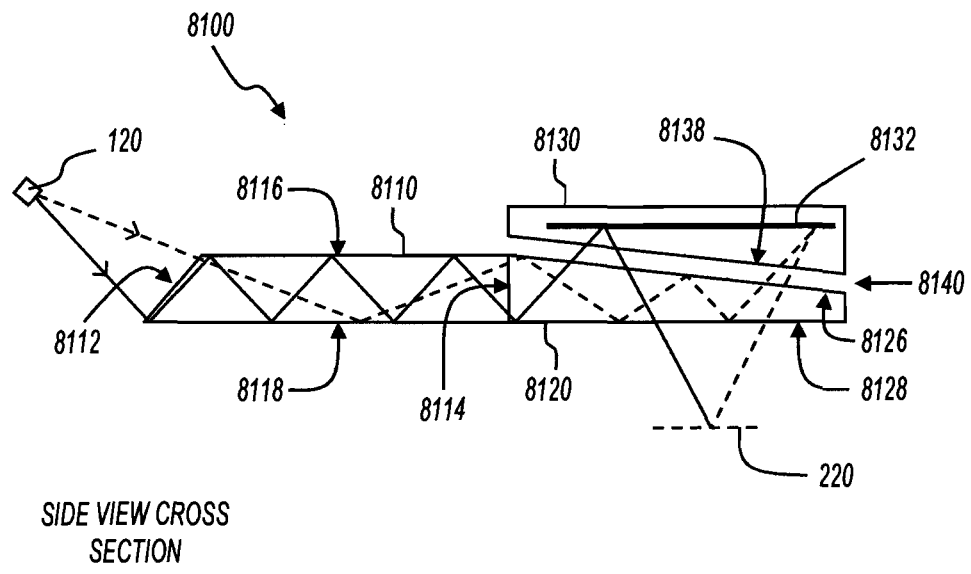
FIG. 81 shows a cross section of a slab waveguide, a wedge, and a component with a micromirror array.

FIG. 81 shows a cross section of a slab waveguide, a wedge, and a component with a micromirror array. Apparatus 8100 includes slab waveguide 8110, wedge 8120, and component 8130 with micromirror array 8132. Slab waveguide 8110 includes input end 8112, output end 8114, first surface 8118, and second surface 8116. First surface 8118 and second surface 8116 are parallel to each other to cause light to propagate from input end 8112 to output end 8114 by total internal reflection.

Wedge 8120 is coupled to the output end 8114 of slab waveguide 8110. Wedge 8120 includes first surface 8128 and slanted surface 8126 that are not parallel to each other. First surface 8128 and slanted surface 8126 form a continuously decreasing thickness to cause light received from slab waveguide 8110 to exit wedge 8120 from slanted surface 8126. In some embodiments, first surface 8128 is parallel to first surface 8118, and in other embodiments, slanted surface 8126 is parallel to first surface 8118.

Optical component 8130 includes face 8138 that is oriented parallel to slanted surface 8126. Further, optical component 8130 includes micromirror array 8132 to reflect light received through face 8138 back out through the same face 8138 and through wedge 8120. Micromirror array 8132 may be any type of micromirror array including but not limited to those shown in, and described with reference to, FIGS. 68-76.

In some embodiments, optical component 8130 has a shape that performs as a compensating wedge for see-through capability. In these embodiments, optical component 8130 is referred to a compensating wedge. When functioning as a compensating wedge, optical component 8130 has a wedge shape that complements the shape of wedge 8120 such that light traveling through both the wedge and compensating wedge travel through the same amount of material. This eliminates any prism effect that would otherwise be perceived by a user. Optical component 8130 is positioned to provide a uniform air gap 8140 between slanted surface 8126 and face 8138. In embodiments with semitransparent micromirror arrays, undistorted real-world views are provided because of the combination of the wedge and optical component 8130 in shape of a compensating wedge.

In operation, point light source 120 creates a diverging light beam. The diverging light beam enters slab waveguide 8110 at input end 8112 and propagates by total internal reflection within slab waveguide 8110 to output end 8114, at which point it enters wedge 8120. As the light beam propagates in wedge 8120, the internal angle of incidence changes due to the decreasing thickness, allowing the light beam to exit almost collimated from the slanted surface 8126 of wedge 8120. The light then enters into optical component 8130 at face 8138 and hits micromirror array 8132. The light reflected from the micromirror array goes through wedge 8120, exiting at surface 8128 as a converging wave, and then focuses onto exit pupil plane 220.

Figure 82:
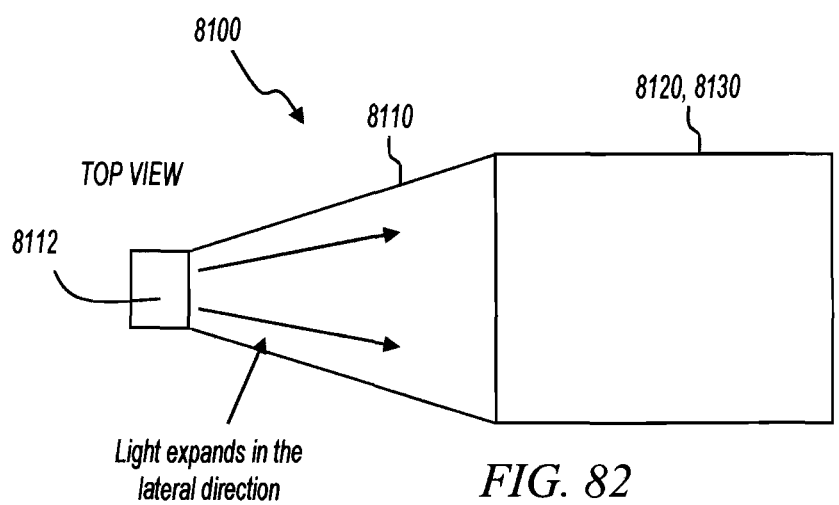
FIG. 82 shows a top view of the apparatus of FIG. 81.

FIG. 82 shows a top view of the apparatus of FIG. 81. The light entering into the slab waveguide 8110 expands in the lateral direction and is confined in the vertical direction by total internal reflection. Then the light enters into the wedge region and the rays start to exit from the wedge since the incidence angles are reduced at each reflection.

FIGS. 83-88 combine wedge-based back-light units with SLMs to form near-to-eye display devices. In operation, these perform the functions of both illumination optics module 440 and SLM 410 (FIG. 4). Direct applications to near-to-eye display devices are also described.

Figure 83:
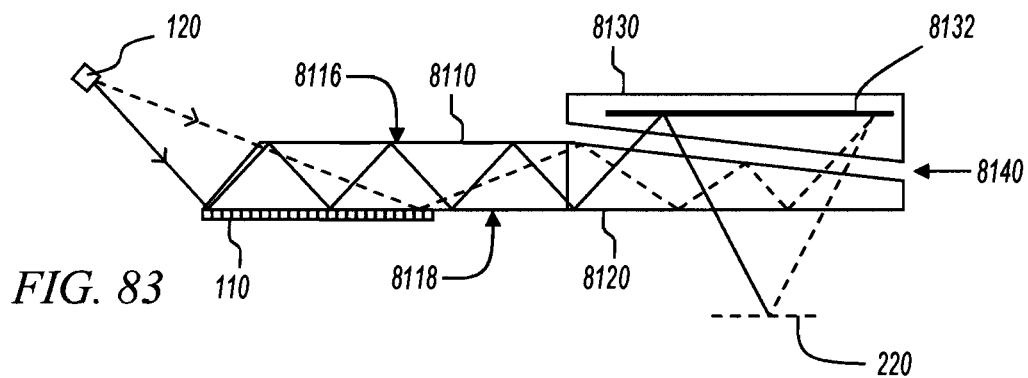
FIG. 83 shows a cross section of a slab, wedge, component with micromirror array, and SLM positioned along the slab.

FIG. 83 shows a cross section of a slab waveguide, wedge, optical component with micromirror array, and SLM positioned along the slab waveguide. In this configuration, the light field hits reflective SLM 110 while it is propagating in slab waveguide 8110. Although SLM 110 is shown on surface 8118 of slab waveguide 8110 in FIG. 83, this is not a limitation of the present invention. In some embodiments, the SLM is placed on surface 8116. The computer-generated hologram on the SLM modulates the light as it propagates in slab waveguide 8110, and the desired virtual scene is generated at the useful portion of exit pupil plane 220 as described above.

Figure 84:
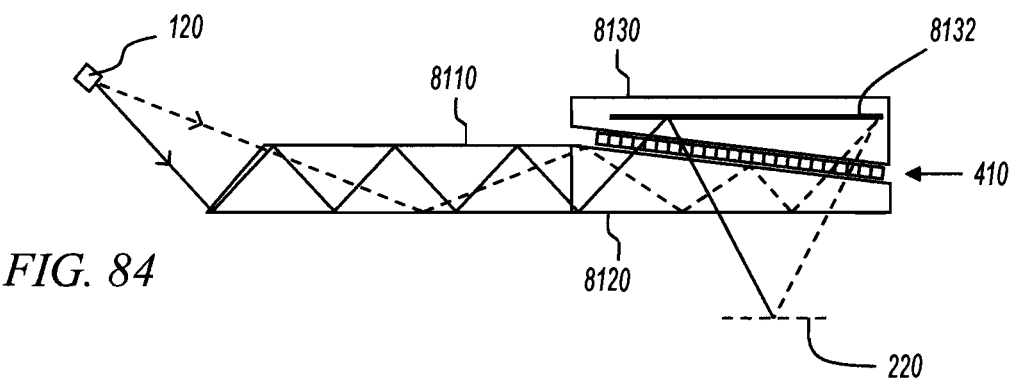
FIG. 84 shows a cross section of a slab waveguide, a wedge, a component with a micromirror array, and an SLM between the wedge and the component with the micromirror array.

FIG. 84 shows a cross section of a slab waveguide, a wedge, a component with a micromirror array, and an SLM between the wedge and the component with the micromirror array. A transmissive SLM 410 is placed in between wedge 8120 and optical component 8130. In order to generate the desired light field at the exit pupil plane 220, the collimated light at the output of wedge 8120 passes through transmissive SLM 410 which has a computer-generated hologram on it, and hits micromirror array 8132. The light field reflects from micromirror array 8132, passes through transmissive SLM 410 again and then converges on exit pupil plane 220. The light that enters from the eye pupil then constructs the desired content on the retina.

Figure 85:
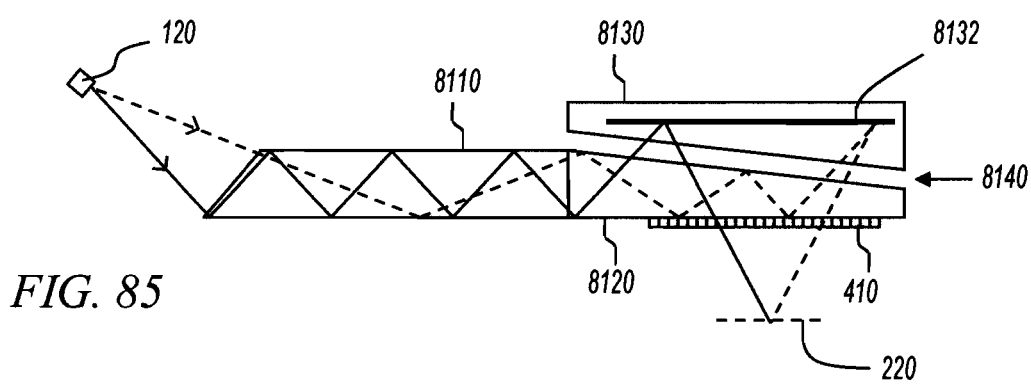
FIG. 85 shows a cross section of slab waveguide, wedge, component with a micromirror array, and an SLM below the wedge.

FIG. 85 shows a cross section of a slab waveguide, wedge, component with a micromirror array, and an SLM below the wedge. FIG. 85 is similar to FIG. 83 except that the SLM is below the wedge and it is transmissive. The combination of FIG. 85 can be used as a near-to-eye display device.

Figure 86:
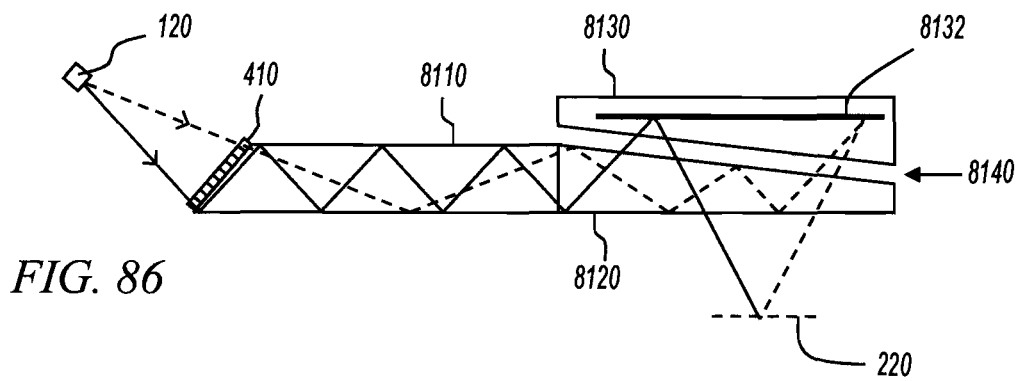
FIG. 86 shows a cross section of a slab waveguide, wedge, component with micromirror array, and an SLM at entrance to the slab.

FIG. 86 shows a cross section of a slab waveguide, wedge, component with micromirror array, and an SLM at entrance to the slab. FIG. 86 is similar to FIG. 85 except that the SLM is at the input end of the slab waveguide. The combination of FIG. 86 can be used as a near-to-eye display device.

Figure 87:
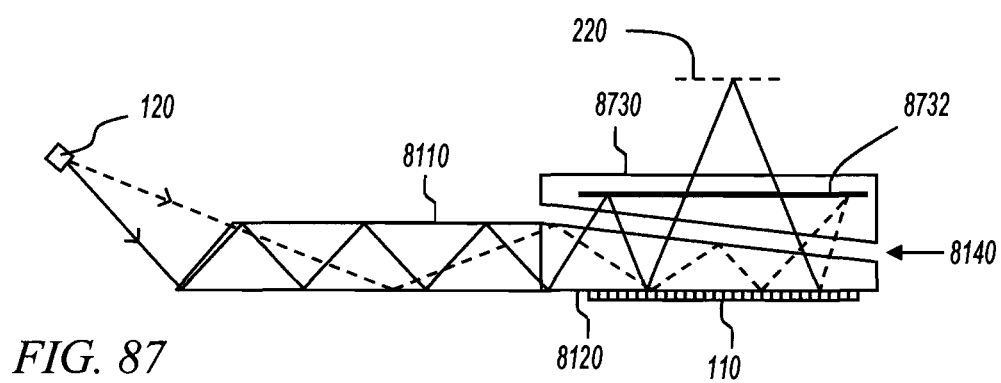
FIG. 87 shows a cross section of a slab waveguide, wedge, compensating wedge with micromirror array, and SLM below the wedge.

FIG. 87 shows a cross section of a slab waveguide, wedge, compensating wedge with micromirror array, and SLM below the wedge. In embodiments represented by FIG. 87, SLM 110 is reflective, and micromirror array 8732 is transreflective. Light first exiting wedge 8120 enters optical component 8730 and is reflected off micromirror array 8732 as a converging beam. The converging beam then passes back through wedge 8120 to be reflected and modulated by reflective SLM 110. The light reflected off SLM 110 passes back through optical component 8730, and converges at the exit pupil plane 220.

Figure 88:
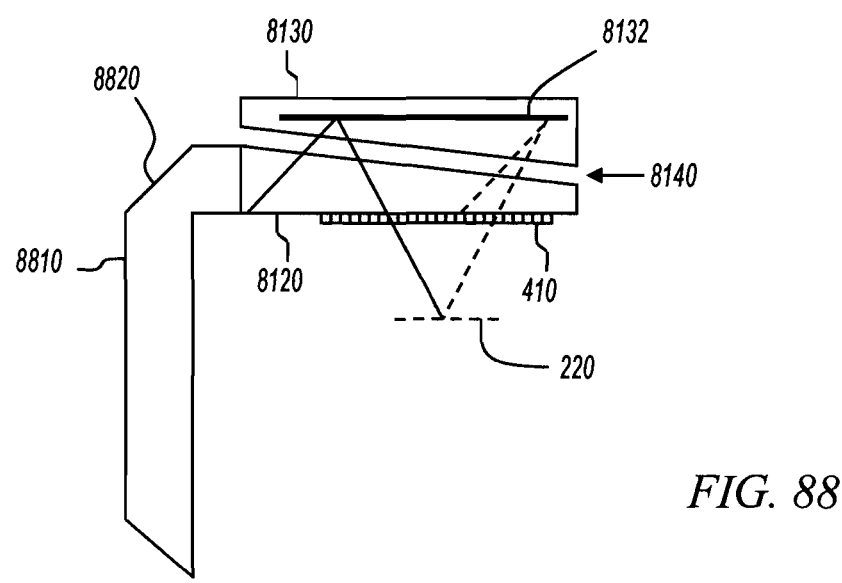
FIG. 88 shows a cross section of a slab waveguide with a 90-degree bend, wedge, optical component with a micromirror array, and an SLM.

FIG. 88 shows a cross section of slab waveguide with a 90-degree bend, wedge, optical component with a micromirror array, and an SLM. The near-to-eye display device of FIG. 88 is similar to the near-to-eye display device of FIG. 85 with the exception that slab waveguide 8810 includes a 90-degree bend in FIG. 88. Light rays propagating in slab waveguide 8810 couple into wedge 8120 by means of a turning mirror 8820. Placing at least a portion of the slab waveguide perpendicular to the major axis of the wedge as shown in FIG. 88 can reduce the form factor of the wedge-based near-to-eye display device.

Figure 89:
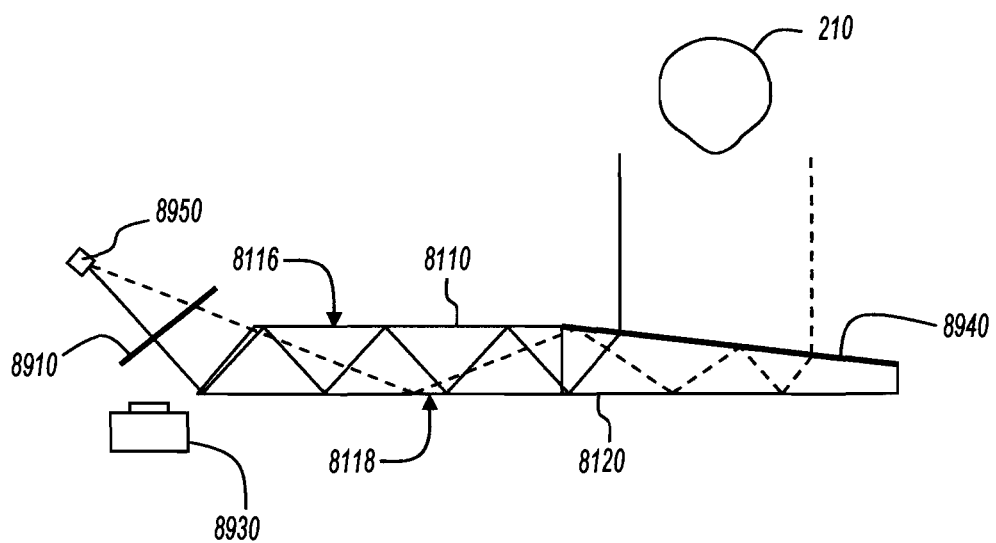
FIG. 89 shows a cross section of a slab waveguide, wedge, and camera for eye tracking.

A wedge-based eye tracker can be constructed as can be seen in FIG. 89. A near-infrared (NIR) illumination provided by light source 8950 is coupled into the slab after passing through a beam splitter 8910 and the rays exit from the wedge. A light turning film 8940 is placed on the wedge for directing the light beam towards the eye. The light reflected back from the eye is coupled back into the wedge 8120 and forms the image of the eye onto the camera, which can be used for eye tracking.

Camera 8930 is shown at the input to slab waveguide 8110 and coupled with a beamsplitter 8910. In some embodiments, camera 8930 is positioned along slab waveguide on either surface 8116 or 8118 similar to SLM 110 in FIG. 83.

Figure 90:
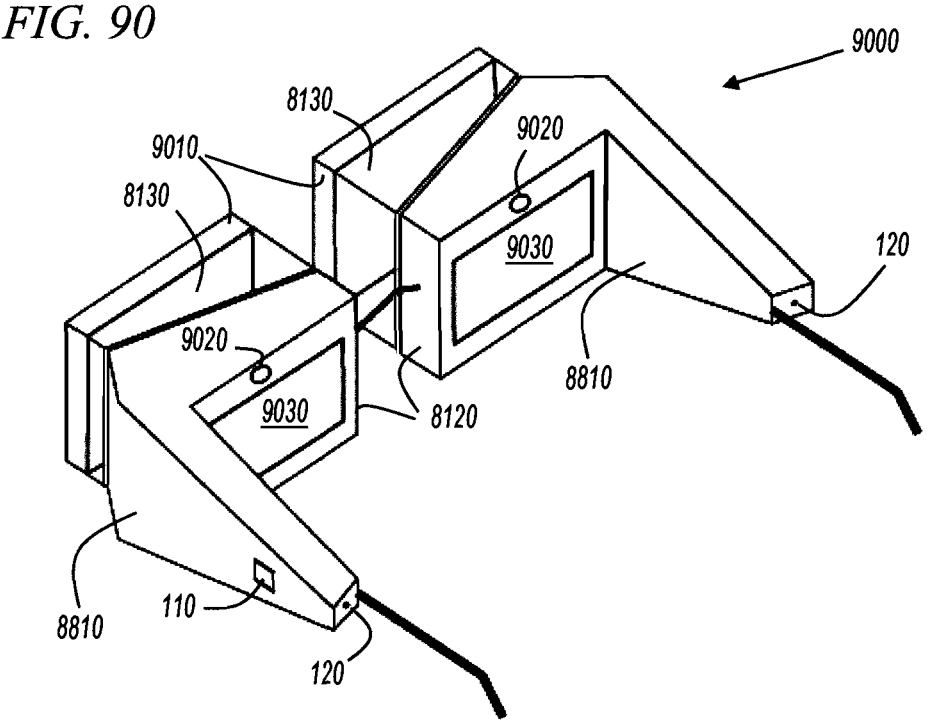
FIG. 90 shows a near-to-eye display device with a slab waveguide, wedge, component with micromirror array, SLM, and camera for eye tracking.

FIG. 90 shows a near-to-eye display device with a slab waveguide, wedge, component with micromirror array, SLM, and camera for eye tracking. Near-to-eye display device 9000 is in the form of a head-worn device, and more specifically in the shape of a pair of eyeglasses, but this is not a limitation of the present invention. In some embodiments, near-to-eye display device 9000 is a handheld device, and in other embodiments, near-to-eye display device 9000 is a fixed device that a user rests against to create a constant eye relief.

Near-to-eye display device 9000 includes slab waveguides 8810, wedges 8120, optical components 8130, optical components 9010, cameras 9020, and light sources 120. Near-to-eye display device 9000 also shows reflective SLM 110 on the slab waveguide 8810, although this is not a limitation of the present invention. Any SLM, either transmissive or reflective may be positioned anywhere as shown above in the previous figures without departing from the scope of the present invention. For example, in some embodiments, a reflective SLM is placed in optical component 9010, and in other embodiments, a transmissive SLM is placed at display area 9030.

In some embodiments, near-to-eye display device 9000 is an augmented-reality device that allows real-world light to pass through optical components 9010, 8130, and wedge 8120. In these embodiments, the real-world view is superimposed on any virtual scene created by the near-to-eye display device to create an augmented reality for the user of near-to-eye display device 9000.

In some embodiments, near-to-eye display device 9000 includes electronics to provide SLM data to the SLMs. The electronics may include a processor and memory, or may include cabling and transmission circuits to receive data from external sources. The manner in which data is provided to the SLMs is not a limitation of the present invention.

Figure 91:
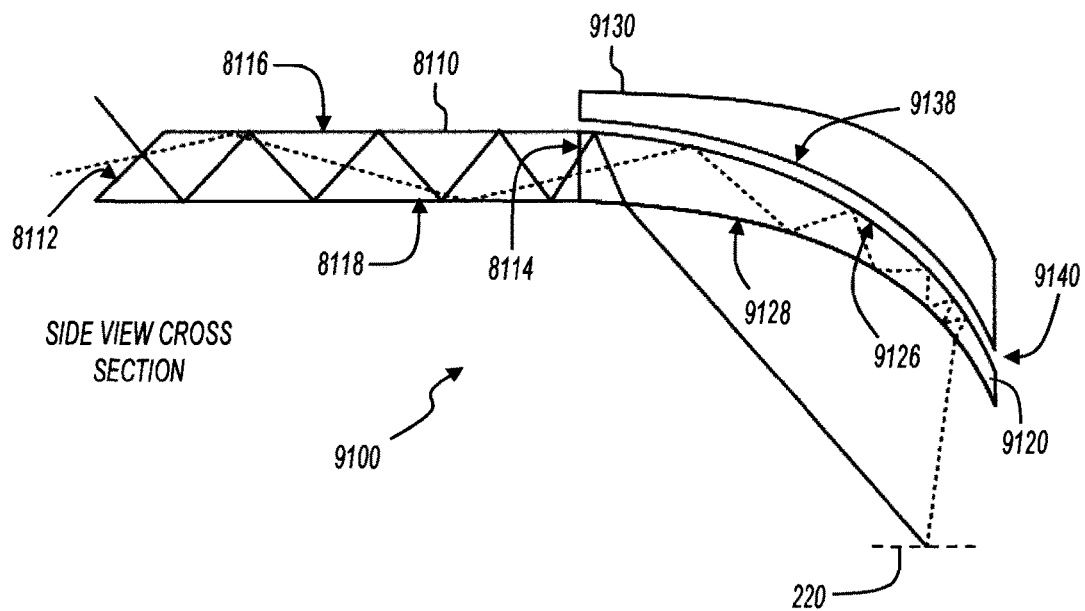
FIG. 91 shows a slab waveguide, a curved wedge, and a compensation plate.

FIG. 91 shows a slab waveguide, a curved wedge and a compensation plate. Apparatus 9100 includes slab waveguide 8110, curved wedge 9120, and curved compensation plate 9130. Slab waveguide 8110 includes input end 8112, output end 8114, first surface 8118, and second surface 8116. As described above with reference to FIG. 81, first surface 8118 and second surface 8116 are parallel to each other to cause light to propagate from input end 8112 to output end 8114 by total internal reflection.

Curved wedge 9120 is coupled to the output end 8114 of slab waveguide 8110. Curved wedge 9120 includes first curved surface 9128 and second curved surface 9126 that form a continuously decreasing thickness. In some embodiments, curved wedge is constructed from a refractive material having a graded refractive index (GRIN). The curvature of curved wedge 9120 and the gradient of the refractive index in the GRIN material are selected such that light received from slab waveguide 8110 exits curved wedge 9120 from curved surface 9128 as a converging beam that focuses on exit pupil plane 220.

Compensating wedge 9130 includes surface 9138 having substantially the same curvature as surface 9126, and is positioned to provide a uniform air gap 9140 between curved surface 9126 and surface 9138. Compensating wedge 9130 has a wedge shape that complements the shape of wedge 9120 such that light traveling through both the curved wedge and the compensating wedge travel through an equivalent amount of like-refractive material. This eliminates any prism effect that would otherwise be perceived by a user. Undistorted real-world views are provided because of the combination of the curved wedge and compensating wedge 9130.

In operation, a light beam enters slab waveguide 8110 at input end 8112 and propagates by total internal reflection within slab waveguide 8110 to output end 8114, at which point it enters wedge 9120. As the light beam propagates in curved wedge 9120, the internal angle of incidence changes due to the decreasing thickness, and the critical angle changes due to the graded refractive index, allowing the light beam to exit curved surface 9128 of curved wedge 9120 as a converging wave that focuses onto exit pupil plane 220.

Figure 92:
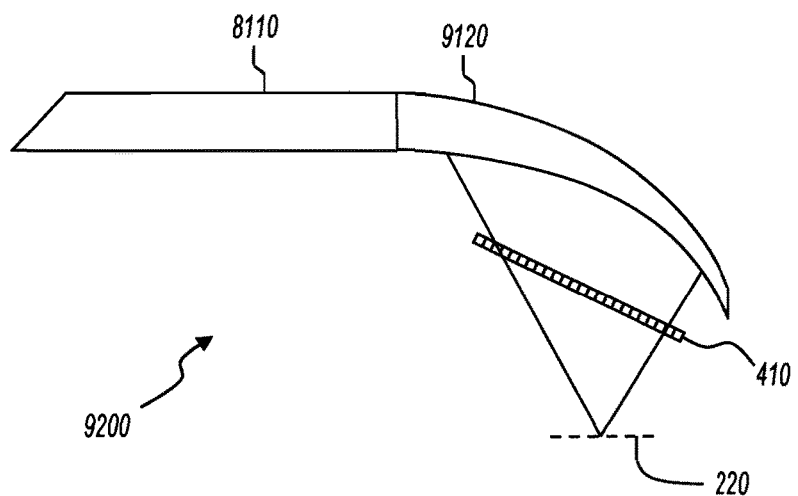
FIG. 92 shows a slab waveguide, curved wedge, and SLM in a converging beam.

FIG. 92 shows a slab waveguide, curved wedge, and SLM in a converging beam. Apparatus 9200 includes slab waveguide 8110, curved wedge 9120 and transmissive SLM 410. Transmissive SLM 410 is placed in the converging beam path and modulates the beam to create a virtual-scene light wave distribution on exit pupil plane 220. Apparatus 92 may also include a compensating wedge such as compensating wedge 9130 (FIG. 91).

Figure 93:
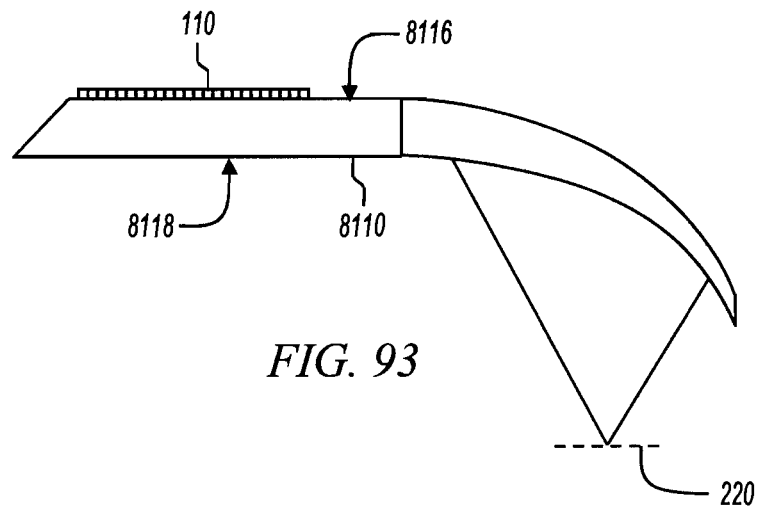
FIG. 93 shows a slab waveguide, curved wedge, and SLM on top of the slab.

FIG. 93 shows a slab waveguide, curved wedge, and SLM on top of the slab. In this configuration, the light field hits reflective SLM 110 while it is propagating in slab waveguide 8110. Although SLM 110 is shown on surface 8116 of slab waveguide 8110 in FIG. 93, this is not a limitation of the present invention. In some embodiments, the SLM is placed on surface 8118. The computer-generated hologram on the SLM modulates the light as it propagates in slab waveguide 8110, and the desired virtual scene is generated at the useful portion of exit pupil plane 220 as described above.

Figure 94:
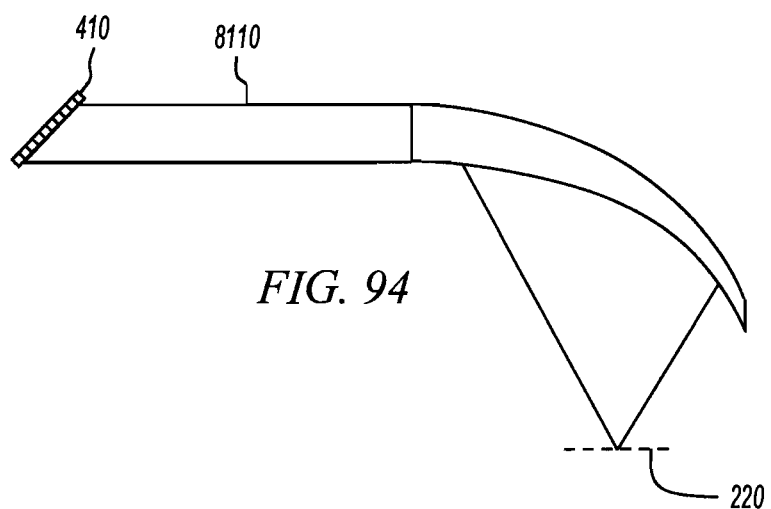
FIG. 94 shows a slab waveguide, curved wedge, and SLM at the entrance to the slab waveguide.

FIG. 94 shows a slab waveguide, curved wedge, and SLM at the entrance to the slab waveguide. FIG. 94 is similar to FIG. 93 except that SLM 410 is at the input end of the slab waveguide, and SLM 410 is transmissive.

Figure 95:
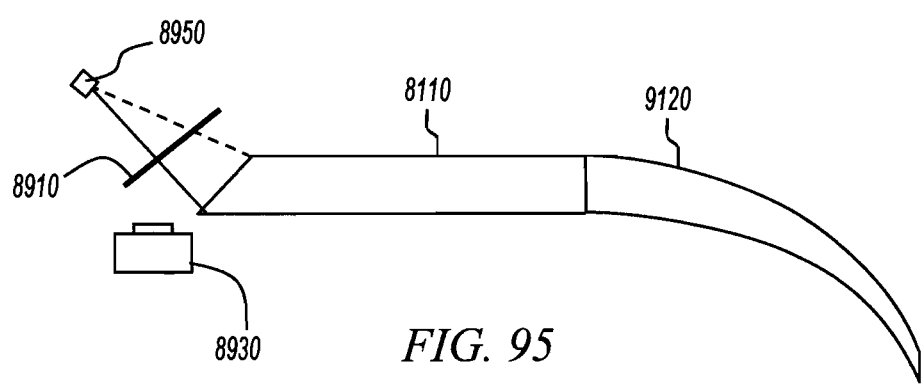
FIG. 95 shows a slab waveguide, curved wedge, and camera for eye tracking.

FIG. 95 shows a slab waveguide, curved wedge, and camera for eye tracking. An NIR illumination provided by light source 8950 is coupled into the slab after passing through a beam splitter 8910. The operation is similar to that described with respect to FIG. 89 in which the light reflected back from the eye is coupled back into the wedge 9120 and forms the image of the eye onto the camera, which can be used for eye tracking.

Camera 8930 is shown at the input to slab waveguide 8110 and coupled with a beamsplitter 8910. In some embodiments, camera 8930 is positioned along slab waveguide on either surface 8116 or 8118 similar to SLM 110 in FIG. 83.

Figure 96:
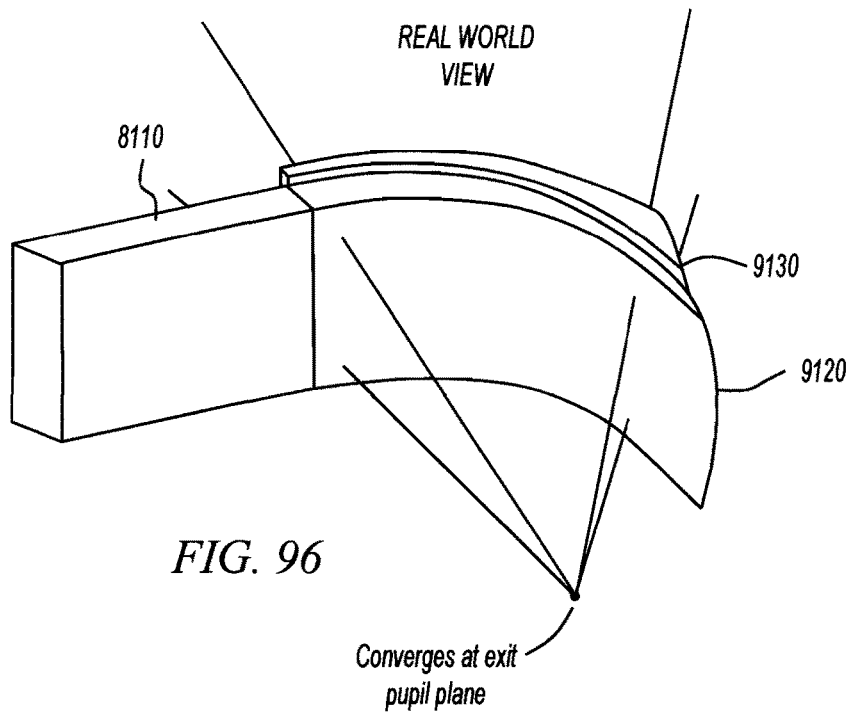
FIG. 96 shows a perspective view of the apparatus of FIG. 91.

FIG. 96 shows a perspective view of the apparatus of FIG. 91. FIG. 91 shows light representing a real-world view passing through both compensating wedge 9130 and curved wedge 9210. The real-world view may be superimposed on any modulated light distribution and presented at the exit pupil plane to form an augmented-reality display.

Figure 97:
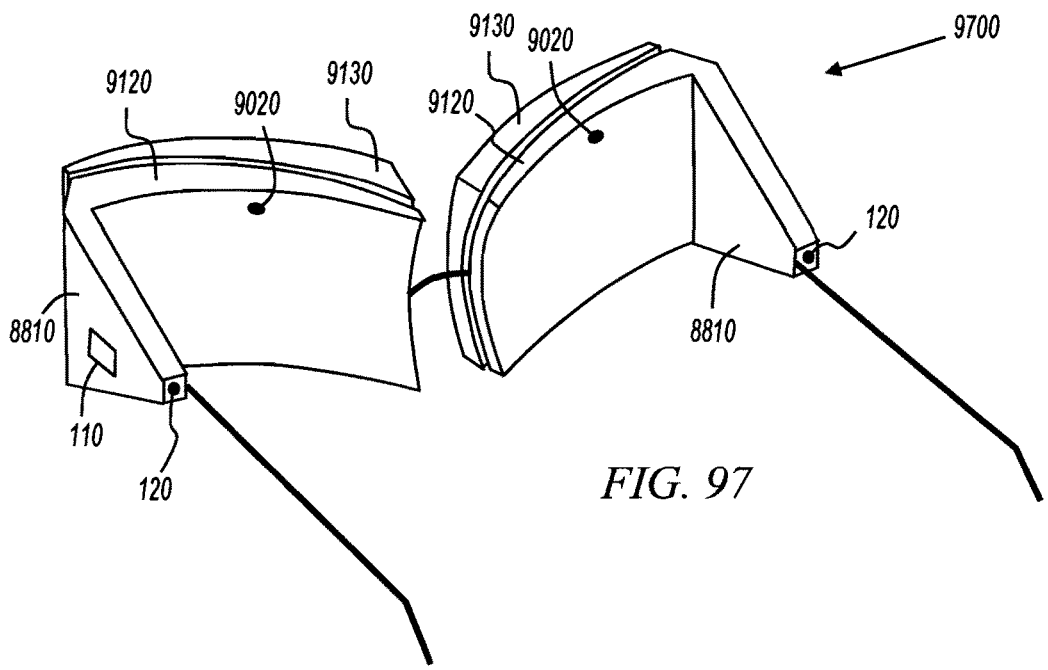
FIG. 97 shows a near-to-eye display device with a slab waveguide, curved wedge, SLM, and camera for eye tracking.

FIG. 97 shows a near-to-eye display device with a slab waveguide, curved wedge, compensating wedge, SLM, and camera for eye tracking. Near-to-eye display device 9700 is in the form of a head-worn device, and more specifically in the shape of a pair of eyeglasses, but this is not a limitation of the present invention. In some embodiments, near-to-eye display device 9700 is a handheld device, and in other embodiments, near-to-eye display device 9700 is a fixed device that a user rests against to create a constant eye relief.

Near-to-eye display device 9700 includes slab waveguides 8810, curved wedges 9120, compensating wedges 9130, cameras 9020, and light sources 120. Near-to-eye display device 9700 is shown with slab waveguides 8810 including a 90-degree bend as described above with reference to FIGS. 88 and 93. Near-to-eye display device 9700 also shows reflective SLM 110 on the slab waveguide 8810, although this is not a limitation of the present invention. Any SLM, either transmissive or reflective may be positioned anywhere as shown above in the previous figures without departing from the scope of the present invention.

In some embodiments, near-to-eye display device 9700 is a virtual-reality device that blocks the real-world view and provides the user with a virtual scene at the useful portion of the exit pupil plane. In other embodiments, near-to-eye display device 9700 is an augmented-reality device that allows real-world light to pass through the compensating wedge 9130 and the curved wedge 9120. In these embodiments, the real-world view is superimposed on any virtual scene created by the near-to-eye display device to create an augmented reality for the user of near-to-eye display device 9700.

In some embodiments, near-to-eye display device 9700 includes electronics to provide SLM data to the SLMs. The electronics may include a processor and memory, or may include cabling and transmission circuits to receive data from external sources. The manner in which data is provided to the SLMs is not a limitation of the present invention.

Figure 98:
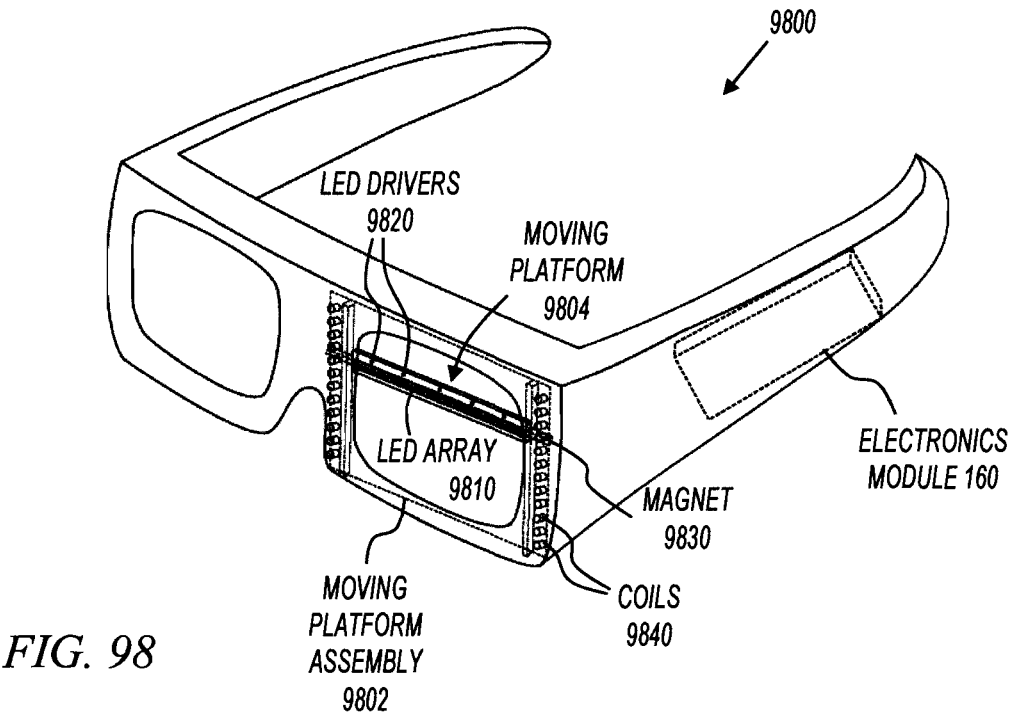
FIG. 98 shows a near-to-eye display device with a moving platform assembly.

Various embodiments of moving platform based near-to-eye display devices are now described. FIG. 98 shows a near-to-eye display device with a moving platform assembly. Near-to-eye display device 9800 includes moving platform assembly 9802 and electronics module 160. Near-to-eye display device 9800 may include many more components such as wiring, cabling, camera, and the like. These components are intentionally omitted for clarity. In addition, near-to-eye display device 9800 is shown with a moving platform assembly 9802 on only one side, whereas in practice, near-to-eye display device 9800 may have two moving bar assemblies 980—one on each side.

Moving platform assembly 9802 includes moving platform 9804 and coils 9840. Moving platform 9804 includes LED array 9810, LED drivers 9820, and magnets 9830 for actuation. LED drivers 9820 may be integrated circuits affixed to moving platform 9804. LED drivers 9820 cause individual LEDs in LED array 9810 to be illuminated in response to electrical signals received from electronics module 160. In some embodiments, LED array 9810 may be a one-dimensional array of red, green, and blue LEDs. For example, LED array 9810 may include one row of red LEDs, one row of green LEDs, and one row of blue LEDs. In other embodiments, LED array 9810 may be a two-dimensional array of red, green, and blue LEDs. For example, LED array 9810 may include multiple rows of red LEDs, multiple rows of green LEDs, and multiple rows of blue LEDs.

In operation, moving platform 9804 moves vertically across a user's field of view. Moving platform 9804 carries two permanent magnets 9830. Two linear arrays of electromagnetic coils 9840 are attached to the moving platform assembly 9802 outside the display area. Current can be passed through any given subset of the coils 9840 to actuate moving platform 9804. Electronics module 160 actuates moving platform 9804 and drives LED drivers 9820 synchronously such that a transparent image is created for a user.

The operation of moving platform assembly 9802 effectively creates an image on a transparent screen. The area occupied by the transparent screen is referred to herein as the "display area."

Figure 99:
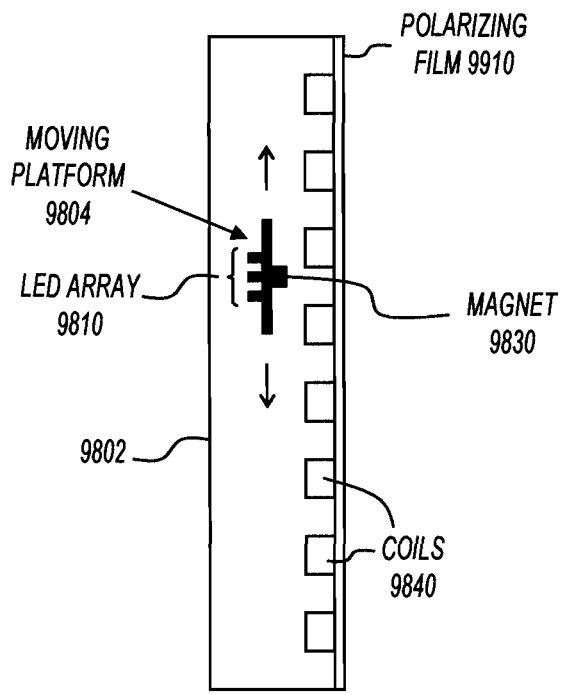
FIG. 99 shows a cross section of a moving platform assembly.

FIG. 99 shows a cross section of moving platform assembly 9802 and a polarizing film 9910. Moving platform 9804 is shown with a cross section of a one-dimensional array of LEDs. Further, the actuation in the direction of the arrows is accomplished by energizing coils 9840 in sequence so that magnet 9830 is either attracted or repulsed. The timing of coil energizing is synchronous with driving the LEDs so that an image is displayed forming an effective transparent screen for the user.

Polarizing film 9910 is oriented such that environmental light viewed by a user of near-to-eye display device 9800 passes through polarizing film 9910, and further oriented such that light produced by the plurality of light sources does not pass through the polarizing film. In some embodiments light from LED array 9810 is also polarized. In these embodiments, light passing through the polarizer is polarized in a first orientation and light emitted from the LEDs is polarized in a second orientation orthogonal to the first orientation. In some embodiments, polarizing film 9910 is omitted.

Figure 100:
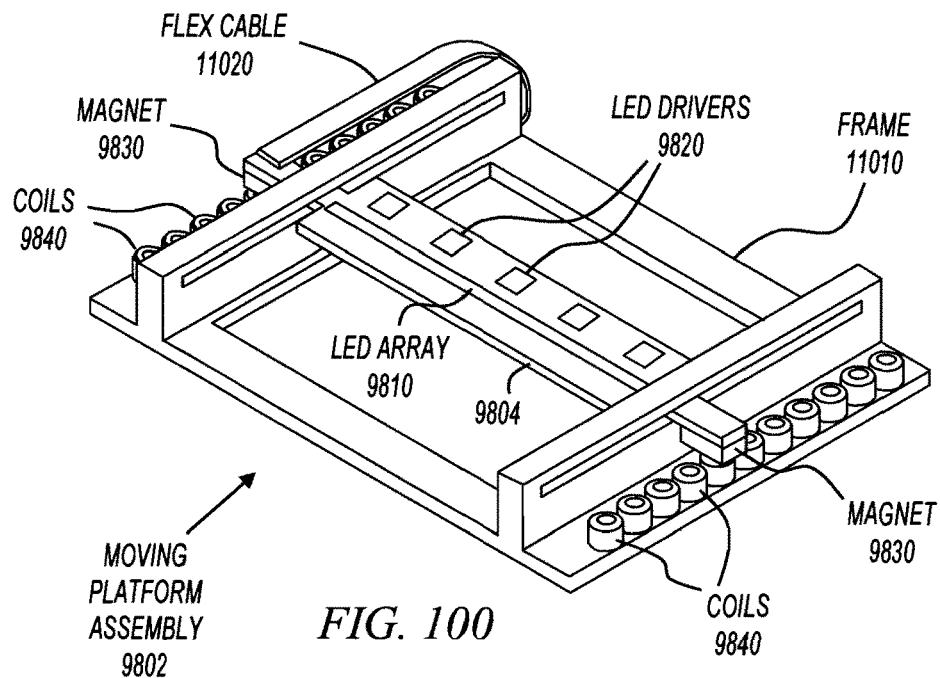
FIG. 100 shows a perspective view of a moving platform assembly.

FIG. 100 shows a perspective view of a moving platform assembly. Moving platform assembly 9802 is shown with frame 11010, coils 9840 and moving platform 9804. Frame 11010 and moving platform 9804 are shown interconnected by flex cable 11020. Flex cable 11020 carries signals from electronics module 160 (FIG. 98) to LED drivers 9820 on moving platform 9804. As shown in FIG. 100, moving platform 9804 includes one moving bar that has an array of light sources mounted thereon.

Figure 101:
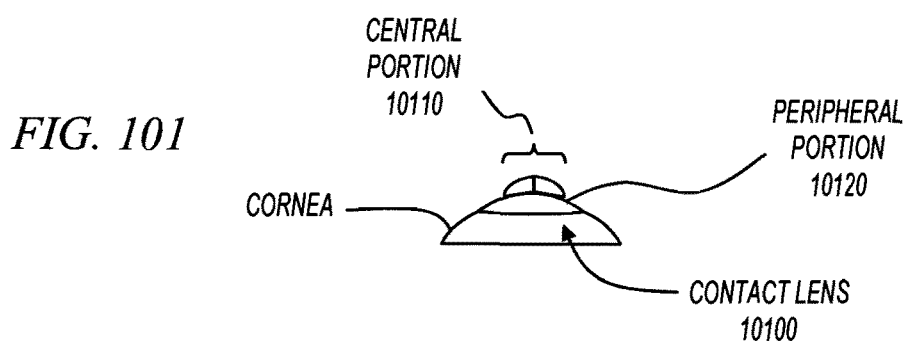
FIG. 101 shows a side view of contact lens placed on an eye.

FIG. 101 shows a side view of a contact lens placed on an eye. Contact lens 10100 includes two concentric portions, a peripheral portion 10120, and a central portion 10110. Central portion 10110 has a high-diopter lens to allow a user to focus at a plane of the plurality of light sources on moving platform 9804 when wearing near-to-eye display device 9800. Peripheral portion 10120 of the contact lens admits only light polarized in a first orientation, and central portion 10110 of the contact lens admits only light polarized in a second orientation, orthogonal to the first orientation. In some embodiments, central portion 10110 admits the polarized light emitted from LED array 9810, and peripheral portion 10120 admits the polarized light that has passed through polarizing film 9910.

Figure 102:
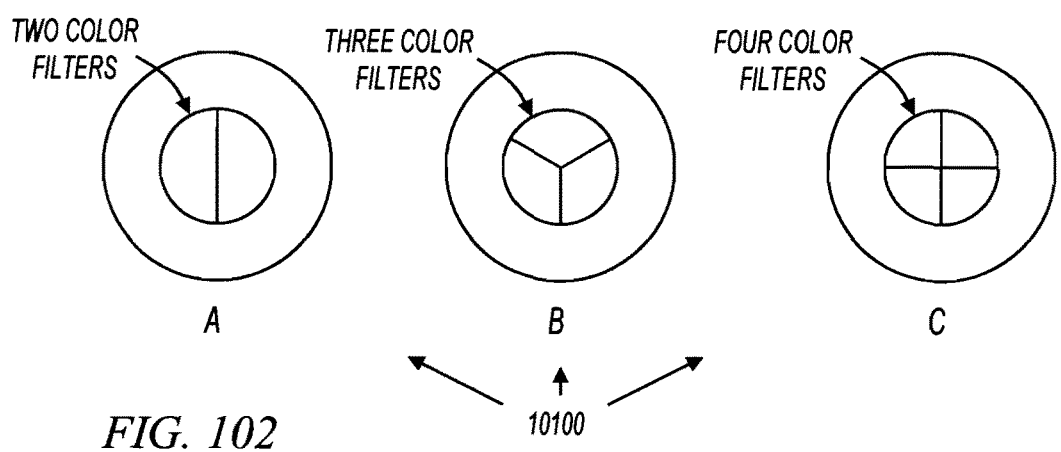
FIG. 102 shows a front view of the contact lens of FIG. 101.

FIG. 102 shows a front view of the contact lens of FIG. 101. FIG. 102 shows three different variations of contact lens 10100. Variation A has central portion 10110 split into two different parts; variation B has central portion 10110 split into three different parts; and variation C has central portion 10110 split into four different parts. In a given contact lens, each different part of central portion 10110 has a different color filter to separate different color components of the light emanating from the plurality of light sources.

Figure 103:
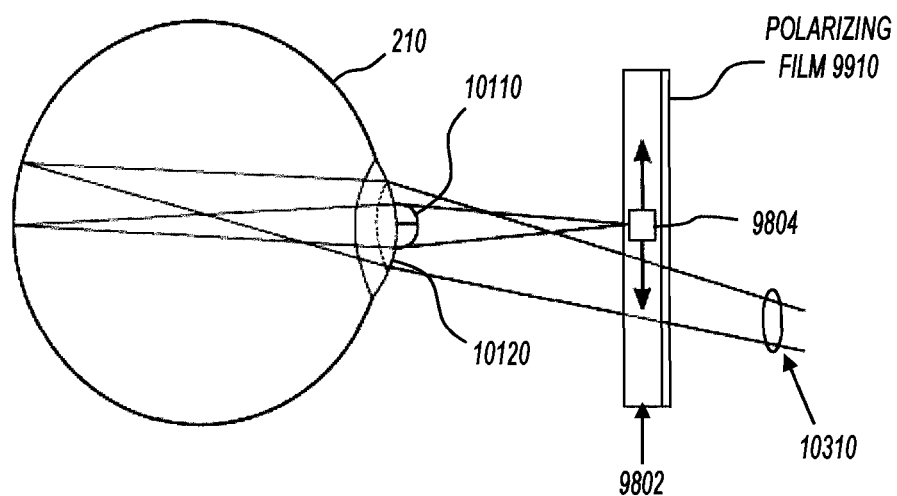
FIG. 103 shows a cross section of a contact lens on an eye and a moving platform assembly.

FIG. 103 shows a cross section of a contact lens on an eye and a moving platform assembly. Moving platform assembly 9802 includes moving platform 9804 which carries a plurality of light sources to form a transparent display for the user. The light from the surroundings, shown generally at 10310, is polarized in a first orientation by polarizing film 9910. The light from the plurality of light sources is polarized in a second orientation, orthogonal to the first orientation. The peripheral portion 10120 of the contact lens is constructed so that it only admits light with the first orientation. The central portion 10110 of the contact lens is constructed so that it only admits light with the second orientation. The central portion 10110 of the contact lens is split into multiple parts, each having a separate color filter to separate different color components of the light emanating from the plurality of light sources.

The portion of the light from the plurality of light sources that passes through the high-diopter lens in the central portion 10110 of the contact lens is properly focused in a user's eye. This allows a user to focus at a plane of the plurality of light sources. The portion of the light from the surroundings that passes through the outer portion 10120 of the contact lens allows a user to see the surroundings with the user's normal eye sight.

Figure 104:
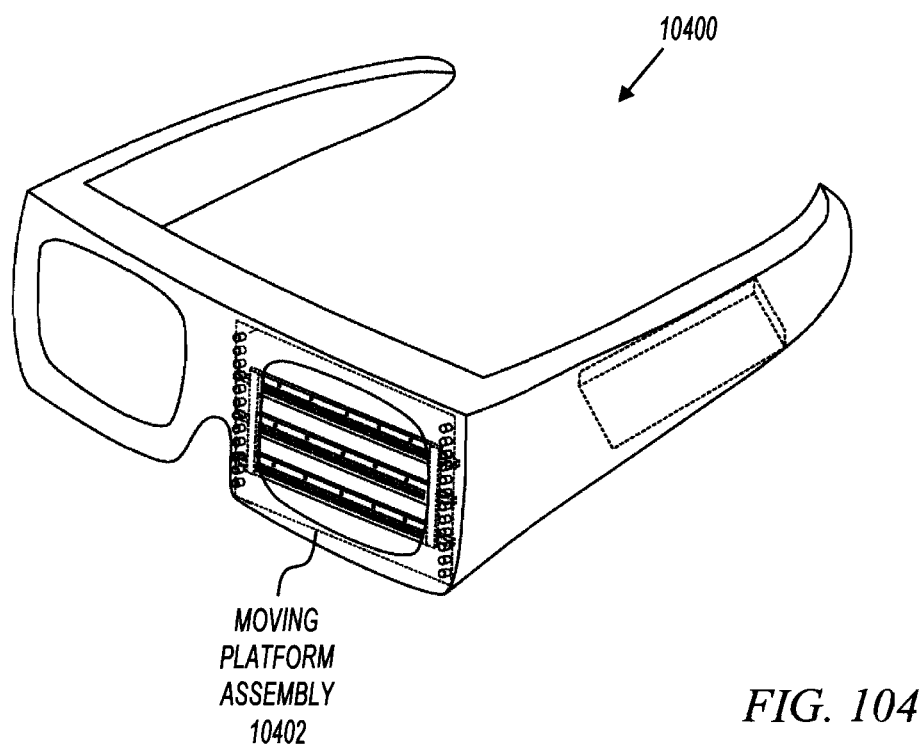
FIG. 104 shows a near-to-eye display device with a moving platform assembly.

FIG. 104 shows a near-to-eye display device with a moving platform assembly. As shown in FIG. 104, near-to-eye display device 10400 includes moving platform assembly 10402, which in turn includes a moving platform with multiple bars. In operation, the multiple moving bars move vertically together across the user's field of view as the moving platform moves. Each bar may contain a one-dimensional or two-dimensional array of light sources. Actuation is the same as described above with reference to FIGS. 98-100.

Figure 105:
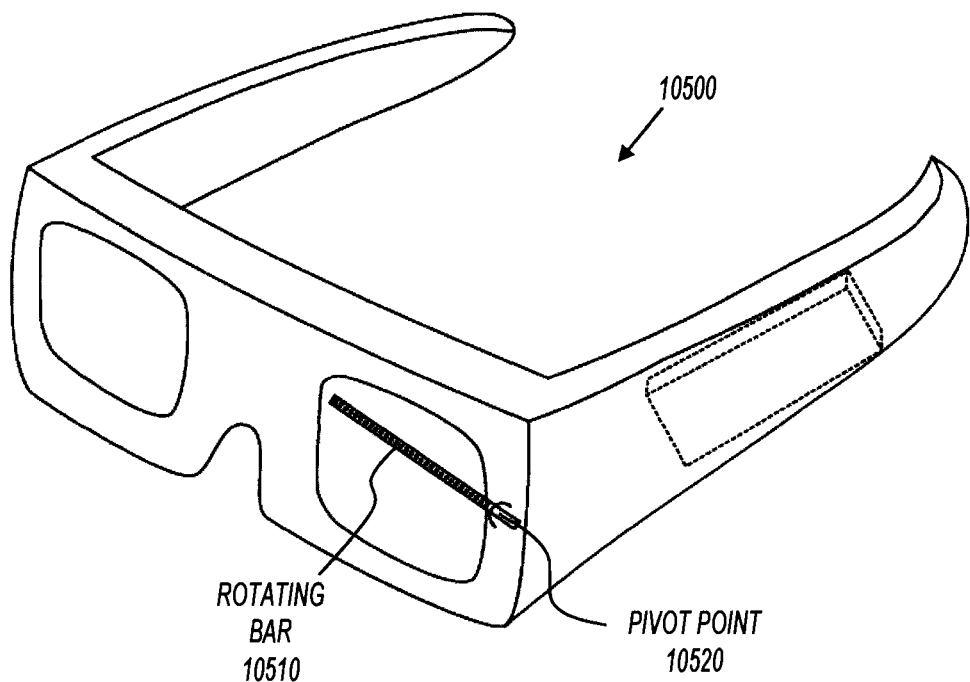
FIG. 105 shows a perspective view of a near-to-eye display device with a rotating bar.

FIG. 105 shows a perspective view of a near-to-eye display device with a rotating bar. Rotating bar 10510 includes a plurality of light sources and rotates about pivot point 10520. Rotating bar 10510 is actuated synchronously with signals that drive the light source to create an effective transparent display for the user.

Figure 106:
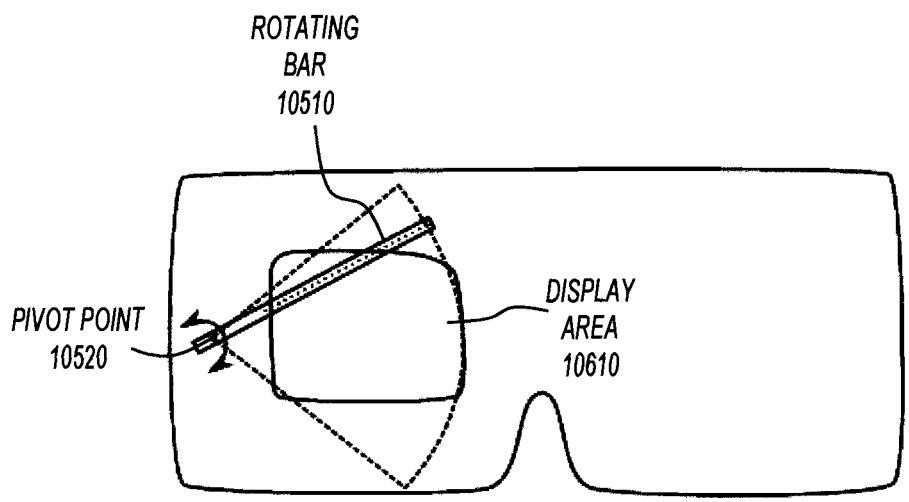
FIGS. 106-108 show front views of near-to-eye display devices with rotating bars.
Figure 107:
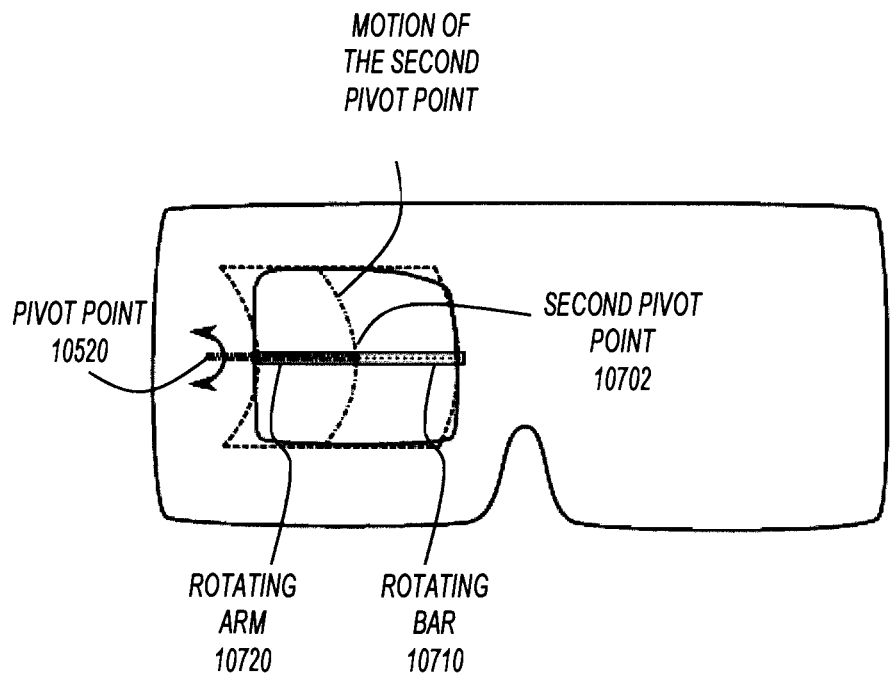
Figure 108:
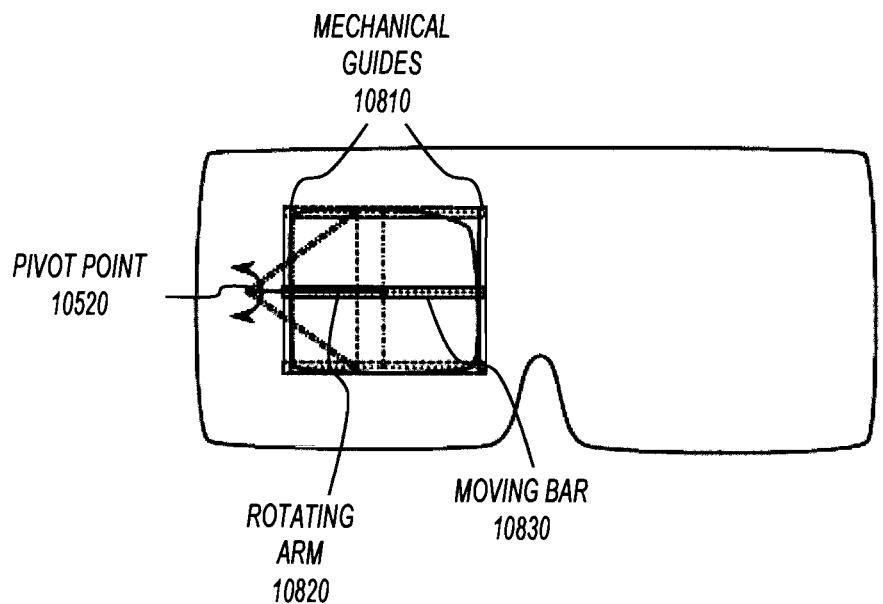

FIGS. 106-108 show front views of near-to-eye display devices with rotating bars. FIG. 106 shows a front view of near-to-eye display device 10500 with the detail shown for the right eye rather than the left eye. The rotating bar 10510 rotates about pivot point 10520 and sweeps through the display area shown at 10610. In some embodiments, the rotating bar includes a plurality of light sources as described above with reference to previous figures.

FIG. 107 shows a front view of a near-to-eye display device with a rotating bar rotating around two pivot points. The rotating bar 10710 carries a plurality of light sources. A rotating arm 10720 is rotating around a first pivot point. The rotating arm 10720 is connected to the rotating bar 10710 at the second pivot point. The rotating bar 10710 is kept at a fixed orientation throughout the motion so that the display can make a more efficient use of the motion. The dotted line outlines the potential display area.

FIG. 108 shows front view of a near-to-eye display device with a moving bar moving vertically across a user's field of view. The moving bar 10830 is actuated by a rotating arm 10820 that rotates around a pivot point 10520. The rotating arm 10820 is attached to a groove on the moving bar 10830. The rotating arm 10820 can move along the groove. The moving bar 10830 is constrained by two mechanical guides 10810 to produce a vertical motion. The moving bar 10830 carries a plurality of light sources. The dotted line outlines the potential display area.

Figure 109:
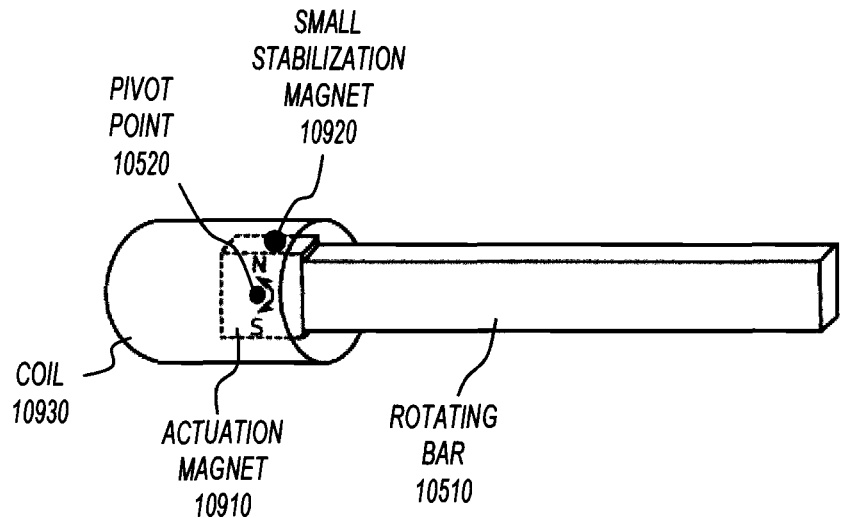
FIGS. 109 and 110 show rotating-bar-actuation embodiments.

FIG. 109 shows a rotating-bar-actuation embodiment where a permanent magnet 10910 is placed inside of an electromagnetic coil 10930. The permanent magnet 10910 is attached to the rotating bar 10510 and is suspended so that there is a pivot point 10520 inside of the electromagnetic coil 10930. When a current is passed through the electromagnetic coil 10930, the rotating bar 10510 will rotate around the pivot point 10520. A small stabilization magnet 10920 is attached to the electromagnetic coil 10930 to keep the rotating bar 10510 stable when not actuated.

Figure 110:
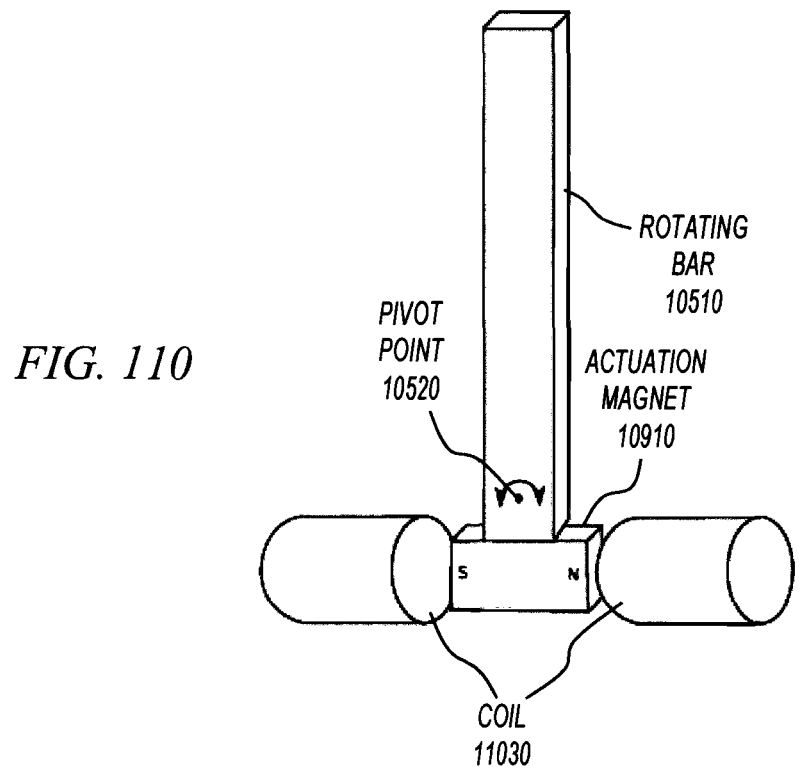

FIG. 110 shows a rotating-bar-actuation embodiment where a permanent magnet 10910 is placed between two electromagnetic coils 11030. The permanent magnet 10910 is attached to the rotating bar 10510 and is suspended so that the rotating bar 10510 will rotate around the pivot point 10520. When current is passed though the electromagnetic coils 11030, the rotating bar 10510 will rotate around the pivot point 10520. The various embodiments of the present invention are not limited to magnetic actuation. For example, in some embodiments, piezoelectric actuation is employed, and in other embodiments, actuation using a rotary or linear motor of any sort is employed.

Figure 111:
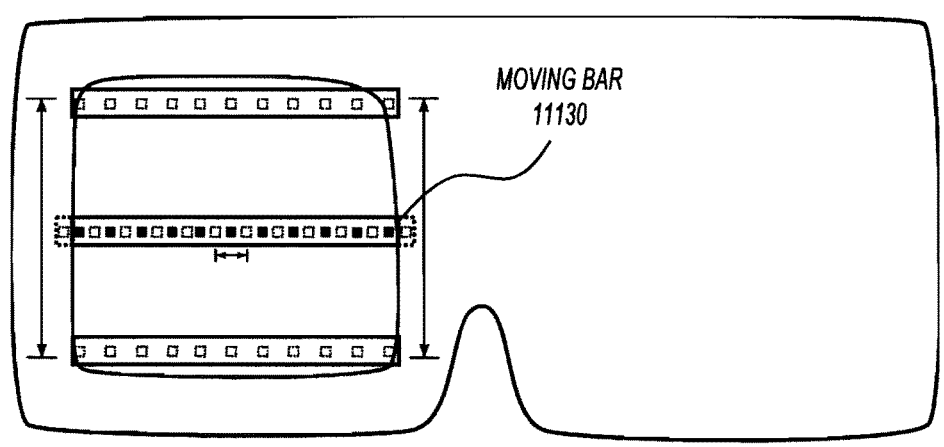
FIG. 111 shows a front view of a near-to-eye display device with a platform that moves in two dimensions.

FIG. 111 shows a front view of a near-to-eye display device with a moving bar that moves in two dimensions. The moving bar 11130 moves periodically in the vertical direction to form a transparent display for a user, and it simultaneously moves periodically a shorter distance in the horizontal direction. The purpose of the horizontal motion is to increase the horizontal display resolution above the resolution dictated by the spacing of the light sources.

Figure 112:
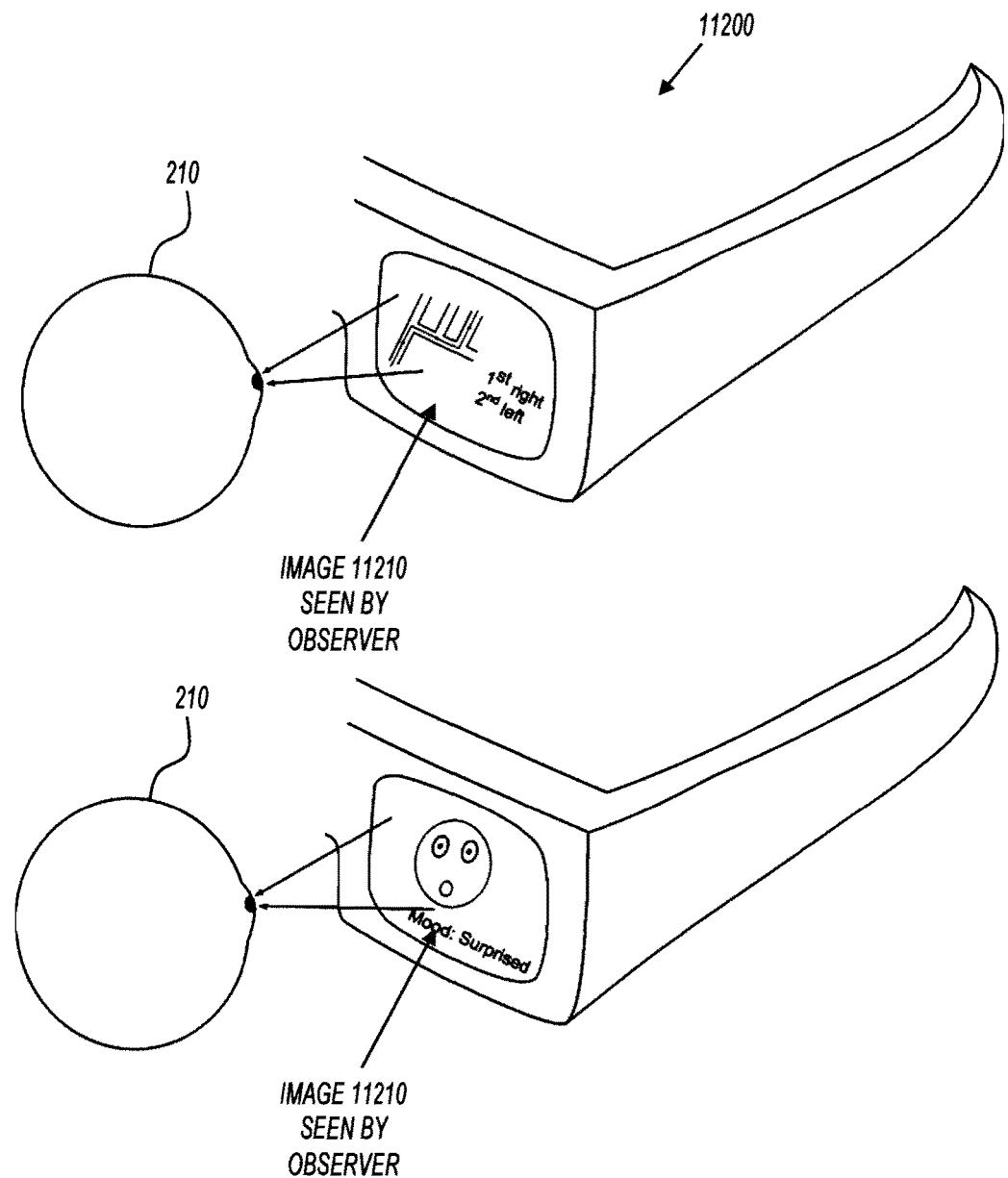
FIG. 112 shows an external display with no contact lens.

FIG. 112 shows an external near-to-eye display device 11200 with no contact lens. A moving bar (not shown) is moving across an otherwise transparent area in a near-to-eye display device. The plurality of light sources is arranged so that light from the display can reach observers other than the user of the device. If an observer views the transparent display from a distance where the observer's eyes can focus on the content on the transparent display, the observer sees image 11210. Two examples of image 11210 are shown in FIG. 112. Because image 11210 is generated with light sources that face away from the user of near-to-eye display device 11200, the user does not see image 11210.

Figure 113:
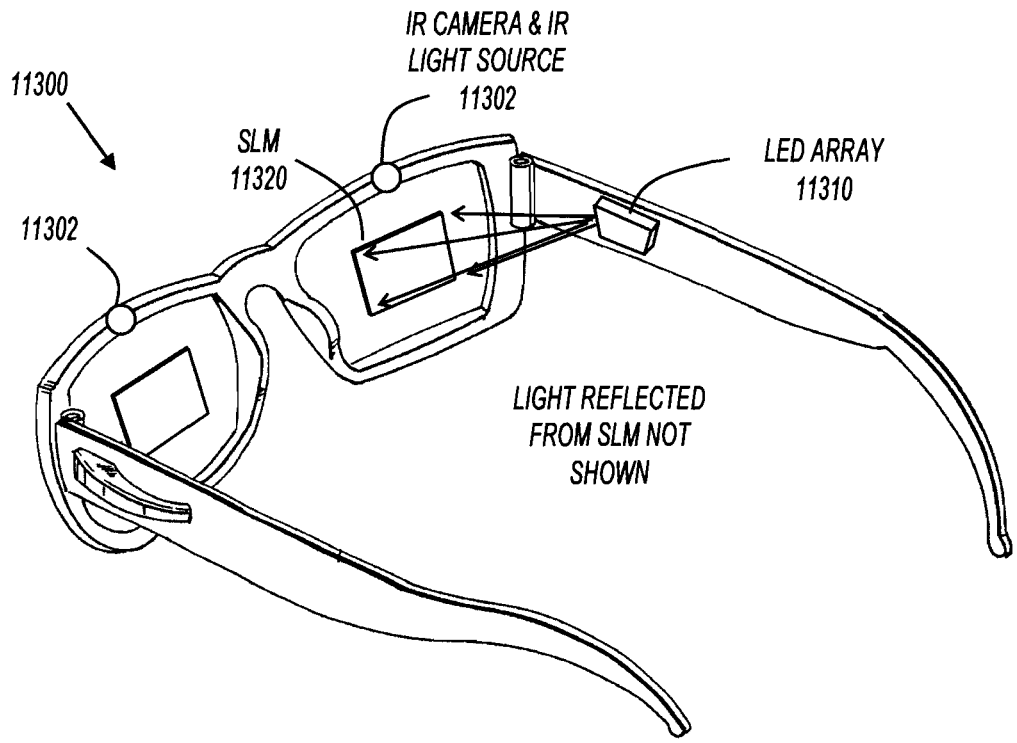
FIG. 113 shows a perspective view of near-to-eye display device that includes an LED array.

Various embodiments of pupil tracker units are now described. FIG. 113 shows a perspective view of a near-to-eye display device that includes a LED array. Near-to-eye display device 1130 includes SLM 11320, infrared (IR) camera and light source 11302, and LED array 11310. Near-to-eye display device 11300 may also include additional components, such as an electronics module, battery, cabling, and the like. These additional components are intentionally omitted from the figure so as to not obscure the components that are shown. Further, near-to-eye display device 11300, like many other near-to-eye display devices depicted herein, shows most components for only one side (one eye) of the device. In some embodiments, all components are duplicated and mirrored to create a near-to-eye display device for both eyes.

In some embodiments, the IR light sources are used to illuminate a user's pupils and the cameras are used to detect the position of the user's pupils. In some embodiments, the cameras are positioned on the frame as shown in FIG. 113, although this is not a limitation of the present invention. For example, in some embodiments cameras are mounted on a back-light unit or are coupled into an optical path as described above. Cameras for pupil tracking may be placed anywhere on any near-to-eye display device described herein without departing from the scope of the present invention. Further, in some embodiments, the IR light sources are co-located with the cameras, although this is not a limitation of the present invention. For example, in some embodiments, IR light sources are co-located with point light sources used to illuminate an SLM. As a further example, an IR light source may be co-located with LED array 11310.

In operation, the user's eyes are illuminated with infrared light, which is not visible to the user. The cameras capture infrared images of the user's eyes, and existing computer vision, pattern recognition, and image processing algorithms are used to detect the pupil positions.

Figure 114:
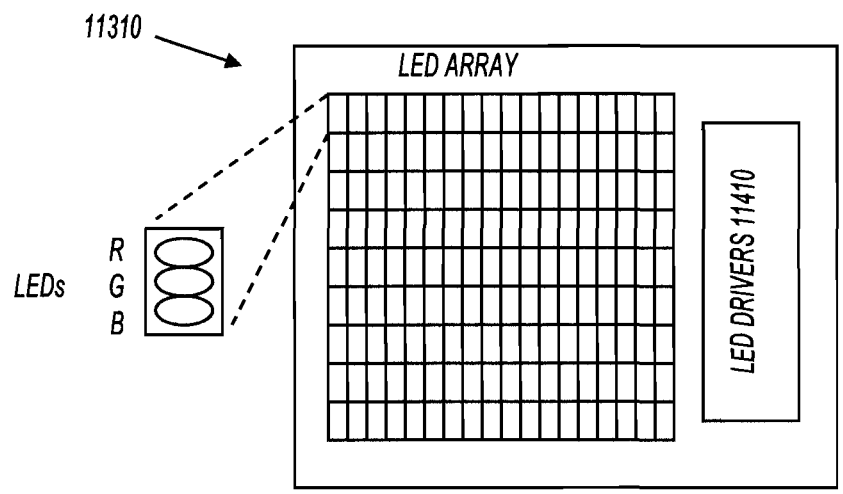
FIG. 114 shows a two-dimensional LED array.

FIG. 114 shows a two-dimensional LED array. LED array 11310 includes a two-dimensional array of color light sources, where each light source includes a red, a green, and a blue LED. LED array 11310 also includes LED drivers 11410. When different LEDs are selected to provide light to illuminate SLM 11320, the resulting virtual-scene wave moves slightly on the exit pupil plane. As described below, this phenomenon is exploited to steer the useful portion of the exit pupil plane to follow eye motion.

Figure 115:
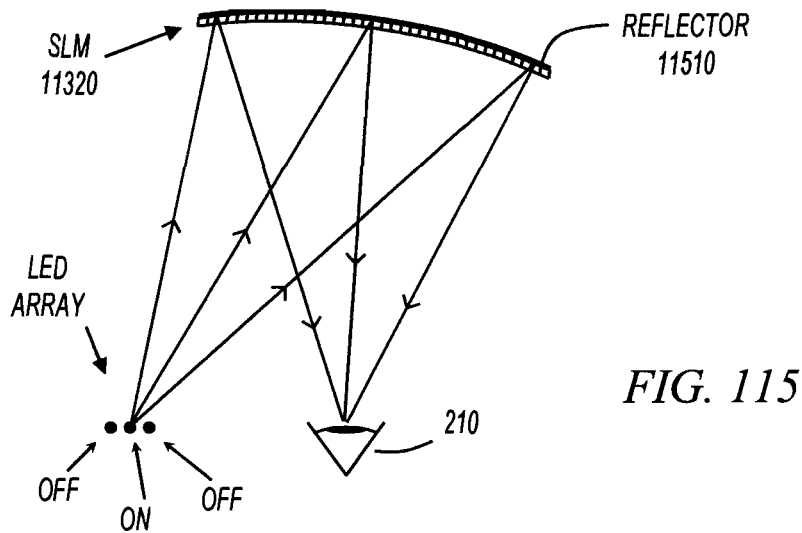
FIGS. 115 and 116 show a top view of pupil tracking using multiple LEDs.
Figure 116:
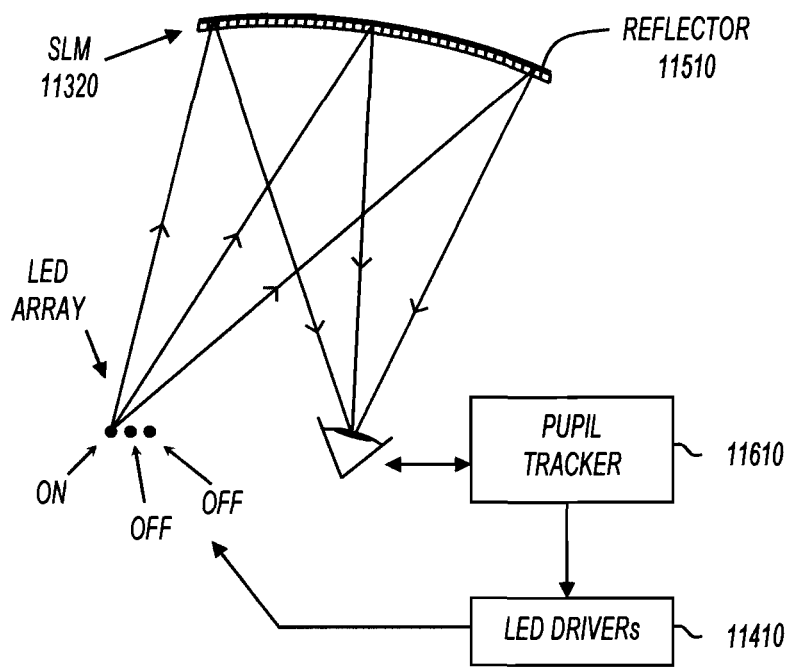

FIGS. 115 and 116 show a top view of pupil tracking using multiple LEDs. The views in FIGS. 115 and 116 depict the salient components from FIG. 113, and are not necessarily to scale. Further, FIGS. 115 and 116 show a one-dimensional array of three LEDs for simplicity, however in a practical system many more LEDs may be used, and a two-dimensional array such as that shown in FIG. 114 may be used.

SLM 11320 is a stationary SLM that includes a reflector 11510 to reflect modulated light as a converging beam. In some embodiments, SLM 11320 is a transmissive SLM in a converging or diverging light path. Further, in some embodiments, SLM 11320 is a reflective SLM in a converging or diverging light path. For example, SLM 11320 may be oriented as shown in any of FIGS. 17-28.

FIG. 115 represents the case in which the user is looking straight ahead, and the center LED is turned and used as the point light source to illuminate the SLM. FIG. 116 represents the case in which the user has moved her eye to look a few degrees to the right. Pupil tracker 11610 detects the new pupil position and commands LED driver 11410 to use a different LED to illuminate the SLM so that the useful portion of the exit pupil plane follows the user's pupil.

Pupil tracker 11610 may include light sources, cameras, a processor, instructions stored in a memory, and many other components. In some embodiments, pupil tracker 1160 is a combination of components, that when taken together, functions to track the position of the user's pupil. As the user's pupil is tracked, pupil tracker 11610 takes one or more actions to steer the useful portion of the exit pupil plane to follow the user's pupil. In the case of near-to-eye display device 11300, pupil tracker 11610 commands different LEDs to illuminate the SLM to steer the useful portion of the exit pupil plane to track the user's pupils.

Figure 117:
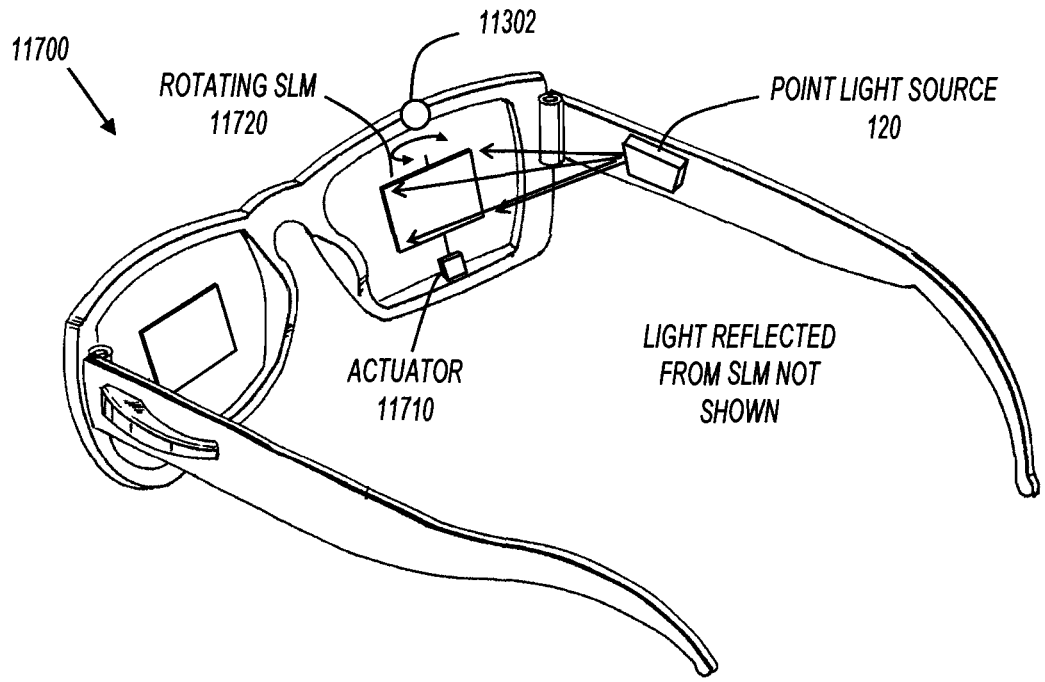
FIG. 117 shows a near-to-eye display device that includes a rotating SLM.

FIG. 117 shows a near-to-eye display device that includes a rotating SLM. Near-to-eye display device 11700 includes rotating SLM 11720, actuator 11710, camera 11302, and point light source 120. Actuator 11710, when actuated, causes SLM 11720 to rotate. In some embodiments, actuator 11710 may be a stepper motor or a like device capable of controlling the amount of rotation of the SLM. In some embodiments, actuator 11710 is commanded to operate by an electronic module (not shown) that is part of a pupil tracker such as pupil tracker 11610.

Figure 118:
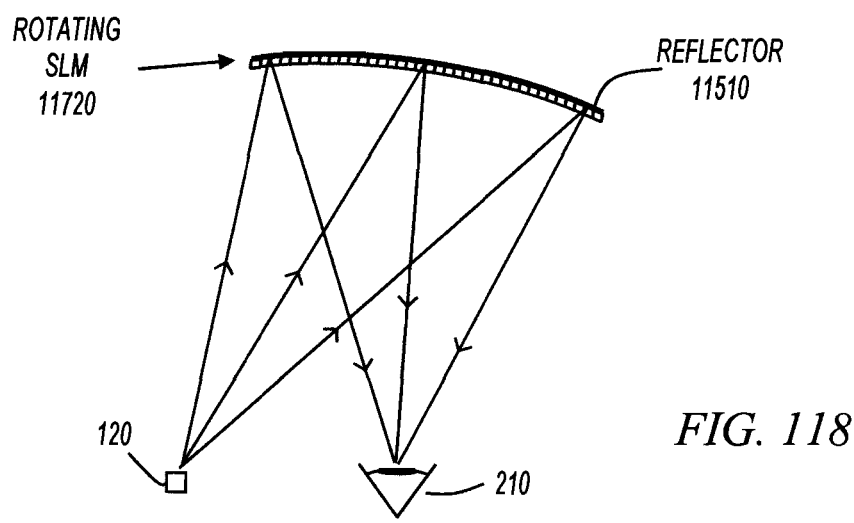
FIGS. 118 and 119 show a top view of pupil tracking using a rotating SLM.
Figure 119:
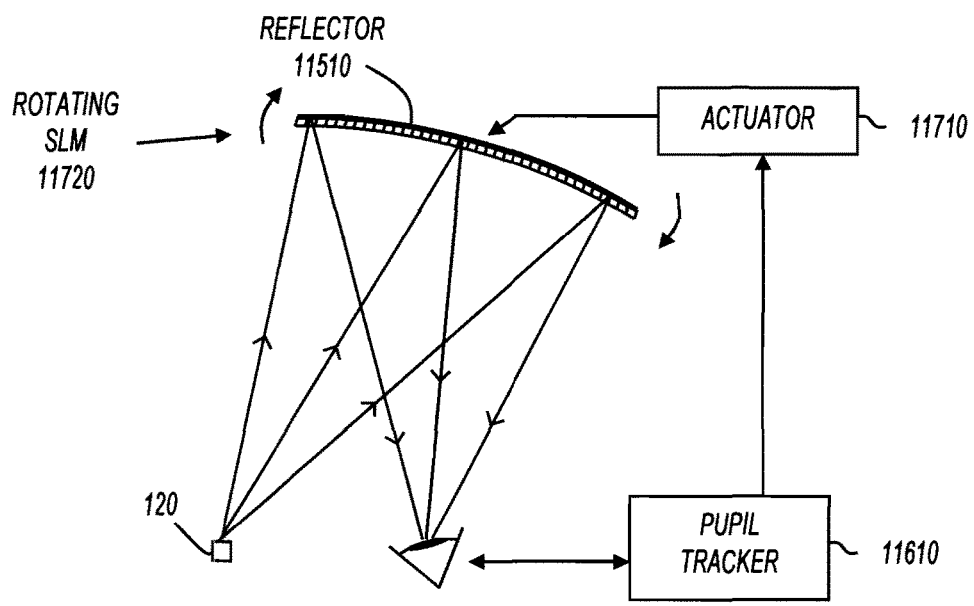

FIGS. 118 and 119 show a top view of pupil tracking using a rotating SLM. The views in FIGS. 118 and 119 depict the salient components from FIG. 117, and are not necessarily to scale. Rotating SLM 11720 includes a reflector 11510 to reflect modulated light as a converging beam. In some embodiments, SLM 11720 is a transmissive SLM in a converging or diverging light path. Further, in some embodiments, SLM 11720 is a reflective SLM in a converging or diverging light path. For example, SLM 11720 may be oriented as shown in any of FIGS. 17-28.

FIG. 118 represents the case in which the user is looking straight ahead, and the rotating SLM 11720 is oriented so that the useful portion of the exit pupil plane overlaps the user's pupil. FIG. 119 represents the case in which the user has moved her eye to look a few degrees to the left. Pupil tracker 11610 detects the new pupil position and commands actuator 11710 to rotate SLM 11720 so that the useful portion of the exit pupil plane follows the user's pupil.

As discussed above pupil tracker 11610 may take many forms, and many take any appropriate action to ensure that the useful portion of the exit pupil plane tracks the user's pupil. In the case of near-to-eye display device 11700, pupil tracker 11610 commands an actuator to rotate the SLM to steer the useful portion of the exit pupil plane to track the user's pupils.

Figure 120:
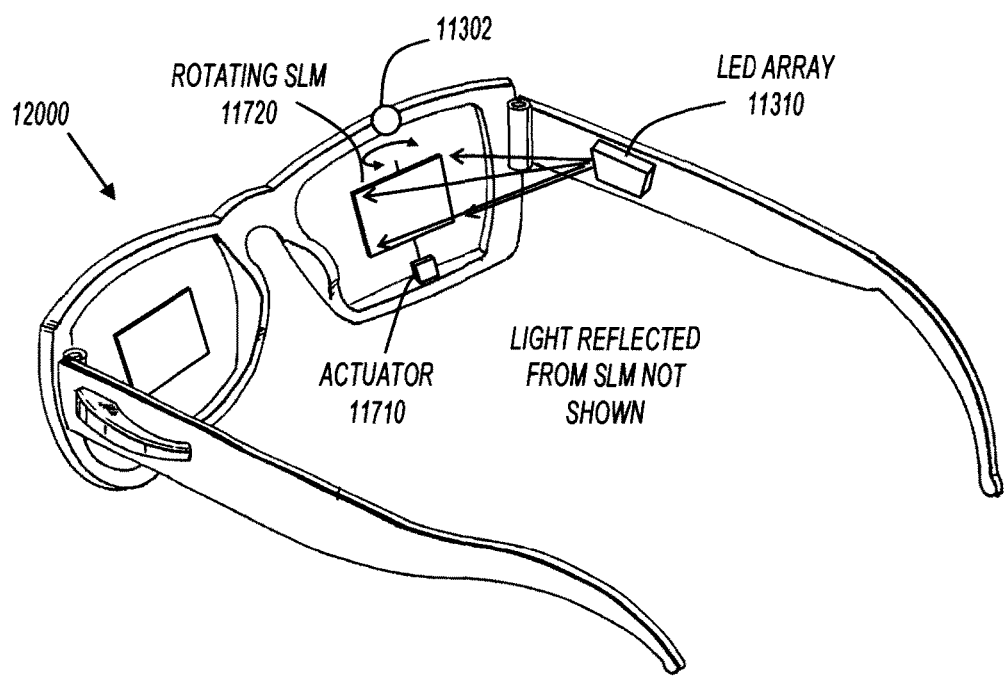
FIG. 120 shows a perspective view of a near-to-eye display device that includes rotating SLMs and LED arrays.

FIG. 120 shows a perspective view of a near-to-eye display device that includes rotating SLMs and LED arrays. Near-to-eye display device 12000 includes an LED array 11310 and rotating SLM 11720 with actuator 11710. Near-to-eye display device 12000 may rotate the SLM and select different LEDs in any combination to steer the useful portion of the exit pupil plane to the location of the user's pupil. One example is provided in FIG. 121.

Figure 121:
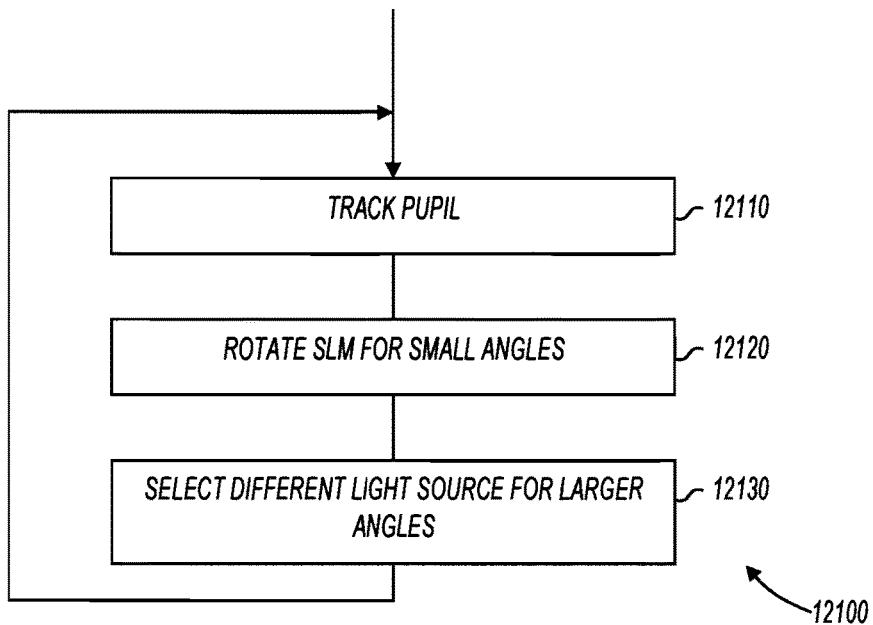
FIG. 121 shows a flowchart showing rotation for small angles and LED selection for larger angles.
Figure 122:
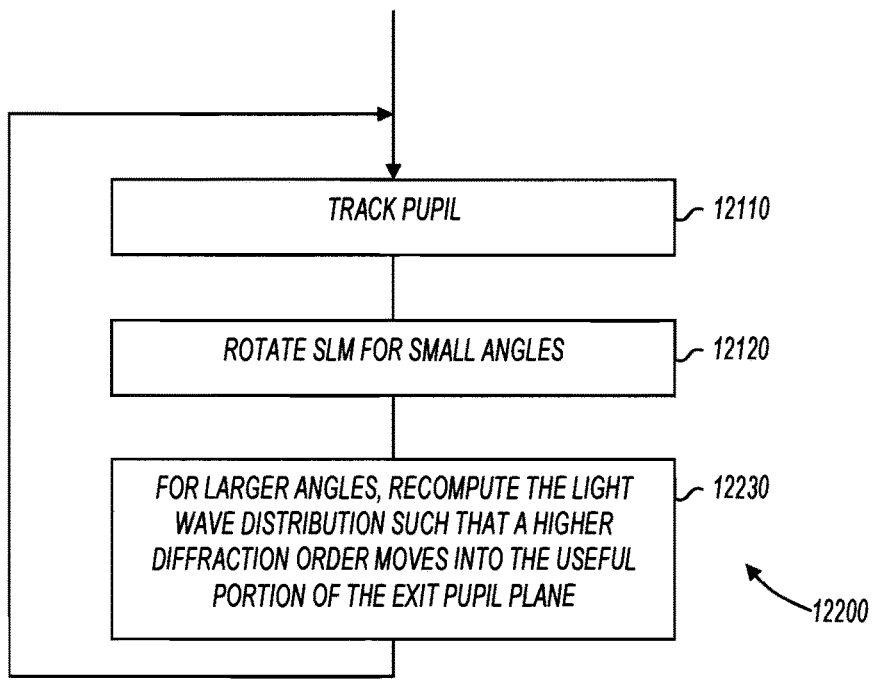
FIG. 122 shows a flowchart showing rotation for small angles and diffraction order selection for larger angles.

FIGS. 121 and 122 show flowcharts of methods in accordance with various embodiments of the invention. In some embodiments, the methods of FIGS. 121 and 122, or portions thereof, are performed by a near-to-eye display device, embodiments of which are shown in previous figures. In other embodiments, the methods are performed by a computer or an electronic system. The various actions in the methods may be performed in the order presented, or may be performed in a different order. Further, in some embodiments, some actions listed in FIGS. 121 and 122 are omitted.

FIG. 121 shows a flowchart showing rotation for small angles and LED selection for larger angles. At 12110, a user's pupil is tracked. In some embodiments, this corresponds to pupil tracker 11610 tracking the position of a user's pupil.

When a user moves her eye, the eye rotates and the pupil moves through an angle. When the pupil moves through a small angle, a rotatable SLM is rotated to steer the useful portion of the exit pupil plane to the location of the user's pupil at 12120. For larger angles, a different light source is selected to steer the useful portion of the exit pupil plane to the location of the user's pupil at 12130. This process is repeated as the user moves her eye and it is tracked by the near-to-eye display device.

FIG. 122 shows a flowchart showing rotation for small angles and diffraction order selection for larger angles. At 12110, a user's pupil is tracked. In some embodiments, this corresponds to pupil tracker 11610 tracking the position of a user's pupil.

When the pupil moves through a small angle, a rotatable SLM is rotated to steer the useful portion of the exit pupil plane to the location of the user's pupil at 12120. For larger angles, the light wave distribution is recomputed such that a higher diffraction order moves into the useful portion of the exit pupil plane at 12230. This process is repeated as the user moves her eye and it is tracked by the near-to-eye display device.

At 12110, a user's pupil is tracked. In some embodiments, this corresponds to pupil tracker 11610 tracking the position of a user's pupil.

When a user moves her eye, the eye rotates and the pupil moves through an angle. When the pupil moves through a small angle, a rotatable SLM is rotated to steer the useful portion of the exit pupil plane to the location of the user's pupil at 12120. For larger angles, a different light source is selected to steer the useful portion of the exit pupil plane to the location of the user's pupil at 12130. This process is repeated as the user moves her eye and it is tracked by the near-to-eye display device.

Figure 123:
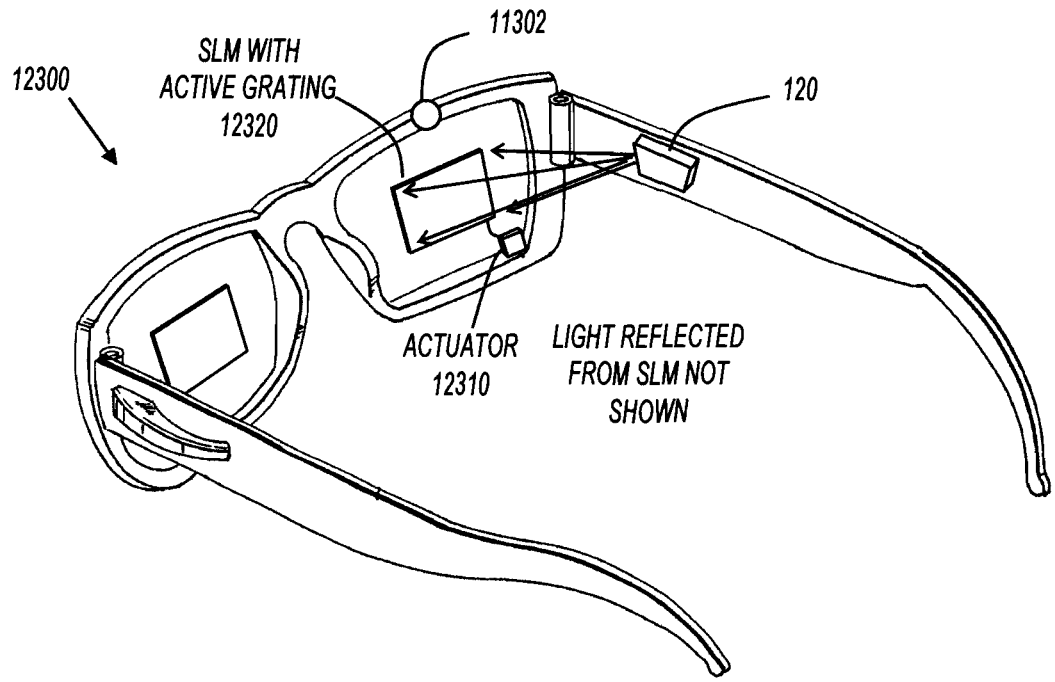
FIG. 123 shows a near-to-eye display device that includes active grating.

FIG. 123 shows a near-to-eye display device that includes an active grating. Near-to-eye display device 12300 includes SLM with active grating 12320, actuator 12310, camera 11302, and point light source 120. Actuator 12310, when actuated, causes an active grating within SLM 12320 to change its optical qualities. In some embodiments, actuator 12310 may be a driver circuit capable of controlling a voltage applied to the active grating. In some embodiments, actuator 12310 is commanded to operate by an electronic module (not shown) that is part of a pupil tracker such as pupil tracker 11610.

Figure 124:
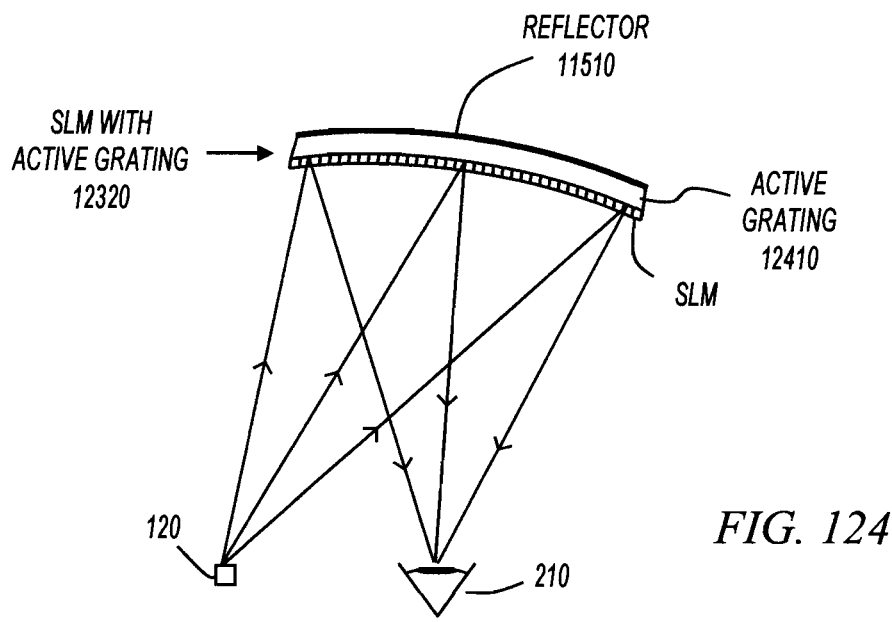
FIGS. 124 and 125 show top views of pupil tracking using an SLM and an active grating.
Figure 125:
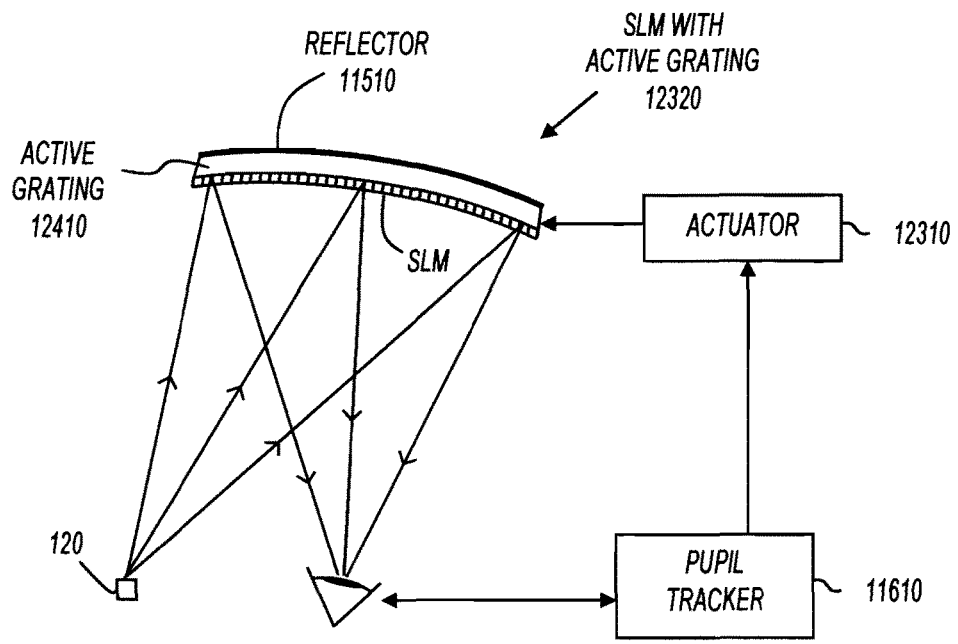

FIGS. 124 and 125 show a top view of pupil tracking using an SLM with an active grating. The views in FIGS. 124 and 125 depict the salient components from FIG. 123, and are not necessarily to scale. SLM with active grating 12320 includes active grating 12410, and a reflector 11510 to reflect modulated light as a converging beam. In some embodiments, active grating 12410 is a custom liquid crystal based device that implements a multi-section prism. Active grating 12410 may be an LC device that merely contain electrodes and no pixels.

In some embodiments, the SLM, active grating, and reflector are separate devices. In these embodiments, SLM 12320 may be a transmissive SLM in a converging or diverging light path. Further, in some embodiments, SLM 12320 is a reflective SLM in a converging or diverging light path. For example, SLM 12320 may be oriented as shown in any of FIGS. 17-28.

FIG. 124 represents the case in which the user is looking straight ahead, and active grating 12410 is controlled so that the useful portion of the exit pupil plane overlaps the user's pupil. FIG. 125 represents the case in which the user has moved her eye to look a few degrees to the right. Pupil tracker 11610 detects the new pupil position and commands actuator 12310 to energize active grating 12410 so that the useful portion of the exit pupil plane follows the user's pupil.

As discussed above pupil tracker 11610 may take many forms, and many take any appropriate action to ensure that the useful portion of the exit pupil plane tracks the user's pupil. In the case of near-to-eye display device 12300, pupil tracker 11610 commands an actuator to energize an active grating to steer the useful portion of the exit pupil plane to track the user's pupils.

Figure 126:
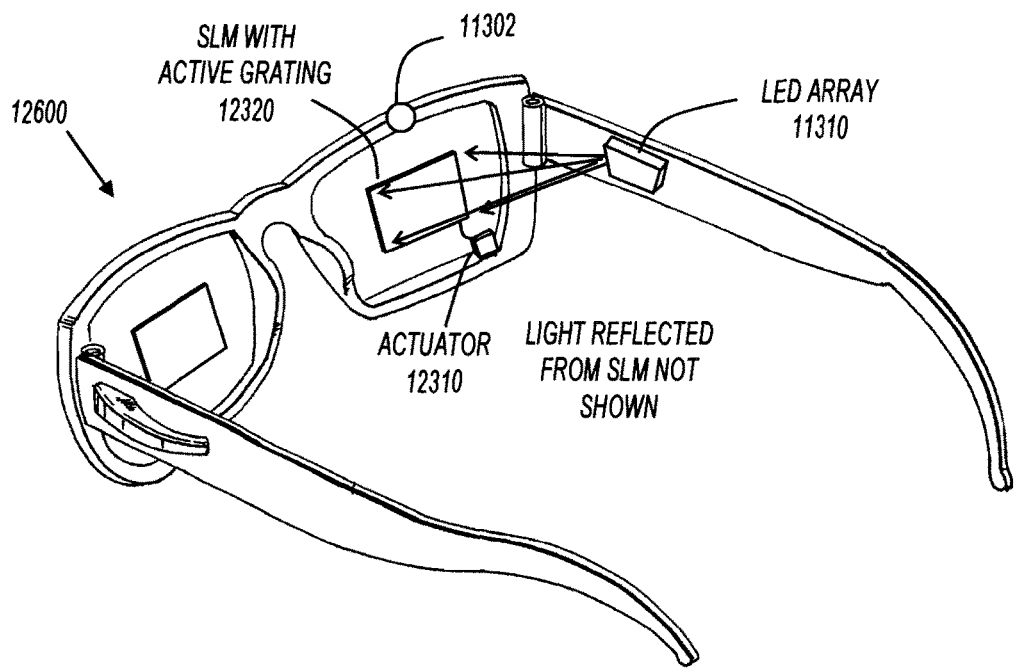
FIG. 126 shows a near-to-eye display device with a combination of an active grating and an LED array.

FIG. 126 shows a perspective view of a near-to-eye display device that includes an SLM with an active grating and LED arrays. Near-to-eye display device 12600 includes an LED array 11310 and SLM with active grating 12320 with actuator 12310. Near-to-eye display device 12600 may energize the active grating and select different LEDs in any combination to steer the useful portion of the exit pupil plane to the location of the user's pupil. One example is provided in FIG. 127.

Figure 127:
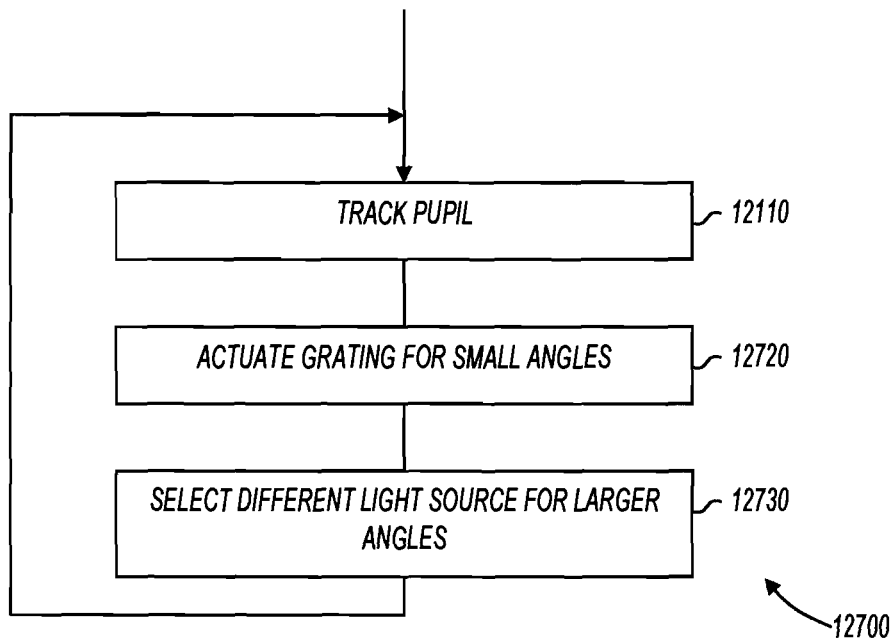
FIG. 127 shows a flowchart showing grating actuation for small angles and LED selection for larger angles.
Figure 128:
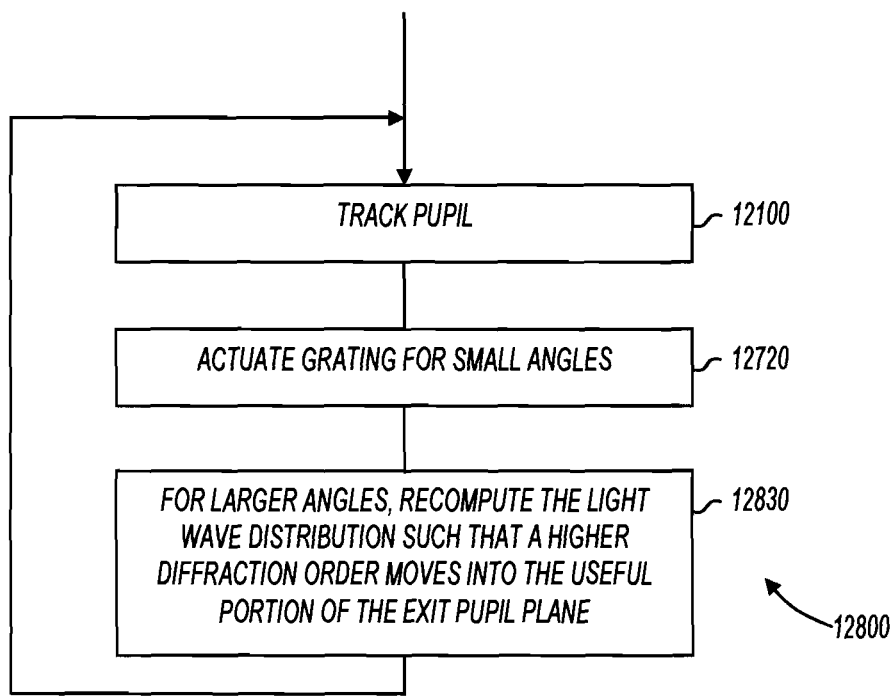
FIG. 128 shows a flowchart showing grating actuation for small angles and diffraction order selection for larger angles.

FIGS. 127 and 128 show flowcharts of methods in accordance with various embodiments of the invention. In some embodiments, the methods of FIGS. 127 and 128, or portions thereof, are performed by a near-to-eye display device, embodiments of which are shown in previous figures. In other embodiments, the methods are performed by a computer or an electronic system. The various actions in the methods may be performed in the order presented, or may be performed in a different order. Further, in some embodiments, some actions listed in FIGS. 127 and 128 are omitted.

FIG. 127 shows a flowchart showing grating actuation for small angles and LED selection for larger angles. At 12110, a user's pupil is tracked. In some embodiments, this corresponds to pupil tracker 11610 tracking the position of a user's pupil.

When a user moves her eye, the eye rotates and the pupil moves through an angle. When the pupil moves through a small angle, an active grating is actuated to steer the useful portion of the exit pupil plane to the location of the user's pupil at 12720. For larger angles, a different light source is selected to steer the useful portion of the exit pupil plane to the location of the user's pupil at 12730. This process is repeated as the user moves her eye and it is tracked by the near-to-eye display device.

FIG. 128 shows a flowchart showing grating actuation for small angles and diffraction order selection for larger angles. At 12110, a user's pupil is tracked. In some embodiments, this corresponds to pupil tracker 11610 tracking the position of a user's pupil.

When the pupil moves through a small angle, an active grating is energized to steer the useful portion of the exit pupil plane to the location of the user's pupil at 12720. For larger angles, the light wave distribution is recomputed such that a higher diffraction order moves into the useful portion of the exit pupil plane at 12830. This process is repeated as the user moves her eye and it is tracked by the near-to-eye display device.

Figure 129:
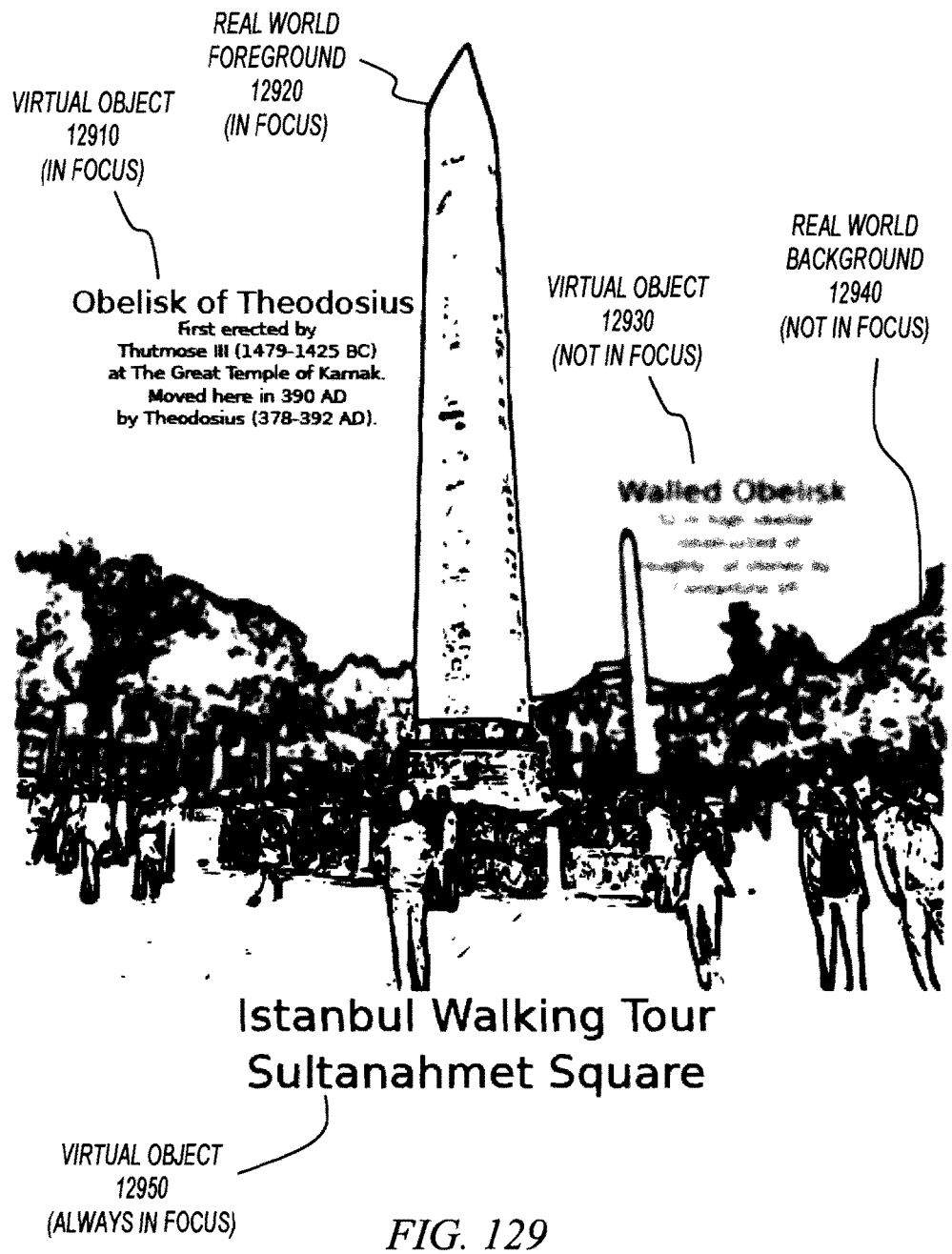
FIGS. 129 and 130 show augmented-reality views demonstrating a virtual scene at different depths.
Figure 130:
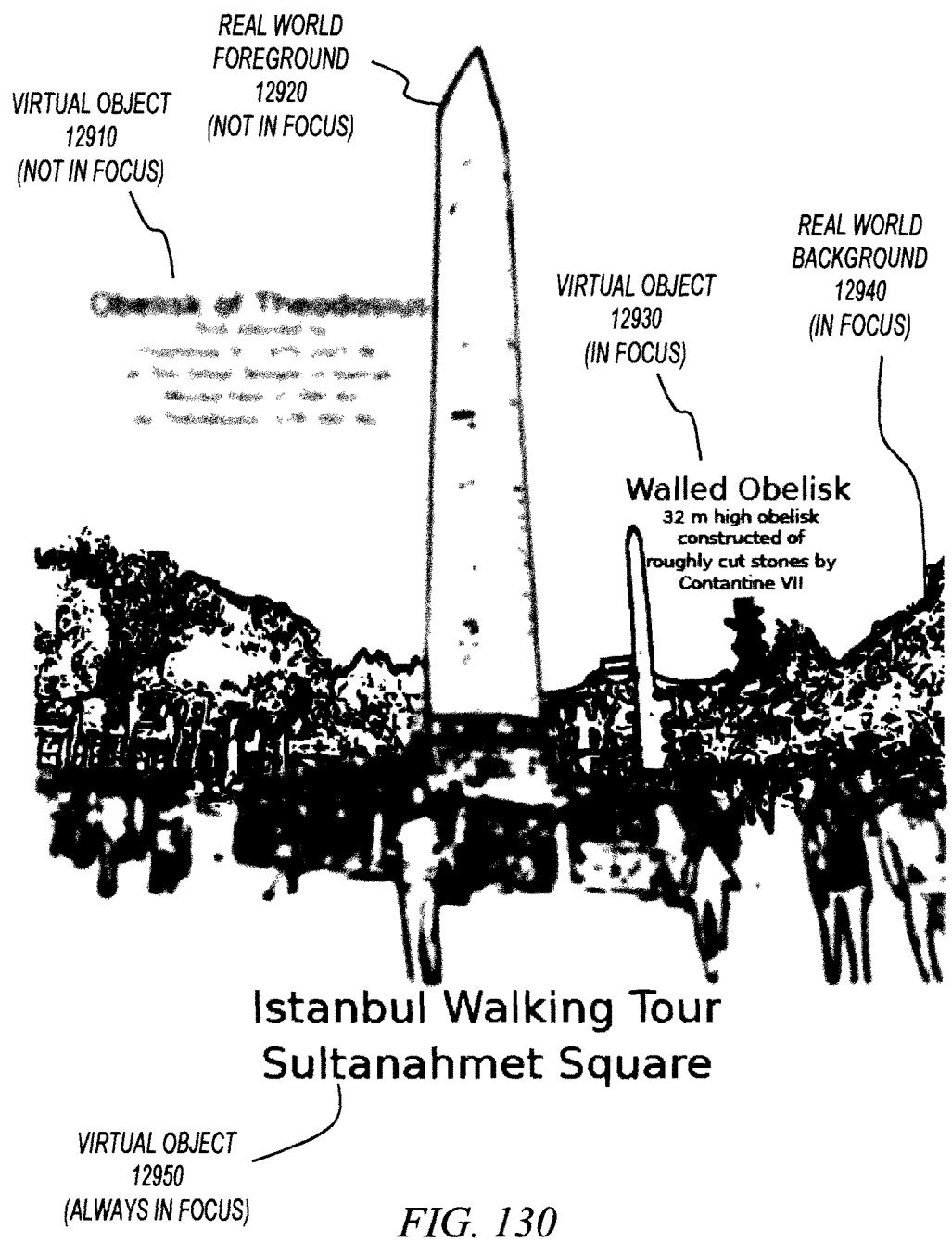

FIGS. 129 and 130 show augmented-reality views demonstrating a virtual scene at different depths. The views in FIGS. 129 and 130 represent what a user of a near-to-eye display device might see out of one eye at different accommodations. Referring now to FIG. 129, the real-world view includes objects in a foreground 12820, and objects in a background 12940. In the example of FIG. 129, the user's accommodation is set to focus on the foreground, hence the real-world foreground 12920 is shown in focus, and the real-world background 12940 is shown slightly out of focus.

FIG. 129 also shows a virtual scene that is superimposed on the real-world view. In the example of FIG. 129, the virtual scene includes three objects: virtual object 12910, virtual object 12930, and virtual object 12950. These virtual objects are simply text, however virtual objects can be anything, and are not limited to text. When the virtual scene was computed (see FIGS. 56-64), virtual object 12910 was set at a depth corresponding to the depth of the real-world foreground, and virtual object 12930 was set at a depth corresponding to the depth of the real-world background. Further, both virtual objects 12920 and 12930 are reconstructed over the entire useful portion of the exit pupil plane. This results in virtual objects 12910 and 12930 appearing focused on the user's retina only when the user accommodates to the depth of the virtual object. In the example of FIG. 129, the user has accommodated to the depth of the real-world foreground, and so virtual object 12910 is also in focus.

FIG. 130 shows the same real-world view and superimposed virtual scene as FIG. 129. The only difference is now the user has accommodated to the depth of the real-world background. As a result, both the real-world background 12940 and the virtual object 12930 are in focus, and both the real-world foreground 12920 and the virtual object 12910 are not in focus.

Note that virtual object 12950 is always in focus regardless of the user's accommodation. This is because virtual object 1250 is reconstructed over a smaller region of the useful portion of the exit pupil plane, thereby increasing the depth of field. For example, in some embodiments, the virtual scene is computed in such a way that virtual object 12950 only overlaps a one mm section of the pupil.

FIGS. 129 and 130 are an example of an SLM being programmed to display virtual objects appearing at different depths while some objects appear focused in all depths (stay in focus even if the eye accommodates to a different depth). Waves from a first plurality of subsections of the displayed virtual scene are reconstructed over the entire useful portion so that each of the first plurality of subsections appears focused on the retina only when the user accommodates to the depth of that subsection, and waves from a second subsection of the displayed virtual scene are reconstructed over smaller regions of the useful portion so that these parts always appear focused on the retina.

In some embodiments, the techniques demonstrated in FIGS. 129 and 130 are combined with binocular disparity to provide realistic 3D visual experiences without causing visual fatigue due to the accommodation-convergence conflict. When viewing 3D images using near-to-eye display devices described herein, eyes converge to the apparent position of a virtual 3D object and accommodation of each eye is also set for the depth corresponding to the apparent position of the virtual 3D object. This results in "natural 3D" in which the accommodation-convergence conflict is greatly reduced if not completely eliminated, providing a very comfortable 3D experience for the user.

Figure 131:
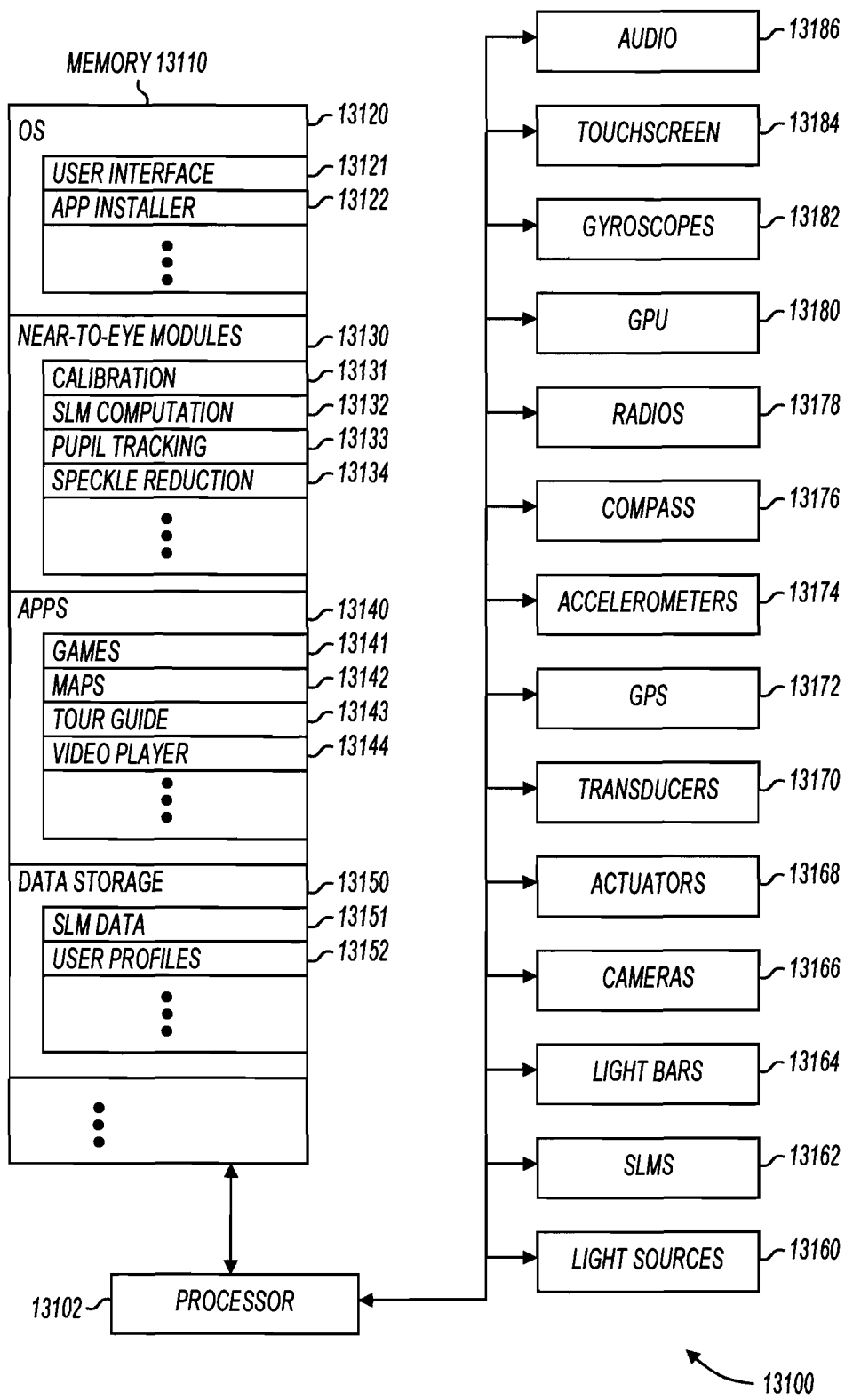
FIG. 131 shows a block diagram of a near-to-eye display device in accordance with various embodiments of the present invention.

FIG. 131 shows a block diagram of a near-to-eye display device in accordance with various embodiments of the present invention. Near-to-eye display device 13100 includes processor 13102, memory 13110, light sources 13160, SLMs 13162, light bars 13164, cameras 13166, actuators 13168, transducers 13170, global positioning system (GPS) receiver 13172, accelerometers 13174, compass 13176, radios 13178, graphics processing unit (GPU) 13180, gyroscopes 13182, touchscreen 13184, and audio circuits 13186. Near-to-eye display device 13100 may be any near-to-eye display device described herein. For example, in some embodiments, mobile device 300 may be a near-to-eye display device that performs pupil filtering, pupil tracking, speckle reduction, or any other function described herein.

Processor 13102 may be any type of processor capable of executing instructions store in memory 13110 and capable of interfacing with the various components shown in FIG. 131. For example, processor 13102 may be a microprocessor, a digital signal processor, an application-specific processor, or the like. In some embodiments, processor 13102 is a component within a larger integrated circuit such as a system on chip (SOC) application-specific integrated circuit (ASIC).

Light sources 13160 may include any type of light source capable of illuminating an SLM. Examples include point light source 120 (FIG. 1), illumination optics module 440 (FIG. 4), and the array of point light sources shown in FIGS. 15 and 16. In operation, processor 13102 may command light sources 13160 to turn on and off.

SLMs 13162 are SLMs that impart information to an illumination wave to create the desired light wave distribution in the useful portion of the exit pupil plane. In operation, processor 13102 programs SLMs 13162 using data stored in memory 13110. In some embodiments, processor 13102 computes the SLM data to be displayed on the SLM and stores it in memory 13110. In other embodiments, the SLM data is computed by a separate device, and the SLM data is provided to near-to-eye display device 13100 for later display.

Light bars 13164 include any of the light bar and/or moving platform embodiments described herein. In operation, processor 13102 may command an actuator to cause one or more light bar to move. Further processor 13102 may also command one or more light sources on a light bar to illuminate.

Cameras 13166 may be any type of camera capable of capturing an image and providing the image data to processor 13102. For example, in some embodiments, cameras 13166 are cameras used for calibration, and in other embodiments, cameras 13166 are cameras used for pupil tracking.

Actuators 13168 are devices that convert one form of energy to another. For example, actuators 13168 may include stepper motors, magnets, electrical coils, and the like. Actuators 13168 may include any of the actuator embodiments described herein.

Transducers 13170 are devices that convert energy from one form to electricity. For example, adjustment knob 4510 (FIG. 45) is an example of a transducer. In operation, processor 13102 receives electronic signals when a user interacts with any of transducers 13170.

GPS 13172 includes a GPS receiver. In operation, processor 13102 receives fine location data from GPS 13172. In some embodiments, this data is used to generate SLM data or to determine what stored SLM data should be displayed. For example, in embodiments represented FIGS. 120 and 130, GPS data may be used to determine what virtual objects should be included in the virtual scene.

Accelerometers 13174 are devices that measure rate of change of motion or the direction of forces applied to near-to-eye display device 13100 due to gravity. In operation, processor 13102 receives accelerometer data when near-to-eye display device 13100 is moved or its orientation is changed.

Compass 13176 is a device that measures the orientation of near-to-eye display device 13100 relative to magnetic north. In operation, processor 13102 receives data from compass 13176 that represents the orientation of near-to-eye display device 13100 with respect to magnetic north.

Radios 13178 may include any type of radio that can provide communications capability to near-to-eye display device 13100. For example, radio 13178 may be a cellular radio, a Bluetooth radio, a NFC radio, a WiFi radio, or the like.

Graphics processing unit (GPU) 13180 is a device that can accelerate some computations performed during the generation of SLM data. For example, GPU 13180 may be used to render a virtual scene represented by polygon mesh models.

Gyroscopes 13182 provide high-resolution data regarding movement of near-to-eye display device. In operation, processor 13102 may make use of data provided by gyroscopes 13182 for head-tracking applications.

Touchscreen 13184 allows user interaction with the display surfaces of near-to-eye display device 13100. An example near-to-eye display device with a touchscreen interface is described below with reference to FIG. 132. Touchscreen 13184 is a device that includes a touch-sensitive surface, sensor, or set of sensors that accept input from a user. For example, touchscreen 13184 may detect when and where an object touches the screen, and may also detect movement of an object across the screen. Touchscreen 13184 may be manufactured using any applicable display technologies, including for example, liquid crystal display (LCD), active matrix organic light emitting diode (AMOLED), and the like. Further, touchscreen 13184 may be manufactured using any application touch-sensitive input technologies, including for example, capacitive and resistive touch screen technologies, as well as other proximity sensor technologies.

Audio circuits 13186 provide an audio interface (input, output, or both) between processor 13102 and a user. In some embodiments, one or more applications make use of audio circuits 13186 to provide a multi-sensory experience. For example, tour-guide application 13143 may provide interpretive audio as well as an immersive 3D augmented-reality experience. In other embodiments, audio circuits 13186 include a microphone that allows a user to record audio or to provide audio commands to near-to-eye display device 13100.

Memory 13110 may include any type of memory device. For example, memory 13110 may include volatile memory such as static random-access memory (SRAM), or nonvolatile memory such as FLASH memory. Memory 13110 is encoded with (or has stored therein) one or more software modules (or sets of instructions), that when accessed by processor 113102, result in processor 13102 performing various functions. In some embodiments, the software modules stored in memory 13110 may include an operating system (OS) 13120, near-to-eye modules 13130 and applications 13140. Applications 13140 may include any number or type of applications. Examples provided in FIG. 131 include games 13141, maps 13142, a tour-guide app 13143, and a video player. An example display from a tour-guide app is described above with reference to FIGS. 129 and 130. Memory 13110 may also include any amount of space dedicated to data storage 13150.

Operating system 13120 may be any to of operating system such as an operating system to control a mobile phone, tablet computer, embedded system, or the like. As shown in FIG. 131, operating system 13120 includes user interface component 13121 and application-installer component 13122. Operating system 13120 may include many other components without departing from the scope of the present invention.

User interface component 13121 includes processor instructions that cause near-to-eye display device 13100 to display user interaction components, such as dialog boxes, alerts, and prompts. User interface 13121 also includes instructions to display menus, move icons, and manage other portions of the display environment.

Application-installer component 13122 installs applications to near-to-eye display device 13100. Any type or number of applications may be installed. Example apps currently installed on near-to-eye display device include games 13141, maps 13142, tour-guide app 13143, and video-player app 13144.

Near-to-eye modules 13130 include calibration 13131, SLM computation 13132, pupil tracking 13133, and speckle reduction 13134. Calibration module 13131 includes instructions that cause processor 13102 to perform calibration embodiments described herein. For example, calibration module 13131 may cause processor 13102 to capture images using cameras 13166, and interact with the user using user interface 13121 and transducers 13170. SLM computation module includes instructions to perform the computations described above with reference to FIG. 56. The near-to-eye modules shown in FIG. 131 are meant as examples only; many more near-to-eye modules may be included without departing from the scope of the present invention. In general, any method described herein may include a module component within near-to-eye modules 13130.

Pupil-tracking module 13133 includes instructions that when executed by processor 13102 cause near-to-eye display device 13100 to steer the useful portion of the exit pupil plane to follow a user's pupils. In some embodiments, the combination of pupil-tracking module 13133, processor 13102, cameras 13166, and light sources 13160 (for IR light) make up pupil tracker 11610 described above.

Speckle reduction module 13134 includes instruction that when executed by processor 13102 causes a virtual scene to be computed with assigned phase terms that reduce speckle.

Data storage 13150 stores data that does not include processor instructions. For example, SLM data 13151 is stored in data storage 13150, as are user profiles. In some embodiments, SLM data 13151 includes still images, and in other embodiments, SLM data 13151 includes many frames that form video data. Further, SLM data 13151 may represent 2D or 3D virtual scenes used for either or both of virtual-reality-display applications or augmented-reality applications.

Each of the above-identified applications and modules correspond to a set of instructions for performing one or more functions described above. These applications (sets of instructions) need not be implemented as separate software programs, procedures or modules, and thus various subsets of these applications may be combined or otherwise re-arranged in various embodiments. For example, SLM computation 13132 may be combined with speckle reduction 13134. Furthermore, memory 13110 may store additional applications (e.g., audio players, camera applications, etc.) and data structures not described above.

It should be noted that device 13100 is presented as an example of a near-to-eye display device, and that device 13100 may have more or fewer components than shown, may combine two or more components, or may have a different configuration or arrangement of components. For example, device 13100 may include many more components such as sensors (optical, touch, proximity etc.), or any other components suitable for use in a near-to-eye display device.

Memory 13110 represents a computer-readable medium capable of storing instructions, that when accessed by processor 13102, result in the processor performing as described herein. For example, when processor 13102 accesses instructions within pupil-tracking module 13133, processor 13102 analyzes images of a user's eyes, determines the pupil location, and then steers the useful portion of the exit pupil plan to overlap with the user's pupil.

Figure 132:
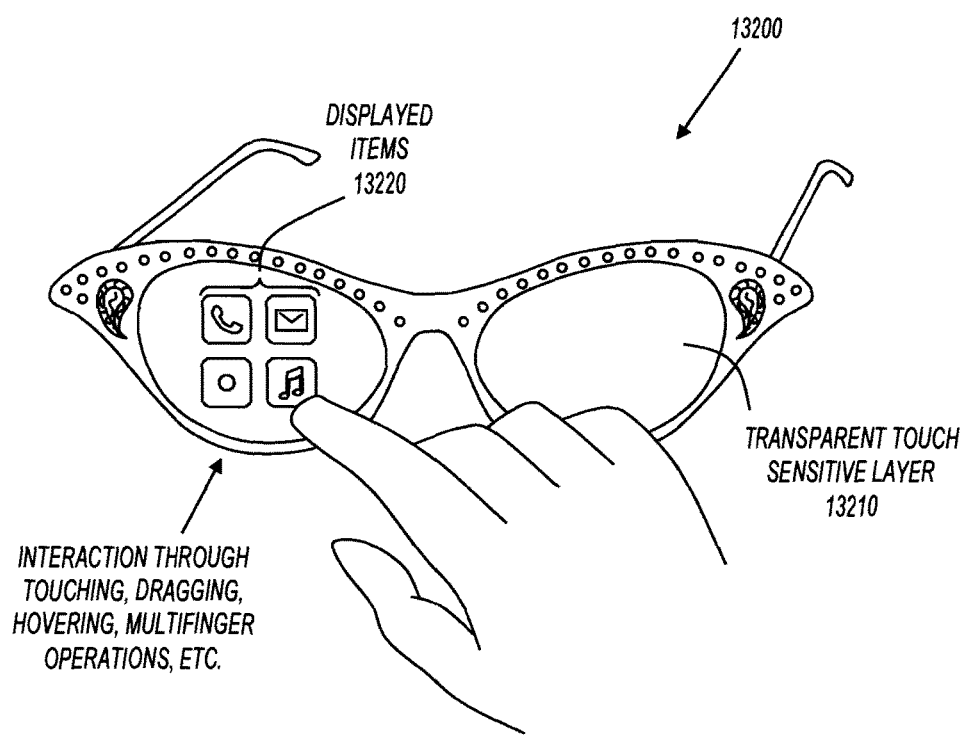
FIG. 132 shows a near-to-eye display device with transparent touch-sensitive layers.

FIG. 132 shows a near-to-eye display device with transparent touch-sensitive layers 13210. In some embodiments, the front surfaces of the near-to-eye display device are covered with transparent touch-sensitive layers that allow for user interaction. For example, a user using near-to-eye display device 13200 can use her fingers to make selections among displayed items 13220 (e.g., some icons/menu items) or to perform actions such as zoom-in and -out operations, and input text data through virtual keyboards, similar to the usage of touch-sensitive screens on existing smart phones, tablets, etc., with the difference that the user sees the displayed content through the backside of the display, while she performs the finger touch based input operations through the front side.

The following paragraphs provide further disclosure of various invention embodiments. Each embodiment is fully defined by the recitation of the corresponding paragraph, and no other elements are to be considered essential for that particular embodiment. The embodiments include:

1A1. A near-to-eye display device comprising:
at least one point light source; and
at least one spatial light modulator (SLM) mounted on the near-to-eye display device;
wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
and wherein the useful portion is steerable across the exit pupil plane to follow the motion of a user's eye pupil when the near-to-eye display device is in use so that the user's eye pupil acts as a spatial filter to filter out undesired beams produced by the SLM at the exit pupil plane.

1A2. A near-to-eye display device comprising:
- at least one point light source; and
- at least one spatial light modulator (SLM) mounted on the near-to-eye display device;
- wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
- and wherein the useful portion is steerable to an expected location of a user's eye pupil when the near-to-eye display device is in use so that the user's eye pupil acts as a spatial filter to filter out undesired beams produced by the SLM at the exit pupil plane.

1A3. A near-to-eye display device comprising:
- at least one point light source; and
- at least one spatial light modulator (SLM) mounted on the near-to-eye display device;
- wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
- and wherein the light wave distribution is determined using a computation that adds a controlled phase variation on the virtual scene to reduce speckle.

1A4. A near-to-eye display device comprising:
- at least one point light source; and
- at least one spatial light modulator (SLM) mounted on the near-to-eye display device;
- wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
- and wherein the light wave distribution is determined using a computation that adds a phase delay variation to the virtual-scene points such that individual waves from the virtual-scene points arrive to the useful portion in-phase to reduce speckle.

1A5. A near-to-eye display device comprising:
- at least one point light source; and
- at least one spatial light modulator (SLM) mounted on the near-to-eye display device;
- wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
- and wherein the light wave distribution is determined using a computation that adds a phase delay variation to the virtual-scene points such that optical path lengths between the useful portion and the virtual-scene points differ by an integer multiple of a center wavelength of the at least one light source.

1A6. A near-to-eye display device comprising:
- at least one point light source; and
- at least one spatial light modulator (SLM) mounted on the near-to-eye display device;
- wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
- and wherein an image viewed through the useful portion of the exit pupil plane exhibits reduced speckle generated by controlling a phase of virtual object points.

1A7. A near-to-eye display device comprising:
- at least one point light source; and
- at least one spatial light modulator (SLM) mounted on the near-to-eye display device;
- wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
- and wherein the light wave distribution is determined using a computation that compensates for optical aberrations of a user's unaided eye.

1A8. A near-to-eye display device comprising:
- at least one point light source; and
- at least one spatial light modulator (SLM) mounted on the near-to-eye display device;
- wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
- and wherein the SLM data is determined using a computation that compensates for optical aberrations of a light path from the at least one point light source to the exit pupil plane.

1A9. A near-to-eye display device comprising:
- at least one point light source; and
- at least one spatial light modulator (SLM) mounted on the near-to-eye display device;
- wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;
- wherein the useful portion is steerable across the exit pupil plane to follow the motion of a user's eye pupil when the near-to-eye display device is in use;
- wherein the user's eye pupil acts as a spatial filter to filter out undesired beams produced by the SLM at the exit pupil plane;
- wherein the waves from a first plurality of subsections of the displayed virtual scene are reconstructed over the entire useful portion so that each of the first plurality of subsections appears focused on the retina only when the user accommodates to the depth of that subsection;
- and wherein the waves from a second subsection of the displayed virtual scene are reconstructed over smaller regions of the useful portion so that these parts always appear focused on the retina.

1A10. A device in accordance with any of paragraphs 1A1-1A34, wherein the SLM produces higher diffraction orders that fall outside the useful portion.

1A11. A device in accordance with any of paragraphs 1A1-1A34, wherein the SLM produces quantization noise that falls outside the useful portion.

1A12. A device in accordance with any of paragraphs 1A1-1A34, wherein the SLM produces conjugate beams that fall outside the useful portion.

1A13. A device in accordance with any of paragraphs 1A1-1A34, wherein the SLM produces a DC beam that falls outside the useful portion.

1A14. A device in accordance with any of paragraphs 1A1-1A34, wherein the virtual scene is two-dimensional.

1A15. A device in accordance with any of paragraphs 1A1-1A34, wherein the virtual scene is three-dimensional.

1A16. A device in accordance with any of paragraphs 1A1-1A34, wherein the modulated light is focused onto the exit pupil plane.

1A17. A device in accordance with any of paragraphs 1A1-1A34, wherein the at least one light source comprising a plurality of light sources that produce light of different wavelengths.

1A18. A device in accordance with any of paragraphs 1A1-1A34, wherein the at least one light source comprising a red light source, a green light source, and a blue light source.

1A19. A device in accordance with any of paragraphs 1A1-1A34, wherein the useful portion of the exit pupil plane substantially overlaps with a user's eye pupil when the near-to-eye display device is in use.

1A20. A device in accordance with any of paragraphs 1A1-1A34, wherein the useful portion of the exit pupil plane is at least as large as an expected size of a user's eye pupil when the near-to-eye display device is in use.

1A21. A device in accordance with any of paragraphs 1A1-1A34, wherein a useful portion of the exit pupil plane matches an expected size of the user's eye pupil.

1A22. A device in accordance with any of paragraphs 1A1-1A34, wherein the light illuminating the spatial light modulator converges, and the useful portion of the exit pupil plane includes a single diffraction order.

1A23. A device in accordance with any of paragraphs 1A1-1A34, wherein the near-to-eye display device comprises a head-worn device.

1A24. A device in accordance with any of paragraphs 1A1-1A34, wherein a ratio of an optical distance between the spatial light modulator and the exit pupil plane to the pixel pitch is greater than an expected pupil size divided by a smallest wavelength of light emitted by the at least one point light source.

1A25. A device in accordance with any of paragraphs 1A1-1A34, wherein the spatial light modulator is in a light path between the at least one point light source and a pupil and not in an optical conjugate plane to a user's retina when the near-to-eye display device is in use.

1A26. A device in accordance with any of paragraphs 1A1-1A34, wherein light projected onto the exit pupil plane includes multiple diffraction orders produced by the spatial light modulator, and the useful portion includes a single diffraction order.

1A27. A device in accordance with any of paragraphs 1A1-1A34, wherein a width of the useful portion is greater than an expected width of a user's eye pupil.

1A28. A device in accordance with any of paragraphs 1A1-1A34, wherein a width of the useful portion is greater than 3 mm.

1A29. A device in accordance with any of paragraphs 1A1-1A34, wherein the light projected on the exit pupil plane includes multiple image copies, and the useful portion includes one image copy.

1A30. A device in accordance with any of paragraphs 1A1-1A34, wherein the spatial light modulator modulates only phase of the light illuminating the SLM.

1A31. A device in accordance with any of paragraphs 1A1-1A34, wherein the spatial light modulator modulates only amplitude of the light illuminating the SLM.

1A32. A device in accordance with any of paragraphs 1A1-1A34, wherein the spatial light modulator modulates phase and amplitude.

1A33. A device in accordance with any of paragraphs 1A1-1A34, wherein the spatial light modulator is reflective.

1A34. A device in accordance with any of paragraphs 1A1-1A34, wherein the spatial light modulator is transmissive.

1A35. A device in accordance with any of paragraphs 1A1-1A34, wherein the useful portion is steerable across the exit pupil plane to follow the motion of a user's eye pupil when the near-to-eye display device is in use.

1A36. A device in accordance with any of paragraphs 1A1-1A34, wherein the useful portion is steerable to an expected location of a user's eye pupil when the near-to-eye display device is in use.

1A37. A device in accordance with any of paragraphs 1A1-1A34, wherein the light wave distribution is determined using a computation that adds a controlled phase variation on the virtual scene to reduce speckle.

1A38. A device in accordance with any of paragraphs 1A1-1A34, wherein the light wave distribution is determined using a computation that adds a phase delay variation to the virtual-scene points such that individual waves from the virtual-scene points arrive to the useful portion in-phase to reduce speckle.

1A39. A device in accordance with any of paragraphs 1A1-1A34, wherein the light wave distribution is determined using a computation that adds a phase delay variation to the virtual-scene points such that optical path lengths between the useful portion and the virtual-scene points differ by an integer multiple of a center wavelength of the at least one light source.

1A40. A device in accordance with any of paragraphs 1A1-1A34, wherein an image viewed through the useful portion of the exit pupil plane exhibits reduced speckle generated by controlling a phase of virtual object points.

1A41. A device in accordance with any of paragraphs 1A1-1A34, wherein the light wave distribution is determined using a computation that compensates for optical aberrations of a user's unaided eye.

1A42. A device in accordance with any of paragraphs 1A1-1A34, wherein the SLM data is determined using a computation that compensates for optical aberrations of a light path from the at least one point light source to the exit pupil plane.

1B1. A near-to-eye display device comprising:
an array of point light sources mounted to the near-to-eye display device; and
a spatial light modulator illuminated by the array of point light sources in a time sequential manner, the spatial light modulator having a plurality of sections that project diverging light toward an exit pupil plane positioned at an expected location of a user's eye pupil when the near-to-eye display device is in use;
wherein the spatial light modulator and the array of point light sources are positioned such that each of the plurality of sections contributes to the light wave in the useful portion of the exit pupil plane with the highest optical power when the corresponding point light source of the array is turned on.

1B2. The near-to-eye display device of 1B1 wherein the array of point light sources comprises a plurality of groups of point light sources, with more than one point light source in a group, and the point light sources within each of the plurality of groups can be turned on at the same time.

1B3. The near-to-eye display device of 1B1, wherein the near-to-eye display device comprises a head-worn device.

1B4. A near-to-eye display device comprising:
an array of point light sources with restricted emission cones mounted to the near-to-eye display device; and
a spatial light modulator illuminated simultaneously by the array of point light sources with restricted emission cones, the spatial light modulator having a plurality of sections that project diverging light toward an exit pupil plane positioned at an expected location of a user's eye pupil when the near-to-eye display device is in use;
wherein the spatial light modulator and the array of point light sources are positioned such that each of the plurality of sections are illuminated only by one of the point light sources in the array.

1B5. The near-to-eye display device of 1B4 further comprising a second array of point light sources with restricted emission cones, wherein the array of point light sources and the second array of point light sources partition the SLM differently with nonoverlapping borders, and wherein the array of point light sources and the second array of point light sources are turned on in a time sequential manner.

1B6. The near-to-eye display device of 1B4, wherein the near-to-eye display device comprises a head-worn device.

1B7. A method comprising:
determining a plurality of data sets to be programmed in a spatial light modulator (SLM) in a near-to-eye display device that includes an array of point light sources, wherein for a video frame of a virtual scene, a different data set for each of the point light sources in the array is computed; and
displaying the plurality of data sets on the SLM in a time sequential manner in synchronism with a corresponding point light source within an overall time allocated for the video frame.

1B8. A method comprising:
determining a plurality of data sets to be programmed in a spatial light modulator (SLM) in a near-to-eye display device that includes an array of point light sources with restricted emission cones, wherein each point light source in the array illuminates a different section of the SLM, and wherein for a video frame of a virtual scene, one data set for each different section of the SLM is computed according to the point light source which illuminates that section of the SLM; and
concatenating the plurality of data sets for the different sections to obtain a final SLM data for the video frame.

1C1. A near-to-eye display device comprising:
a point light source;
a spatial light modulator (SLM), wherein light produced by the point light source illuminates the SLM and gets modulated to produce modulated light, and the modulated light is directed on an exit pupil plane that includes a useful portion, and wherein a light wave distribution within the useful portion is equal to a computed light distribution from a virtual scene; and
a microdisplay positioned on the near-to-eye display device to generate on a user's retina a defocused peripheral image that surrounds a focused image generated by the spatial light modulator.

1C2. A near-to-eye display device comprising:
a point light source;
a spatial light modulator (SLM), wherein light produced by the point light source illuminates the SLM and gets modulated to produce modulated light, and the modulated light is directed on an exit pupil plane that includes a useful portion, and wherein a light wave distribution within the useful portion is equal to a computed light distribution from a virtual scene; and
a microdisplay positioned on the near-to-eye display device to generate a defocused low-resolution image that surrounds an image generated by the spatial light modulator.

1C3. The near-to-eye display device of any of 1C1-1C2, wherein the SLM has a first resolution and the microdisplay has a second resolution that is lower than the first resolution.

1C4. The near-to-eye display device of any of 1C1-1C2, wherein the SLM has a first pixel pitch and the microdisplay has a second pixel pitch that is greater than the first pixel pitch.

1-C5. The near-to-eye display device of any of 1C1-1C2, wherein the modulated light is steerable across the exit pupil plane to follow the motion of a user's eye pupil when the near-to-eye display device is in use.

1-C6. The near-to-eye display device of any of 1C1-1C2 wherein the point light source comprises a plurality of light sources to emit light of different wavelengths.

1C7. The near-to-eye display device of any of 1C6 wherein the plurality of light sources emit light sequentially.

1C8. The near-to-eye display device of any of 1C1-1C2 wherein the SLM is mounted on a movable platform.

IC9. The near-to-eye display device of any of 1C1-1C2 wherein the SLM is mounted on a slotted movable platform.

IC10. The near-to-eye display device of any of 1C1-1C2 wherein the SLM includes at least one row of pixels.

IC11. The near-to-eye display device of any of 1C1-1C2 wherein the SLM has a vertical dimension of at least 2 mm.

IC12. The near-to-eye display device of any of 1C1-1C2 wherein the SLM presents a horizontal field of view of about 30 degrees.

IC13. The near-to-eye display device of any of 1C1-1C2 wherein the SLM presents a horizontal field of view of about 40 degrees.

1C14. The near-to-eye display device of any of 1C1-1C2 wherein the microdisplay is mounted on a movable platform.

IC15. The near-to-eye display device of any of 1C1-1C2 wherein the microdisplay is mounted on a slotted movable platform.

1C16. The near-to-eye display device of any of 1C1-1C2 wherein the microdisplay can be selected from an organic light emitting diode (OLED) display, a transmissive liquid crystal display (LCD), or a reflective LCD.

1C17. The near-to-eye display device of any of 1C1-1C2, wherein the near-to-eye display device comprises a head-worn device.

1C18. A near-to-eye display device comprising:
a spatial light modulator capable of modulating reflected light or displaying color pixels; and
a pupil-tracking device to track a user's pupil position; and
a spatial light modulator driver circuit responsive to the pupil-tracking device to cause the spatial light modulator to modulate reflected light in a central region of the user's gaze and to display color pixels away from the central region of the user's gaze.

1C19. The near-to-eye display device of 1C18, wherein the near-to-eye display device comprises a head-worn device.

1D1. In a near-to-eye display device that includes a spatial light modulator (SLM) to modulate incident light and direct modulated light on an exit pupil plane that includes a useful portion, wherein a light wave distribution within the useful portion is equal to a computed light distribution from a virtual scene, a method comprising:

modifying the light wave distribution to present a user with a plurality of test images intended to determine a type of visual disorder suffered by the user;

receiving feedback from the user regarding the plurality of test images;

determining the type of visual disorder suffered by the user; and modifying the light wave distribution to present the user with a second plurality of test images to determine a degree of the visual disorder suffered by the user.

1D2. In a near-to-eye display device that includes a spatial light modulator (SLM) to modulate incident light and direct modulated light on an exit pupil plane that includes a useful portion, wherein a light wave distribution within the useful portion is equal to a computed light distribution from a virtual scene, a method comprising:

prompting a user to identify a type of any visual disorder of the user;

modifying the light wave distribution to present the user with at least one test image intended to determine a degree of the visual disorder; and receiving feedback from the user regarding the at least one test image.

1D3. In a near-to-eye display device that includes a spatial light modulator (SLM) to modulate incident light and direct modulated light on an exit pupil plane that includes a useful portion, wherein a light wave distribution within the useful portion is equal to a computed light distribution from a virtual scene, a method comprising:

prompting a user to identify a type and degree of any visual disorder of the user;

modifying the light wave distribution to present the user with at least one test image intended to correct for the visual disorder; and receiving feedback from the user regarding the at least one test image.

1D4. The method of any of 1D1-1D3, wherein the test image comprises multiple test images presented sequentially.

1D5. The method of any of 1D1-1D3, wherein the test image comprises multiple test images presented serially.

1D6. The method of any of 1D1-1D3, wherein the feedback comprises selection of one of the multiple test images.

1D7. The method of any of 1D1-1D3, wherein the receiving feedback comprises receiving information from a transducer.

1D8. The method of 1D7 wherein the transducer comprises an adjustment knob.

1D9. The method of any of 1D1-1D3, wherein the user selects an image and then interacts with a transducer to provide feedback.

1D10. The method of any of 1D1-1D3, wherein the feedback from the user is used to adjust for interpupil distance variations.

1D11. The method of any of 1D1-1D3, wherein the feedback from the user is used to adjust for eye relief variations.

1D12. The method of any of 1D1-1D11 further comprising providing the user with a corrected image.

1D13. The method of any of 1D1-1D12 wherein the near-to-eye display device comprises a head-worn device.

1D14. A near-to-eye display device comprising:

at least one point light source;

at least one spatial light modulator (SLM) mounted on the near-to-eye display device, wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene; and a display-calibration component to modify the light wave distribution based on user selection of test images in order to compensate for one or more visual disorders of the user.

1D15. The near-to-eye display device of 1D14 further comprising a transducer coupled to the display-calibration component to receive user feedback.

1D16. The near-to-eye display device of 1D15 wherein the transducer comprises an adjustment knob.

1D17. The near-to-eye display device of 1D14 wherein the display-calibration component includes a processor and a memory device having instructions stored thereon that when executed by the processor perform display calibration.

1D18. The near-to-eye display device of 1D14 wherein the display-calibration component modifies phase values of the light distribution.

1D19. The near-to-eye display device of 1D14 wherein the display-calibration component performs any of the actions of 1D1-1D12

1D20. The near-to-eye display device of 1D14, wherein the near-to-eye display device comprises a head-worn device.

1E1. A near-to-eye display device comprising:

at least one point light source;

at least one spatial light modulator (SLM) mounted on the near-to-eye display device, wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;

a camera; and a display-calibration component to modify data patterns presented to the SLM based on images captured by the camera.

1E2. A near-to-eye display device comprising:

at least one point light source;

at least one spatial light modulator (SLM) mounted on the near-to-eye display device, wherein light produced by the at least one point light source illuminates the SLM and gets modulated to produce modulated light, and the modulated light is directed on an exit pupil plane that includes a useful portion, and wherein a light wave distribution within the useful portion is equal to a computed light distribution from a virtual scene;

a camera;

at least one actuator to modify physical characteristics of the near-to-eye display device; and a display-calibration component coupled to the at least one actuator to modify the physical characteristics of the near-to-eye display device based on images captured by the camera.

1E3. The near-to-eye display device of any of 1E1-1E2 wherein the virtual scene includes test images to measure user physical characteristics.

1E4. The near-to-eye display device of 1E3 wherein the test images are displayed at different depths.

1E5. The near-to-eye display device of 1E3 wherein the test images are displayed at different transverse positions.

1E6. The near-to-eye display device of 1E5 wherein the test images are used to determine actuator settings to compensate for variations in interpupil distance.

1E7. The near-to-eye display device of 1E1-1E2, wherein the near-to-eye display device comprises a head-worn device.

1E8. In a near-to-eye display device that includes a spatial light modulator (SLM) to modulate incident light and direct modulated light on an exit pupil plane that includes a useful portion, wherein a light wave distribution within the useful portion is equal to a computed light distribution from a virtual scene, a method comprising:
displaying at least one test image;
recording images of a user's eyes while viewing the at least one test image;
analyzing the recorded images for user characteristics;
interacting with at least one actuator to compensate for the user characteristics.

1E9. The method of 1E8 wherein recording images of a user's eyes comprises recording the images using two cameras.

1E10. The method of 1E8 wherein analyzing the recording images for user characteristics comprises recording a position of the user's pupils.

1E11. The method of 1E8 wherein analyzing the recording images for user characteristics comprises recording an interpupil distance between the user's pupils.

1E12. The method of 1E8 wherein analyzing the recording images for user characteristics comprises measuring a user's eye anomalies.

1E13. The method of 1E8 wherein the near-to-eye display device comprises a head-worn device.

1F1. A method comprising:
determining a two-dimensional complex-valued profile of a virtual-scene wave on a useful portion of an exit pupil plane;
back-propagating the two-dimensional complex-valued profile of the virtual-scene wave on the useful portion of the exit pupil plane to a spatial light modulator plane to determine an ideal two-dimensional complex-valued wave profile at an exit of the spatial light modulator;
determining a two-dimensional complex-valued profile of an illumination wave that will illuminate the spatial light modulator;
extracting the two-dimensional complex-valued wave profile of the illumination wave from the ideal two-dimensional complex-valued wave profile at the exit of the spatial light modulator to obtain a two-dimensional ideal analog complex-valued spatial light modulator transmittance;
apply prefiltering and sampling to the two-dimensional ideal analog complex-valued spatial light modulator transmittance to obtain a two-dimensional ideal complex-valued discrete spatial light modulator image; and
encoding the two-dimensional ideal complex-valued discrete spatial light modulator image into a two-dimensional actual digital spatial light modulator image that is suitable for displaying by the spatial light modulator, where noise introduced by the spatial light modulator is distributed to regions outside the useful portion.

1F2. The method of 1F1 wherein determining a two-dimensional complex-valued profile of a virtual scene on a useful portion of an exit pupil plane comprises using a point cloud object model to represent a virtual object as a plurality of point light sources.

1F3. The method of 1F2 wherein determining a two-dimensional complex-valued profile of a virtual scene on a useful portion of an exit pupil plane comprises adding a spherical wave term for each of the plurality of point light sources.

1F4. The method of 1F1 wherein determining a two-dimensional complex-valued profile of a virtual scene on a useful portion of an exit pupil plane comprises taking an RGB image rendered by a graphics processing unit (GPU) for a viewpoint along with zBuffer data provided by the GPU, and representing the object surface facing the viewpoint as a plurality of point light sources with corresponding RGB values and depth locations.

1F5. The method of 1F1 wherein determining a two-dimensional complex-valued profile of a virtual-scene wave on a useful portion of an exit pupil plane comprises:
partitioning the virtual scene into a plurality of spherical surfaces concentric at the center of the useful portion of the exit pupil plane with different radius;
forming a matrix for each of the spherical surfaces where each element of the matrix is associated with a specific angular location on the sphere, and each element is filled with the complex amplitude of the point source at that angular location on the sphere;
inverse Fourier transforming the matrix to create a result;
multiplying the result by a common diverging lens term with a focal length equal to the radius of the sphere; and
repeating the partitioning, forming, inverse Fourier transforming, and multiplying for each of the plurality of spherical surfaces and superposing to find the two-dimensional complex-valued profile of the virtual-scene wave on the useful portion of the exit pupil plane.

1F6. The method of 1F1 wherein back-propagating comprises incorporating free-space propagation and wave optics models of any optical components including aberrations introduced by the components between the spatial light modulator and the useful portion of the exit pupil plane.

1F7. The method of 1F1 wherein determining a two-dimensional complex-valued profile of an illumination wave comprises performing free-space propagation and wave optics analysis for components within an illumination module including aberrations.

1F8. The method of 1F1 wherein encoding comprises encoding as a phase-only hologram.

1F9. The method of 1F1 wherein encoding comprises encoding an amplitude-only hologram.

1F10. The method of 1F1 wherein encoding comprises encoding as a binary hologram.

1F11. For objects closer than 25 cm, the size of the useful portion is taken to be smaller than 2 mm, a typical value being 1 mm, so that a sharp retinal image of these objects can also be delivered to the retina using the pinhole imaging principle. The images have infinite depth of focus.

1G1. A method comprising:
determining a two-dimensional complex-valued profile of a virtual-scene wave on a useful portion of an exit pupil plane using a point cloud virtual-scene model to represent a virtual scene as a plurality of virtual-scene points;
assigning a phase value to each of the plurality of virtual-scene points to reduce speckle;
back-propagating the two-dimensional complex-valued profile of the virtual-scene wave on the useful portion of the exit pupil plane to a spatial light modulator plane to determine an ideal two-dimensional complex-valued wave profile at an exit of the spatial light modulator;
determining a two-dimensional complex-valued profile of an illumination wave that will illuminate the spatial light modulator;

extracting the two-dimensional complex-valued wave profile of the illumination wave from the ideal two-dimensional complex-valued wave profile at the exit of the spatial light modulator to obtain a two-dimensional ideal analog complex-valued spatial light modulator transmittance;

apply prefiltering and sampling to the two-dimensional ideal analog complex-valued spatial light modulator transmittance to obtain a two-dimensional ideal complex-valued discrete spatial light modulator image; and encoding the two-dimensional ideal complex-valued discrete spatial light modulator image into a two-dimensional actual digital spatial light modulator image that is suitable for displaying by the spatial light modulator, where noise introduced by the spatial light modulator is distributed to regions outside the useful portion.

1G2. The method of 1G1 wherein assigning a phase value to each of the plurality of virtual-scene points to reduce speckle comprises assigning phase values to produce a smoothly interpolated version of a plurality of points on a user's retina.

1G3. The method of 1G1 wherein assigning a phase value to each of the plurality of virtual-scene points to reduce speckle comprises assigning phase values to make optical paths from the virtual-scene points to the retina differ by integer multiples of a center wavelength of the light source.

1G4. The method of 1G1 wherein assigning a phase value to each of the plurality of virtual-scene points to reduce speckle comprises assigning phase values to make optical paths from the plurality of virtual-scene points to the pupil differ by integer multiples of a center wavelength of the light source.

1G5. The method of 1G1 wherein determining a two-dimensional complex-valued profile of a virtual-scene wave on a useful portion of an exit pupil plane comprises adding a spherical wave term for each of the plurality of virtual-scene points.

1G6. The method of 1G1 wherein back-propagating comprises incorporating wave optics models of any optical components between the spatial light modulator and the useful portion of the exit pupil plane.

1G7. The method of 1G1 wherein determining a two-dimensional complex-valued profile of an illumination wave comprises performing wave optics analysis for components within an illumination module.

1G8. The method of 1G1 wherein encoding comprises encoding as a phase-only mask.

2A1. An apparatus comprising:
a transparent substrate having a first face through which a coherent light beam emanates;
a light-scattering apparatus embedded in the substrate that scatters light away from the first face; and
a reflective optical element to reflect the light from the scattering apparatus to the first face and create the coherent light beam.

2A2. An apparatus to create a coherent light beam comprising:
a transparent substrate having a face and an embedded light-scattering apparatus;
a light guiding apparatus positioned within the substrate to receive light from outside the substrate and guide the light to the embedded light-scattering apparatus; and
a reflective optical element to reflect light scattered by the scattering apparatus to the face to create the coherent light beam.

2A3. An apparatus that includes a near-to-eye display device comprising:

at least one point light source;
a transparent substrate having a first face through which a coherent light beam emanates;
a light-scattering apparatus embedded in the substrate to receive light from the at least one point light source and scatter light away from the first face;
a reflective optical element to reflect the light from the scattering apparatus to the first face to create the coherent light beam; and
a spatial light modulator mounted on the near-to-eye display device and illuminated by the coherent light beam, wherein the spatial light modulator is not in an optical conjugate plane to a retina of a user using the near-to-eye display device.

2A4. An apparatus in accordance with any of 2A1-2A27 wherein the coherent light beam comprises a converging light beam.

2A5. An apparatus in accordance with any of 2A1-2A27 wherein the coherent light beam comprises a diverging light beam.

2A6. An apparatus in accordance with any of 2A1-2A27 wherein the coherent light beam comprises a collimated light beam.

2A7. An apparatus in accordance with any of 2A1-2A27 wherein the reflective optical element comprises a micro-mirror array.

2A8. An apparatus in accordance with any of 2A1-2A27 wherein the reflective optical element comprises a Fresnel mirror.

2A9. An apparatus in accordance with any of 2A1-2A27 wherein the reflective optical element comprises a freeform optical reflector.

2A10. An apparatus in accordance with any of 2A1-2A27 wherein the reflective optical element comprises a concave mirror.

2A11. An apparatus in accordance with any of 2A1-2A27 wherein the reflective optical element reflects light to create a converging beam that converges in one dimension.

2A12. An apparatus in accordance with any of 2A1-2A27 wherein the reflective optical element reflects light to create a converging beam that converges in two dimensions.

2A13. An apparatus in accordance with any of 2A1-2A27, further comprising a spatial light modulator coupled to the first face of the transparent substrate.

2A14. An apparatus in accordance with any of 2A1-2A27, wherein the spatial light modulator is transmissive.

2A15. An apparatus in accordance with any of 2A1-2A27, wherein the spatial light modulator is reflective.

2A16. An apparatus in accordance with any of 2A1-2A27, further comprising:
a point light source; and
a light guide within the substrate to guide light from the point light source to the scattering apparatus.

2A17. An apparatus in accordance with any of 2A1-2A27, further comprising a point light source within the substrate to provide light to the scattering apparatus.

2A18. An apparatus in accordance with any of 2A1-2A27, wherein the point light source comprises an organic light emitting diode (OLED).

2A19. An apparatus in accordance with any of 2A1-2A27, wherein the point light source comprises a red organic light emitting diode (OLED), a green OLED, and a blue OLED.

2A20. An apparatus in accordance with any of 2A1-2A27, wherein the point light source comprises a fluorescent molecule.

2A21. An apparatus in accordance with 2A20, wherein the fluorescent molecule comprises a quantum dot.

2A22. An apparatus in accordance with any of 2A1-2A27, wherein the reflective optical element is embedded in the substrate.

2A23. An apparatus in accordance with any of 2A1-2A27, wherein the reflective optical element is transreflective.

2A24. An apparatus in accordance with any of 2A1-2A27, further comprising a point light source to provide light to the light guiding apparatus.

2A25. An apparatus in accordance with any of 2A1-2A27, wherein the at least one point light source comprises a red light source, a green light source, and a blue light source.

2A26. An apparatus in accordance with any of 2A1-2A27, further comprising a light guide within the transparent substrate to guide light from the at least one point light source to the light-scattering apparatus.

2A27. An apparatus in accordance with any of 2A1-2A27, wherein the near-to-eye display device comprises a head-worn device.

2B1. An apparatus comprising:
a slab waveguide having an input end, an output end, and first and second surfaces parallel to each other to cause light to propagate from the input end to the output end by total internal reflection;
a wedge coupled to receive light from the output end of the slab waveguide, the wedge having a first surface, and a slanted surface nonparallel to the first surface of the wedge to form a continuously decreasing thickness to cause light to exit the wedge from the slanted surface; and
an optical component having a face parallel to the slanted surface of the wedge, the optical component including a micromirror array to reflect light received through the face back through the wedge.

2B2. The apparatus of 2B1 wherein the first surface of the wedge is parallel to the first surface of the slab waveguide.

2B3. The apparatus of 2B1 further comprising a spatial light modulator positioned on the first surface of the slab waveguide to modulate the light as it propagates by total internal reflection.

2B4. The apparatus of 2B1 further comprising a spatial light modulator positioned between the wedge and the micromirror array to modulate the light after leaving the slanted surface.

2B5. The apparatus of 2B1 further comprising a camera for eye tracking.

2B6. The apparatus of 2B5 wherein the camera is positioned along the slab waveguide.

2B7. An apparatus comprising:
a slab waveguide having an input end and an output end, the output end being formed as a first wedge, the first wedge including a first slanted surface through which light exits after propagating from the input end through total internal reflection; and
a compensating wedge that includes a micromirror array to reflect light exiting the first wedge.

2B8. The apparatus of 2B7 wherein the compensating wedge includes a second slanted surface parallel to the first slanted surface.

2B9. The apparatus of 2B7 further comprising a spatial light modulator positioned along the slab waveguide to modulate the light as it propagates by total internal reflection.

2B10. The apparatus of 2B9 further comprising a point light source to provide light to the input end.

2B11. The apparatus of 2B7 further comprising a spatial light modulator positioned between the first wedge and the micromirror array to modulate the light after leaving the first slanted surface.

2B12. The apparatus of 2B7 further comprising a camera for eye tracking.

2B13. The apparatus of 2B12 wherein the camera is positioned along the slab waveguide.

2B14. A near-to-eye display device comprising:
a point light source;
a slab waveguide having an input end, an output end, and first and second surfaces parallel to each other to cause light received from the point light source to propagate from the input end to the output end by total internal reflection;
a wedge coupled to receive light from the output end of the slab waveguide, the wedge having a first surface, and a slanted surface nonparallel to the first surface of the wedge to form a continuously decreasing thickness to cause light to exit the wedge from the slanted surface;
an optical component having a face parallel to the slanted surface of the wedge, the optical component including a micromirror array to reflect light received through the face back through the wedge to create a converging light beam; and
a spatial light modulator illuminated by the converging light beam, wherein the spatial light modulator is not in an optical conjugate plane to a retina of a user using the near-to-eye display device.

2B15. The near-to-eye display device of 2B14 further comprising a spatial light modulator positioned on the first surface of the slab waveguide to modulate the light as it propagates by total internal reflection.

2B16. The near-to-eye display device of 2B14 further comprising a spatial light modulator positioned between the wedge and the micromirror array to modulate the light after leaving the slanted surface.

2B17. The near-to-eye display device of 2B14 further comprising a camera for eye tracking.

2B18. The near-to-eye display device of 2B17 wherein the camera is positioned along the slab waveguide.

2B19. The near-to-eye display device of 2B14 wherein the optical component comprises a compensating wedge that when combined with the wedge produces a uniform thickness.

2B20. The near-to-eye display device of 2B14 wherein the near-to-eye display device comprises a head-worn device.

2C1. An apparatus comprising:
a slab waveguide having an input end, an output end, and first and second surfaces parallel to each other to cause light to propagate from the input end to the output end by total internal reflection;
a curved wedge coupled to receive light from the output end of the slab waveguide, the curved wedge having a continuously decreasing thickness to cause light to exit the wedge from one of two surfaces.

2C2. The apparatus of 2C1 further comprising a spatial light modulator positioned on the first surface of the slab waveguide to modulate the light as it propagates by total internal reflection.

2C3. The apparatus of 2C1 further comprising a camera for eye tracking.

2C4. The apparatus of 2C3 wherein the camera is positioned along the slab waveguide.

2C5. An apparatus comprising:
a slab waveguide having an input end and an output end, and first and second surfaces parallel to each other to cause light to propagate from the input end to the output end by total internal reflection;
a curved wedge coupled to receive light from the output end of the slab waveguide, the curved wedge having a continuously decreasing thickness to cause light to exit the wedge from one of two surfaces; and a compensating curved wedge that provides a uniform optical path length for light passing through both the curved wedge and the compensating curved wedge.

2C6. The apparatus of 2C5 further comprising a spatial light modulator positioned along the slab waveguide to modulate the light as it propagates by total internal reflection.

2C7. The apparatus of 2C5 further comprising a point light source to provide light to the input end.

2C8. The apparatus of 2C5 further comprising a camera for eye tracking.

2C9. The apparatus of 2C8 wherein the camera is positioned along the slab waveguide.

2C10. A near-to-eye display device comprising:
a point light source;
a slab waveguide having an input end, an output end, and first and second surfaces parallel to each other to cause light received from the point light source to propagate from the input end to the output end by total internal reflection;
a curved wedge coupled to receive light from the output end of the slab waveguide, the wedge having first and second surfaces oriented to form a continuously decreasing thickness to cause light to exit the curved wedge from one of the first and second surface and create a converging light beam;
a spatial light modulator illuminated by the converging light beam, wherein the spatial light modulator is not in an optical conjugate plane to a retina of a user using the near-to-eye display device.

2C11. The near-to-eye display device of 2C10 further comprising a compensating curved wedge that provides a uniform optical path length for light passing through both the curved wedge and the compensating curved wedge.

2C12. The near-to-eye display device of 2C10 further comprising a camera for eye tracking.

2C13. The near-to-eye display device of 2C10 wherein the camera is positioned along the slab waveguide.

2C14. The near-to-eye display device of 2C10 wherein the near-to-eye display device comprises a head-worn device.

3A1. A near-to-eye display device comprising:
a movable platform that includes a plurality of light sources; and
a circuit to modulate the plurality of light sources and to synchronize the modulation with motion of the movable platform.

3A2. The near-to-eye display device of 3A1 further comprising a polarizing film to pass environmental light polarized in a first orientation, wherein the plurality of light sources are positioned to direct light toward an expected location of a user's eye.

3A3. The near-to-eye display device of 3A1 wherein the plurality of light sources are positioned to direct light away from an expected location of a user's eye.

3A4. The near-to-eye display device of 3A1 wherein the plurality of light sources includes an array of light sources.

3A5. The near-to-eye display device of 3A4 wherein the array of light sources comprises an array of light emitting diodes.

3A6. The near-to-eye display device of 3A4 wherein the array of light sources comprises light sources of at least two different colors.

3A7. The near-to-eye display device of 3A4 wherein the array of light sources comprises red, green, and blue light sources.

3A8. The near-to-eye display device of 3A4 wherein the array of light sources comprises a one-dimensional array.

3A9. The near-to-eye display device of 3A4 wherein the array of light sources comprises a two-dimensional array.

3A10. The near-to-eye display device of 3A4 wherein the movable platform comprises a bar that moves in one dimension.

3A11. The near-to-eye display device of 3A1 wherein the movable platform comprises a bar mounted on a pivot point.

3A12. The near-to-eye display device of 3A1 wherein the movable platform comprises a plurality of bars that move in one dimension.

3A13. The near-to-eye display device of 3A1 wherein the near-to-eye display device comprises a head-worn device.

3A14. In combination:
a near-to-eye display device that comprises a movable platform that includes a plurality of light sources; and
a contact lens having a first portion and a second portion, the first portion having a high-diopter lens to allow a user to focus at a plane of the plurality of light sources.

3A15. The combination of 3A14 wherein the near-to-eye display device comprises a head-worn device.

3A16. The combination of 3A14 wherein the near-to-eye display device further comprises a polarizing film that polarizes light in a first orientation, the polarizing film being oriented such that environmental light viewed by a user of the near-to-eye display device passes through the polarizing film, and further oriented such that light produced by the plurality of light sources does not pass through the polarizing film.

3A17. The combination of 3A16 wherein the plurality of light sources produce light polarized in a second orientation different from the first orientation.

3A18. The combination of 3A14 wherein the first portion of the contact lens has a polarization matching the polarizing film and the second portion has a polarization matching the light produced by the plurality of light sources.

3A19. The combination of 3A14 wherein the second portion of the contact lens includes color filtering.

3A20. The combination of 3A14 wherein the first and second portions of the contact lens are concentric.

3A21. The combination of 3A14 wherein the plurality of light sources is on a movable platform that sweeps over a viewing area of the near-to-eye display device.

3A22. The combination of 3A21 wherein the movable platform comprises a plurality of bars that move in one dimension.

3A23. The combination of 3A21 wherein the movable platform moves in one dimension.

3A24. The combination of 3A21 wherein the movable platform is mounted to the near-to-eye display device at a pivot point.

3A25. The combination of 3A14 wherein the second portion of the contact lens includes two color filters.

3A26. The combination of 3A14 wherein the second portion of the contact lens includes three color filters.

3A27. The combination of 3A14 wherein the second portion of the contact lens includes four color filters.

3A28. The combination of 3A14 wherein the movable platform is magnetically actuated.

3A29. The combination of 3A14 wherein the movable platform is piezoelectrically actuated.

3A30. The combination of 3A14 wherein the movable platform is electrically actuated.

3A31. A near-to-eye display device comprising:
a point light source; and
a movable platform that includes a spatial light modulator positioned to be illuminated by the point light source such that when the movable platform is swept through a user's field of view, the spatial light modulator projects light on an exit pupil positioned at an expected location of the user's eye pupil when the near-to-eye display device is in use, and wherein the exit pupil plane is at an optical conjugate location of the point light source.

3A32. The near-to-eye display device of 3A31 wherein the spatial light modulator includes a single row of pixels.

3A33. The near-to-eye display device of 3A31 wherein the spatial light modulator includes multiple rows of pixels.

3A34. The near-to-eye display device of 3A31 wherein the point light source is mounted on the moving platform.

3A35. The near-to-eye display device of 3A31 wherein the movable platform comprises a plurality of bars that move in one dimension.

3A36. The near-to-eye display device of 3A31 wherein the moving platform comprises a plurality of bars that each includes at least one row of spatial light modulator pixels.

3A37. The near-to-eye display device of 3A31 further comprising a plurality of light sources of different colors that are time multiplexed when in use.

3A38. The near-to-eye display device of 3A31 wherein the near-to-eye display device comprises a head-worn device.

4A1. A near-to-eye display device comprising:
a point light source;
a spatial light modulator;
a reflective optical element rotatably mounted to the near-to-eye display device and positioned to be illuminated by the at least one point light source to project light on an exit pupil plane positioned at an expected location of a user's eye pupil when the near-to-eye display device is in use;
a pupil-tracking device to determine a position of the user's eye pupil; and
an actuator to rotate the reflective optical element in response to the position of the user's eye pupil.

4A2. The near-to-eye display device of 4A1 wherein the spatial light modulator is reflective.

4A3. The near-to-eye display device of 4A1 wherein the spatial light modulator is transmissive.

4A4. The near-to-eye display device of 4A1 wherein the spatial light modulator is coupled to the reflective optical element such that the spatial light modulator and the reflective optical element rotate together.

4A5. The near-to-eye display device of 4A1 wherein the near-to-eye display device comprises a head-worn device.

4A6. The near-to-eye display device of 4A1 wherein the point light source is mounted on a nose bridge of the near-to-eye display device.

4A7. The near-to-eye display device of 4A1 wherein the point light source is mounted on a frame of the near-to-eye display device.

4A8. The near-to-eye display device of 4A1 wherein the actuator comprises a magnetic actuator.

4A9. The near-to-eye display device of 4A1 wherein the actuator comprises a motor.

4A10. The near-to-eye display device of 4A1 wherein light projected onto the exit pupil plane includes multiple diffraction orders produced by the spatial light modulator, and the actuator causes one of the diffraction orders to follow the position of the user's eye pupil.

4A11. The near-to-eye display device of 4A1, wherein light projected onto the exit pupil plane includes multiple diffraction orders produced by the spatial light modulator, and the actuator causes a different diffraction order to follow the position of the user's eye pupil as the position changes.

4A12. The near-to-eye display device of 4A1 further comprising a plurality of point light sources and a light selection component responsive to the pupil-tracking device.

4A13. A method comprising:
tracking the location of a user's eye pupil;
rotating a spatial light modulator that produces multiple diffraction orders so that a single diffraction order enters the user's eye pupil.

4A14. The method of 4A13 wherein tracking comprises measuring an angle, and further comprising driving the spatial light modulator with different data to change the diffraction order that enters the user's eye pupil for angles above a threshold.

4A15. The method of 4A13 wherein tracking comprises measuring an angle, and further comprising selecting a different light source to illuminate the spatial light modulator based on the angle.

4B1. A near-to-eye display device comprising:
a point light source;
a spatial light modulator;
an active grating that implements a multi-section prism disposed between the point light source and the spatial light modulator, the active grating being positioned to be illuminated by the point light source to direct light on the spatial light modulator, the spatial light modulator being positioned to be illuminated by the wave directed by the active grating to direct light on an exit pupil plane positioned at an expected location of a user's eye pupil when the near-to-eye display device is in use;
a pupil-tracking device to determine a position of the user's eye pupil; and
a control circuit to energize the active grating in response to the position of the user's eye pupil.

4B2. A near-to-eye display device comprising:
a point light source;
an optical component that includes a spatial light modulator, a reflector, and an active grating disposed between the reflector and the spatial light modulator, the optical component being positioned to be illuminated by the at least one point light source to project light on an exit pupil plane positioned at an expected location of a user's eye pupil when the near-to-eye display device is in use;
a pupil-tracking device to determine a position of the user's eye pupil; and
a control circuit to energize the active grating in response to the position of the user's eye pupil.

4B3. A near-to-eye display device of any of 4B1-4B2 wherein the near-to-eye display device comprises a head-worn device.

4B4. A method comprising:
tracking the location of a user's eye pupil;
actuating a programmable diffraction grating that steers light to a spatial light modulator that produces multiple diffraction orders so that a single diffraction order enters the user's eye pupil.

4B5. The method of 4B4 wherein tracking comprises measuring an angle, and further comprising driving the spatial light modulator with different data to change the diffraction order that enters the user's eye pupil for angles above a threshold.

4B6. The method of 4B4 wherein tracking comprises measuring an angle, and further comprising selecting a different light source to illuminate the spatial light modulator based on the angle.

Although the present invention has been described in conjunction with certain embodiments, it is to be understood that modifications and variations may be resorted to without departing from the scope of the invention as those skilled in the art readily understand. Such modifications and variations are considered to be within the scope of the invention and the appended claims.

What is claimed is:

1. A near-to-eye display device, wherein the near-to-eye display device when in use is less than 25 cm from a user's eye, the near-to-eye display device comprising:
    a computer unit;
    a plurality of point light sources;
    a spatial light modulator (SLM), wherein light produced by at least one of the plurality of point light sources illuminates the SLM and gets modulated to produce modulated light, and the modulated light is directed on an exit pupil plane that includes a useful portion;
    a reflective optical element rotatably mounted to the near-to-eye display device and positioned to be illuminated by light from the at least one point light source to reflect light on an exit pupil plane positioned at an expected location of a user's eye pupil when the near-to-eye display device is in use, wherein rotation of the reflective optical element causes the useful portion to move within the exit pupil plane;
    a pupil-tracking device to determine a position of the user's eye pupil; and
    an actuator to orient the reflective optical element to a selected orientation, wherein the computer unit activates one or more of the plurality of point light sources and selects the selected orientation in response to the determined position of the user's eye pupil.

2. The near-to-eye display device of claim 1, wherein the spatial light modulator is reflective.

3. The near-to-eye display device of claim 1, wherein the spatial light modulator is coupled to the reflective optical element such that the spatial light modulator and the reflective optical element rotate together.

4. The near-to-eye display device of claim 1, wherein the point light source is mounted on a nose bridge of the near-to-eye display device.

5. The near-to-eye display device of claim 1, wherein the point light source is mounted on a frame of the near-to-eye display device.

6. The near-to-eye display device of claim 1, wherein the actuator comprises a magnetic actuator or a motor.

7. The near-to-eye display device of claim 1, wherein light projected onto the exit pupil plane includes multiple diffraction orders produced by the spatial light modulator, and the actuator causes one of the diffraction orders to follow the position of the user's eye pupil.

8. The near-to-eye display device of claim 1, further comprising a plurality of point light sources and a light selection component responsive to the pupil tracking device.

9. The near-to-eye display device of claim 1, wherein the point light source comprises an LED.

10. The near-to-eye display device of claim 1, wherein the point light source comprises a laser light source.

11. The near-to-eye display device of claim 1, wherein the point light source comprises a red light emitting diode (LED), a green LED, and a blue LED coupled to a fiber.

12. The near-to-eye display device of claim 1, wherein the SLM and reflective optical element are mounted together in a rotation-coupled manner.

13. The near-to-eye display device of claim 1, wherein the spatial light modulator and reflective optical element are attached at one face thereof such that point light sources of a LED array selectively illuminate the spatial light modulator in response to the pupil tracker's new pupil position detection data.

14. The near-to-eye display device of claim 13, wherein the spatial light modulator is rotated for angles smaller than a predetermined angle and different light sources are selected for larger angles such that pupil tracking is effectuated.

15. The near-to-eye display device of claim 14, wherein light wave distribution is recomputed for larger angles such that a higher diffraction order moves into useful portion of the exit pupil plane.

16. The near-to-eye display device of claim 13, wherein the spatial light modulator comprises an active grating.

17. The near-to-eye display device of claim 16, wherein pupil tracking is effectuated, grating is actuated for angles smaller than a predetermined angle and different light sources are selected for larger angles.

18. The near-to-eye display device of claim 17, wherein light wave distribution is recomputed for larger angles such that a higher diffraction order moves into useful portion of the exit pupil plane.

19. The near-to-eye display device of claim 1, wherein the spatial light modulator creates a high-resolution image and the reflective optical element is rotatable to steer the high-resolution image following user's pupil position in the manner that spatial light modulator light is steered towards the pupil and that only a limited degree portion of the field of view of the user is provided by the spatial light modulator and the rest of the field of view of the user is covered by a 2D display.

20. The near-to-eye display device of claim 1, wherein speckle reduction is provided in the manner that the light wave distribution is determined by a computation that adds a controlled phase variation on the virtual scene.

21. A near-to-eye display device, wherein the near-to-eye display device when in use is less than 25 cm from a user's eye, the near-to-eye display device comprising:
    a computer unit;
    a plurality of point light sources;
    a spatial light modulator (SLM), wherein light produced by at least one of the plurality of point light sources illuminates the SLM and gets modulated to produce modulated light, and the modulated light is directed on an exit pupil plane that includes a useful portion;
    a reflective optical element rotatably mounted to the near-to-eye display device and positioned to be illuminated by light from the at least one point light source to project light on an exit pupil plane positioned at an expected location of a user's eye pupil when the near-to-eye display device is in use, wherein rotation of the reflective optical element causes the useful portion to move within the exit pupil plane;
    a pupil-tracking device to determine a position of the user's eye pupil; and
    an actuator to orient the reflective optical element to a selected orientation, wherein the computer unit activates one or more of the plurality of point light sources and selects the selected orientation in response to the determined position of the user's eye pupil, wherein the near-to-eye display device is a head-worn display device, and wherein the SLM is rotatably mounted to the near-to-eye display.

22. A method comprising:

tracking the location of a user's eye pupil;

rotating a spatial light modulator that produces multiple diffraction orders so that a single diffraction order enters the user's eye pupil;

illuminating the spatial light modulator using a first light source; and measuring an angle, and driving the spatial light modulator with different data to change the diffraction order that enters the user's eye pupil for angles above a threshold.

23. A method comprising:

tracking the location of a user's eye pupil;

rotating a spatial light modulator that produces multiple diffraction orders so that a single diffraction order enters the user's eye pupil;

illuminating the spatial light modulator using a first light source; and measuring an angle, and selecting a different second light source to illuminate the spatial light modulator based on the angle.

* * * * *